United States Patent
Fisk et al.

(10) Patent No.: US 9,952,147 B2
(45) Date of Patent: Apr. 24, 2018

(54) RAPID, NON-DESTRUCTIVE, SELECTIVE INFRARED SPECTROMETRY ANALYSIS OF ORGANIC COATINGS ON MOLDED ARTICLES

(71) Applicant: SIO2 MEDICAL PRODUCTS, INC., Auburn, AL (US)

(72) Inventors: Thomas E. Fisk, Green Valley, AZ (US); Kevin Turney, Auburn, AL (US); Robert L. Browning, Auburn, AL (US)

(73) Assignee: SIO2 MEDICAL PRODUCTS, INC., Auburn, AL (US)

( * ) Notice: Subject to any disclaimer, the term of this patent is extended or adjusted under 35 U.S.C. 154(b) by 31 days.

(21) Appl. No.: 14/916,654

(22) PCT Filed: Sep. 12, 2014

(86) PCT No.: PCT/US2014/055309
§ 371 (c)(1),
(2) Date: Mar. 4, 2016

(87) PCT Pub. No.: WO2015/038850
PCT Pub. Date: Mar. 19, 2015

(65) Prior Publication Data
US 2016/0195472 A1    Jul. 7, 2016

Related U.S. Application Data

(60) Provisional application No. 61/877,198, filed on Sep. 12, 2013, provisional application No. 62/048,508, filed on Sep. 10, 2014.

(51) Int. Cl.
*G01J 5/02*   (2006.01)
*G01N 21/3563*   (2014.01)
(Continued)

(52) U.S. Cl.
CPC ....... *G01N 21/3563* (2013.01); *A61M 5/3202* (2013.01); *G01N 21/39* (2013.01);
(Continued)

(58) Field of Classification Search
CPC .......... A61M 5/3202; G01N 2021/399; G01N 21/3563; G01N 21/39; G01N 21/8422;
(Continued)

(56) References Cited

U.S. PATENT DOCUMENTS

2002/0102394 A1* 8/2002 MacQuart ......... B32B 17/10174
428/216
2003/0215625 A1* 11/2003 Golecki .................. C23C 30/00
428/293.4

(Continued)

OTHER PUBLICATIONS

International Search Report and Written Opinion corresponding to International Patent Application No. PCT/US2014/055309, dated May 19, 2015.

(Continued)

*Primary Examiner* — David J Makiya
*Assistant Examiner* — Taeho Jo
(74) *Attorney, Agent, or Firm* — McAndrews, Held & Malloy, Ltd.

(57) ABSTRACT

The invention is directed to a non-destructive method of detecting whether a coating or deposit (30, 34) of (a) $SiO_xC_y$ or $SiN_xC_y$ and/or (b) of $SiO_x$ is present on or near a surface of an article (12), such as a disposable thermoplastic medical article. The method includes impinging infrared light (216) having a wave number in at least a portion of a desired range onto at least a first surface being examined for the presence of the one or more coatings or deposits. At least a portion (224) of the infrared light impinged on the first surface is collected (at 222) and the response output, which may include for example the maximum intensity and/or peak area (Continued)

of the collected infrared light at an infrared spectroscopy peak, is used to indicate the presence of the one or more coatings or deposits.

28 Claims, 27 Drawing Sheets

(51) Int. Cl.
   G01N 21/84 (2006.01)
   G01N 21/90 (2006.01)
   A61M 5/32 (2006.01)
   G01N 21/39 (2006.01)

(52) U.S. Cl.
   CPC ..... *G01N 21/8422* (2013.01); *G01N 21/9072* (2013.01); *G01N 21/9081* (2013.01); *G01N 2021/399* (2013.01); *G01N 2201/06113* (2013.01)

(58) Field of Classification Search
   CPC .......... G01N 21/9072; G01N 21/9081; G01N 2201/06113
   USPC .................................................. 250/339.07
   See application file for complete search history.

(56) References Cited

U.S. PATENT DOCUMENTS

| | | | | |
|---|---|---|---|---|
| 2004/0241457 | A1* | 12/2004 | Macquart | B32B 17/10174 428/432 |
| 2007/0235059 | A1* | 10/2007 | Chu | B08B 7/0035 134/1.1 |
| 2008/0175988 | A1* | 7/2008 | Chiu | C03C 17/22 427/163.2 |
| 2009/0088615 | A1* | 4/2009 | Robinson | A61B 5/14532 600/316 |
| 2009/0167164 | A1* | 7/2009 | Fukuda | C09D 1/00 313/504 |
| 2010/0099226 | A1* | 4/2010 | Sasagawa | H01L 27/1214 438/158 |
| 2010/0112373 | A1* | 5/2010 | Coffey | B32B 33/00 428/608 |
| 2010/0148070 | A1* | 6/2010 | Ho | G01N 21/3581 250/341.8 |
| 2010/0298738 | A1* | 11/2010 | Felts | B05D 1/62 600/576 |
| 2010/0304106 | A1* | 12/2010 | Takano | B05D 1/005 428/216 |
| 2011/0252899 | A1* | 10/2011 | Felts | C23C 16/045 73/865.8 |
| 2012/0097329 | A1* | 4/2012 | Stern | B41C 1/148 156/345.3 |
| 2012/0123345 | A1* | 5/2012 | Felts | A61M 5/3129 604/187 |
| 2012/0170026 | A1* | 7/2012 | Wilcken | G01J 3/02 356/51 |
| 2012/0206710 | A1* | 8/2012 | Niemela | G01B 11/0633 356/4.07 |
| 2012/0320380 | A1* | 12/2012 | Schonleber | G01B 11/0625 356/479 |
| 2013/0041241 | A1* | 2/2013 | Felts | C23C 16/045 600/364 |
| 2013/0050687 | A1* | 2/2013 | Aizenberg | G01B 11/0633 356/128 |
| 2013/0109278 | A1* | 5/2013 | Kimba | B24B 49/04 451/5 |
| 2013/0196365 | A1* | 8/2013 | Reddy | C23C 4/04 435/32 |
| 2013/0291632 | A1* | 11/2013 | Felts | C23C 16/045 73/150 R |
| 2013/0328025 | A1* | 12/2013 | Ono | H01L 51/5253 257/40 |
| 2014/0004022 | A1* | 1/2014 | Sagona | C23C 16/045 422/558 |
| 2014/0069202 | A1* | 3/2014 | Fisk | A61M 5/3129 73/762 |
| 2014/0087101 | A1* | 3/2014 | Tixhon | C03C 17/3417 428/34 |
| 2014/0133031 | A1* | 5/2014 | Coffey | B32B 33/00 359/601 |
| 2014/0182380 | A1* | 7/2014 | Cetinkaya | G01N 29/12 73/579 |
| 2015/0021339 | A1* | 1/2015 | Felts | C23C 16/30 220/626 |
| 2015/0044454 | A1* | 2/2015 | Hasegawa | C04B 35/565 428/336 |
| 2015/0098084 | A1* | 4/2015 | Felts | A61M 5/3129 356/432 |

OTHER PUBLICATIONS

Bester et al., "IR-karakterisering van du soliede SiOxCy-lagies [IR characterization of SiOxCy thin solid films]", South-African Journal of Chemistry, vol. 48, No. 3/4, Jan. 1, 1995.

Innocenzi, "Infrared spectroscopy of sol-gel derived silica-based films: a spectra-microstructure overview", Journal of Non-Crystalline Solids, vol. 316, No. 2-3, Feb. 1, 2003.

\* cited by examiner

RAPID, NON-DESTRUCTIVE, SELECTIVE INFRARED SPECTROMETRY ANALYSIS OF ORGANIC COATINGS ON MOLDED ARTICLES

CROSS-REFERENCE TO RELATED APPLICATIONS

This application claims the priority of U.S. Ser. No. 61/877,198, filed Sep. 12, 2013, and U.S. Ser. No. 62/048,508, filed Sep. 10, 2014. This application is the national stage of PCT/US2014/055309, having an international filing date of Sep. 12, 2014, published as WO 2015/038850 A2 on Mar. 19, 2015. The entire content of each of these applications is hereby incorporated herein by reference for all purposes, including to provide continuity of disclosure.

BACKGROUND OF THE INVENTION

The present invention relates generally to rapid, non-destructive, selective infrared spectrometry analysis of organic coatings on molded articles. More particularly, the invention relates to such analysis of sub-micron coatings and mold lubricant residues on disposable thermoplastic medical articles such as syringes, auto-injector cartridges, and vials used to contain, store, or deliver pharmaceutical agents, body fluids, diagnostic reagents, and other fluid materials.

The present invention also relates to a pharmaceutical package or other container and to a method for coating or layering an inner or interior surface of a pharmaceutical package or other container. The present invention also relates more generally to medical devices, including devices other than packages or containers, for example catheters.

The present disclosure also relates to improved methods for processing pharmaceutical packages or other containers, for example multiple identical pharmaceutical packages or other containers used for pharmaceutical preparation storage and delivery, venipuncture and other medical sample collection, and other purposes. Such pharmaceutical packages or other containers are used in large numbers for these purposes, and must be relatively economical to manufacture and yet highly reliable in storage and use.

One important consideration in manufacturing pre-filled syringes and cartridges or other containers (such as vials) for storing or other contact with fluids, for example, is that the contents of the pharmaceutical package or other container desirably will have a substantial shelf life. During this shelf life, it is important to isolate the material filling the pharmaceutical package or other container from the container wall containing it, or from a barrier coating or layer or other functional coatings or layers applied to the pharmaceutical package or other container wall to avoid leaching material from the pharmaceutical package or other container wall, barrier coating or layer, or other functional coatings or layers into the prefilled contents or vice versa.

Commonly, after it is filled, a prefilled syringe or cartridge is capped at the distal end, as with a needle shield or other type of cap, and is closed at the proximal end by its drawn plunger tip or piston. The prefilled syringe or cartridge can be wrapped in a sterile package before use. To use the prefilled syringe or cartridge, the packaging and needle shield or other type of cap are removed, optionally a hypodermic needle or other type of dispenser is attached (if not already present), the delivery conduit or syringe is moved to a use position (such as by inserting the hypodermic needle into a patient's blood container or into apparatus to be rinsed with the contents of the syringe), and the plunger tip or piston is advanced in the barrel to inject the contents of the barrel. If a cartridge is being used, it is also placed into a mechanism that mechanically advances the piston to make an injection, for example using an injection spring.

Another important consideration is reliability of manufacture of pre-filled syringes, cartridges, vials, or other containers for storing or otherwise contacting injectable pharmaceutical materials and other fluids. Since many of these containers are inexpensive and used in large quantities, for certain applications it will be useful to reliably obtain the necessary shelf life without increasing the manufacturing cost to a prohibitive level. To address this need, it will be useful to develop rapid, inexpensive inspection methods that can be used to non-destructively inspect each container manufactured for any defects that may impact on its performance. For example, the coatings applied to thermoplastic containers to improve their barrier properties and prevent interaction of fluid contents with the container are desirably inspected before filling the containers with a costly medication or diagnostic material.

Traditional infrared (IR) spectrometry methods for detection of submicron coatings are IR reflectance methods, such as Fourier Transform Infrared-Attenuated Total Reflectance (FTIR-ATR). These methods require contact of the coating with an ATR crystal having a flat surface, typically made of sapphire. As a consequence, non-flat coated substrates (e.g. vials, syringe barrels) must be cut into small sections and compressed onto this sapphire stage for measurement, which is a destructive test. Also, contact of the coating surface to the spectrometer sapphire window is required, which can affect the coating.

These methods will tend to damage the coating, and thus are undesirable for inspection of the actual containers to be filled with a pharmaceutical or diagnostic material and distributed for medical use.

SUMMARY OF THE INVENTION

An aspect of the invention is a non-destructive method of detecting whether a coating or deposit of $SiO_xC_y$ or $SiN_xC_y$, where x can be from about 0.5 to about 2.4 and y can be from about 0.6 to about 3, is present on or near a surface of an article. The method includes impinging, collecting, and measuring steps.

The impinging step includes impinging infrared light having a wave number in one or more of (a) at least a portion of a range between 950 and 1230 $cm^{-1}$ and (b) at least a portion of a range between 1230 and 1300 $cm^{-1}$, for example from a source, onto at least a first surface being examined for the presence of a coating or deposit of $SiO_xC_y$ or $SiN_xC_y$.

The collecting step includes collecting at least a portion of the infrared light impinged on the first surface, as with a collector.

The measuring step includes measuring the response output, which may include for example the maximum intensity and/or peak area of the collected infrared light at an infrared spectroscopy peak, in one or more of (a) at least a portion of a range between 950 and 1230 $cm^{-1}$ and (b) at least a portion of a range between 1230 and 1300 $cm^{-1}$. For example, the coating or deposit of $SiO_xC_y$ or $SiN_xC_y$ can be indicated by an infrared spectroscopy peak in the wave number range of one or more of (a) at least a portion of a range from about 1015 to about 1035 $cm^{-1}$ and (b) at least a portion of a range from about 1245 to about 1270 $cm^{-1}$, each being indicative of a coating or deposit of $SiO_xC_y$ or $SiN_xC_y$.

Still another aspect of the invention is a method of treating an article with coatings or deposits. An article including a first surface can be provided. A coating or deposit of $SiO_xC_y$ or $SiN_xC_y$, where x can be from about 0.5 to about 2.4 and y can be from about 0.6 to about 3, can be applied on the first surface. The coating or deposit of $SiO_xC_y$ or $SiN_xC_y$ is generally from 5 to 200 nm thick, optionally from 5 to 100 nm thick, and optionally from 5 to 20 nm thick. A coating of $SiO_x$, in which x can be from about 1.5 to about 2.9, can be applied over the coating or deposit of $SiO_xC_y$ or $SiN_xC_y$. The coating or deposit of $SiO_xC_y$ or $SiN_xC_y$, measured in the presence of the first surface and in the presence of the coating or deposit of $SiO_x$, can be distinguished by a detectable response, such as an infrared spectroscopy peak, in one or more of (a) at least a portion of a range between 950 and 1230 $cm^{-1}$ and (b) at least a portion of a range between 1230 and 1300 $cm^{-1}$, indicative of a coating or deposit of $SiO_xC_y$ or $SiN_xC_y$. For example, the coating or deposit of $SiO_xC_y$ or $SiN_xC_y$, measured in the presence of the first surface and in the presence of the coating or deposit of $SiO_x$, can be distinguished by a detectable infrared spectroscopy peak in the wave number range of one or more of (a) at least a portion of a range from about 1015 to about 1035 $cm^{-1}$ and (b) at least a portion of a range from about 1245 to about 1270 $cm^{-1}$, each being indicative of a coating or deposit of $SiO_xC_y$ or $SiN_xC_y$.

Another aspect of the invention is a non-destructive method of detecting whether a coating or deposit of $SiO_x$, where x is from about 1.5 to about 2.9, is present on or near a surface of an article. The method includes impinging, collecting, and measuring steps.

The impinging step includes impinging infrared light having a wave number in at least a portion of the range from about 1060 to about 1080 $cm^{-1}$, for example from a source, onto at least a first surface being examined for the presence of a coating or deposit of $SiO_x$.

The collecting step includes collecting at least a portion of the infrared light impinged on the first surface, as with a collector.

The measuring step includes measuring the response output, which may include for example the maximum intensity and/or peak area of the collected infrared light at an infrared spectroscopy peak, in at least a portion of the range from about 1060 to about 1080 $cm^{-1}$.

Still another aspect of the invention is a method of treating an article with coatings or deposits. An article including a first surface can be provided. A coating or deposit of $SiO_x$, in which x can be from about 1.5 to about 2.9, can be applied directly or indirectly on the first surface. The coating or deposit of $SiO_x$ is generally from 2 to 1000 nm thick, optionally from 10 to 200 nm thick, optionally from 20 to 200 nm thick, and optionally from 20 to 30 nm thick. A coating of $SiO_xC_y$ or $SiN_xC_y$, where x can be from about 0.5 to about 2.4 and y can be from about 0.6 to about 3, can be applied over the coating or deposit of $SiO_x$. The coating or deposit of $SiO_x$, measured in the presence of the first surface and in the presence of the coating or deposit of $SiO_xC_y$ or $SiN_xC_y$, can be distinguished by a detectable response, such as an infrared spectroscopy peak in the wave number range from about 1060 to about 1080 $cm^{-1}$, indicative of a coating or deposit of $SiO_x$.

Another aspect of the invention is a method of detecting one or more coatings or deposits that are each simultaneously distinguishable through infrared spectroscopy.

For example, an article including a first surface can be provided. A coating or deposit of $SiO_xC_y$ or $SiN_xC_y$, where x can be from about 0.5 to about 2.4 and y can be from about 0.6 to about 3, can be applied on the first surface. A coating of $SiO_x$, in which x can be from about 1.5 to about 2.9, can be applied over the coating or deposit of $SiO_xC_y$ or $SiN_xC_y$. The coating or deposit of $SiO_x$, measured in the presence of the first surface and in the presence of the coating or deposit of $SiO_xC_y$ or $SiN_xC_y$, can be distinguished by a detectable response, such as an infrared spectroscopy peak in the wave number range from about 1060 to about 1080 $cm^{-1}$, indicative of a coating or deposit of $SiO_x$. At the same time, the coating or deposit of $SiO_xC_y$ or $SiN_xC_y$, measured in the presence of the first surface and in the presence of the coating or deposit of $SiO_x$, can be distinguished by a response in one or more of (a) at least a portion of a range between 950 and 1230 $cm^{-1}$ and (b) at least a portion of a range between 1230 and 1300 $cm^{-1}$, indicative of a coating or deposit of $SiO_xC_y$ or $SiN_xC_y$. For example, the coating or deposit of $SiO_xC_y$ or $SiN_xC_y$, measured in the presence of the first surface and in the presence of the coating or deposit of $SiO_x$, can be distinguished by a detectable infrared spectroscopy peak 234 in the wave number range of one or more of (a) at least a portion of a range from about 1015 to about 1035 $cm^{-1}$ and (b) at least a portion of a range from about 1245 to about 1270 $cm^{-1}$, each being indicative of a coating or deposit of $SiO_xC_y$ or $SiN_xC_y$.

As still another example, an article including a first surface can be provided. A coating or deposit of $SiO_x$, in which x can be from about 1.5 to about 2.9, can be applied directly or indirectly on the first surface. A coating of $SiO_xC_y$ or $SiN_xC_y$, where x can be from about 0.5 to about 2.4 and y can be from about 0.6 to about 3, can be applied over the coating or deposit of $SiO_x$. The coating of $SiO_xC_y$ or $SiN_xC_y$ is generally from 10 to 1000 nm thick, optionally from 50 to 500 nm thick, and optionally from 100 to 200 nm thick. The coating or deposit of $SiO_x$, measured in the presence of the first surface and in the presence of the coating or deposit of $SiO_xC_y$ or $SiN_xC_y$, can be distinguished by a detectable response, such as an infrared spectroscopy peak in the wave number range from about 1060 to about 1080 $cm^{-1}$, indicative of a coating or deposit of $SiO_x$. At the same time, the coating or deposit of $SiO_xC_y$ or $SiN_xC_y$, measured in the presence of the first surface and in the presence of the coating or deposit of $SiO_x$, can be distinguished by a response in one or more of (a) at least a portion of a range between 950 and 1230 $cm^{-1}$ and (b) at least a portion of a range between 1230 and 1300 $cm^{-1}$, indicative of a coating or deposit of $SiO_xC_y$ or $SiN_xC_y$. For example, the coating or deposit of $SiO_xC_y$ or $SiN_xC_y$, measured in the presence of the first surface and in the presence of the coating or deposit of $SiO_x$, can be distinguished by a detectable infrared spectroscopy peak in the wave number range of one or more of (a) at least a portion of a range from about 1015 to about 1035 $cm^{-1}$ and (b) at least a portion of a range from about 1245 to about 1270 $cm^{-1}$, each being indicative of a coating or deposit of $SiO_xC_y$ or $SiN_xC_y$.

Another aspect of the invention is a method of treating an article with coatings or deposits and rapidly and non-destructively detecting the presence of one or more of the coatings or deposits.

For example, an article including a first surface can be provided. A first coating of $SiO_xC_y$ or $SiN_xC_y$, where x is from about 0.5 to about 2.4 and y is from about 0.6 to about 3, can be applied on the first surface. The coating can then be detected by impinging infrared light having a wave number in one or more of (a) at least a portion of a range between 950 and 1230 $cm^{-1}$ and (b) at least a portion of a range between 1230 and 1300 $cm^{-1}$ onto at least a first surface being examined for the presence of a coating or deposit of $SiO_xC_y$ or $SiN_xC_y$; collecting at least a portion of the infrared light impinged on the first surface; and measuring the response output, which may include for example the maximum intensity and/or peak area of the collected infrared light at an infrared spectroscopy peak, in one or more of (a) at least a portion of a range between 950 and 1230 $cm^{-1}$ and (b) at least a portion of a range between 1230 and 1300 $cm^{-1}$, indicative of a coating or deposit of $SiO_xC_y$ or $SiN_xC_y$. For example, the coating or deposit of $SiO_xC_y$ or $SiN_xC_y$ can be distinguished by a detectable infrared spectroscopy peak in the wave number range of one or more of (a) at least a portion of a range from about 1015 to about 1035 $cm^{-1}$ and (b) at least a portion of a range from about 1245 to about 1270 $cm^{-1}$, each being indicative of a coating or deposit of $SiO_xC_y$ or $SiN_xC_y$.

Next, a second coating from 5 to 1000 nm thick of $SiO_x$, where x is from about 1.5 to about 2.9, can be applied over the first coating. And a third coating from 5 to 1000 nm thick of $SiO_xC_y$ or $SiN_xC_y$, where x is from about 0.5 to about 2.4 and y is from about 0.6 to about 3, can be applied over the coating of $SiO_x$. The second and third coatings can then be detected by impinging infrared light having a wave number in (a) at least a portion of a range from about 1060 to about 1080 $cm^{-1}$, and (b) one or more of (i) at least a portion of a range between 950 and 1230 $cm^{-1}$ and (ii) at least a portion of a range between 1230 and 1300 $cm^{-1}$ onto at least a first surface being examined for the presence of the second and the third coatings; collecting at least a portion of the infrared light impinged on the first surface; and measuring the response output, which may include for example the maximum intensity and/or peak area of the collected infrared light at an infrared spectroscopy peak in at least a portion of the range from about 1060 to about 1080 $cm^{-1}$, indicative of a coating or deposit of $SiO_x$; and at the same time measuring the response output, which may include for example the maximum intensity and/or peak area of the collected infrared light at an infrared spectroscopy peak, in one or more of (a) at least a portion of a range between 950 and 1230 $cm^{-1}$ and (b) at least a portion of a range between 1230 and 1300 $cm^{-1}$, indicative of a coating or deposit of $SiO_xC_y$ or $SiN_xC_y$, and optionally adjusting the measurement in order to account for the response output attributable to the first coating. For example, the coating or deposit of $SiO_xC_y$ or $SiN_xC_y$ can be distinguished by a detectable infrared spectroscopy peak in the wave number range of one or more of (a) at least a portion of a range from about 1015 to about 1035 $cm^{-1}$ and (b) at least a portion of a range from about 1245 to about 1270 $cm^{-1}$, each being indicative of a coating or deposit of $SiO_xC_y$ or $SiN_xC_y$.

As another example, an article including a first surface can be provided. A first coating of $SiO_xC_y$ or $SiN_xC_y$, where x is from about 0.5 to about 2.4 and y is from about 0.6 to about 3, can be applied on the first surface. Next, a second coating from 5 to 1000 nm thick of $SiO_x$, where x is from about 1.5 to about 2.9, can be applied over the first coating. The first and second coatings can then be detected by impinging infrared light having a wave number in (a) at least a portion of a range from about 1060 to about 1080 $cm^{-1}$, and (b) one or more of (i) at least a portion of a range between 950 and 1230 $cm^{-1}$ and (ii) at least a portion of a range between 1230 and 1300 $cm^{-1}$ onto at least a first surface being examined for the presence of the second and the third coatings; collecting at least a portion of the infrared light impinged on the first surface; and measuring the response output, which may include for example the maximum intensity and/or peak area of the collected infrared light at an infrared spectroscopy peak, in one or more of (a) at least a portion of a range between 950 and 1230 $cm^{-1}$ and (b) at least a portion of a range between 1230 and 1300 $cm^{-1}$, indicative of a coating or deposit of $SiO_xC_y$ or $SiN_xC_y$; and at the same time measuring the response output, which may include for example the maximum intensity and/or peak area of the collected infrared light at an infrared spectroscopy peak, in at least a portion of the range from about 1060 to about 1080 $cm^{-1}$, indicative of a coating or deposit of $SiO_x$. For example, the coating or deposit of $SiO_xC_y$ or $SiN_xC_y$ can be distinguished by a detectable infrared spectroscopy peak in the wave number range of one or more of (a) at least a portion of a range from about 1015 to about 1035 $cm^{-1}$ and (b) at least a portion of a range from about 1245 to about 1270 $cm^{-1}$, each being indicative of a coating or deposit of $SiO_xC_y$ or $SiN_xC_y$.

Next, a third coating of $SiO_xC_y$ or $SiN_xC_y$, where x is from about 0.5 to about 2.4 and y is from about 0.6 to about 3, can be applied over the coating of $SiO_x$. The third coating can then be detected by impinging infrared light having a wave number in one or more of (a) at least a portion of a range between 950 and 1230 $cm^{-1}$ and (b) at least a portion of a range between 1230 and 1300 $cm^{-1}$ onto at least a first surface being examined for the presence of a coating or deposit of $SiO_xC_y$ or $SiN_xC_y$; collecting at least a portion of the infrared light impinged on the first surface; and measuring the response output, which may include for example the maximum intensity and/or peak area of the collected infrared light at an infrared spectroscopy peak, in one or more of (a) at least a portion of a range between 950 and 1230 $cm^{-1}$ and (b) at least a portion of a range between 1230 and 1300 $cm^{-1}$, indicative of a coating or deposit of $SiO_xC_y$ or $SiN_xC_y$, and optionally adjusting the measurement in order to account for the response output attributable to the first coating. For example, the coating or deposit of $SiO_xC_y$ or $SiN_xC_y$ can be distinguished by a detectable infrared spectroscopy peak in the wave number range of one or more of (a) at least a portion of a range from about 1015 to about 1035 $cm^{-1}$ and (b) at least a portion of a range from about 1245 to about 1270 $cm^{-1}$, each being indicative of a coating or deposit of $SiO_xC_y$ or $SiN_xC_y$.

As another example, an article including a first surface can be provided. A first coating of $SiO_xC_y$ or $SiN_xC_y$, where x is from about 0.5 to about 2.4 and y is from about 0.6 to about 3, can be applied on the first surface. Next, a second coating of $SiO_x$, where x is from about 1.5 to about 2.9, can be applied over the first coating. Finally, a third coating of $SiO_xC_y$ or $SiN_xC_y$, where x is from about 0.5 to about 2.4 and y is from about 0.6 to about 3, can be applied over the coating of $SiO_x$.

Each of the first coating, the second coating, and the third coating can then simultaneously be detected by impinging infrared light having a wave number in (a) at least a portion of a range from about 1060 to about 1080 $cm^{-1}$, and (b) one or more of (i) at least a portion of a range between 950 and 1230 $cm^{-1}$ and (ii) at least a portion of a range between 1230 and 1300 $cm^{-1}$ onto at least a first surface being examined for the presence of the second and the third coatings; collecting at least a portion of the infrared light impinged on the first surface; measuring the response output, which may include for example the maximum intensity and/or peak area of the collected infrared light at an infrared spectroscopy peak, in at least a portion of the range from about 1060 to about 1080 $cm^{-1}$, indicative of a coating or deposit of $SiO_x$; and at the same time measuring the response output, which may include for example the maximum intensity and/or peak area of the collected infrared light at an infrared spectroscopy peak, in one or more of (a) at least a portion of a range between 950 and 1230 cm$^{-1}$ and (b) at least a portion of a range between 1230 and 1300 cm$^{-1}$, indicative of a coating or deposit of SiO$_x$C$_y$ or SiN$_x$C$_y$. For example, the coatings or deposits of SiO$_x$C$_y$ or SiN$_x$C$_y$ can be distinguished by a detectable infrared spectroscopy peak in the wave number range of one or more of (a) at least a portion of a range from about 1015 to about 1035 cm$^{-1}$ and (b) at least a portion of a range from about 1245 to about 1270 cm$^{-1}$, each being indicative of a coating or deposit of SiO$_x$C$_y$ or SiN$_x$C$_y$.

Even another aspect of the invention is a non-destructive method of detecting whether a coating or deposit of a mold lubricant is present on a surface of an article. To carry out this method, an infrared spectroscopy peak produced by the mold lubricant is selected. The selected peak has a wave number indicative of a coating or deposit such as of the mold lubricant. Infrared light having a wave number of the mold lubricant peak is impinged onto at least a first surface being examined for the presence of a mold lubricant. At least a portion of the infrared light impinged on the first surface is collected. The maximum intensity and/or peak area of the collected infrared light is measured at the wave number indicative of a coating or deposit of the mold lubricant.

Figure 1:
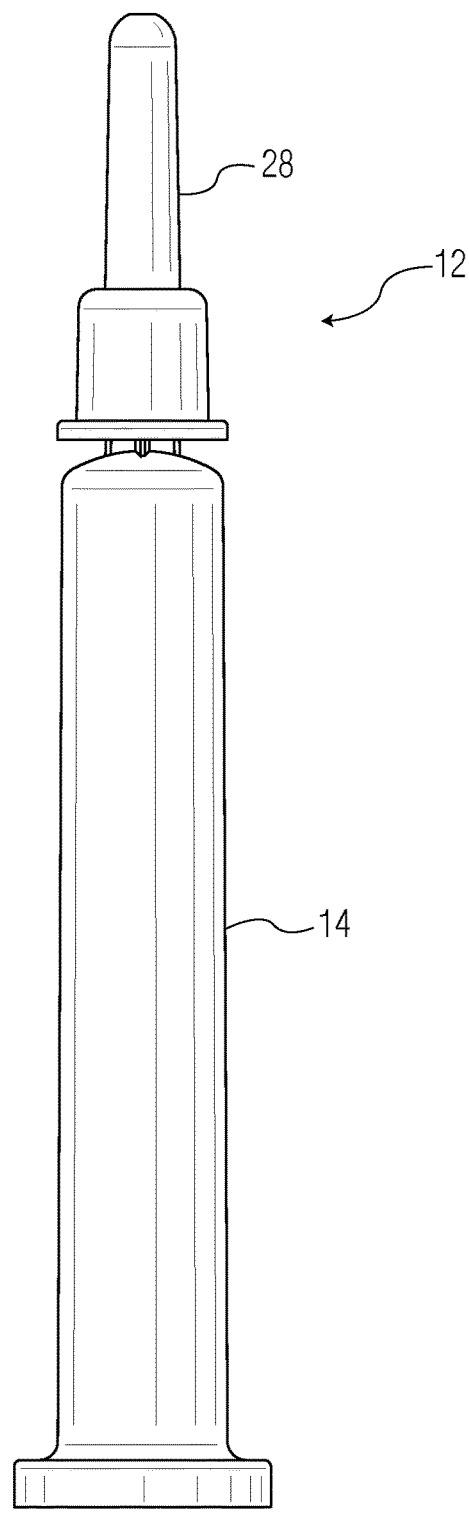
FIG. 1 is a side elevation of a syringe barrel and cap assembly.

The following reference characters may be used in the Figures:

| | |
|---|---|
| 12 | Capped pre-assembly |
| 14 | Barrel |
| 16 | Internal wall |
| 18 | Barrel lumen |
| 20 | Dispensing portion |
| 22 | Front opening |
| 24 | Distal opening |
| 26 | Dispensing portion lumen |
| 28 | Cap |
| 30 | (first) Vapor-deposited coating or layer |
| 32 | Opening |
| 34 | (second) vapor-deposited coating or layer |
| 36 | Plunger tip or piston |
| 38 | Plunger rod |
| 40 | Fluid composition |
| 42 | Rib |
| 44 | Cylindrical surface |
| 46 | Barb |
| 48 | Catch |
| 210 | Pharmaceutical package |
| 212 | Vial |
| 214 | Cartridge |
| 216 | Impinged infrared light |
| 218 | Source (of 216) |
| 220 | First surface |
| 222 | Collector |
| 224 | Collected infrared light |
| 226 | Surface |
| 228 | Reflected infrared light |
| 230 | Axis |
| 232 | Coating or deposit of mold lubricant |
| 234 | Spectroscopy peak |
| 236 | Light guide |
| 238 | Impinged position |
| 240 | Impinged position |
| 242 | Impinged position |
| 244 | Mirror |
| 246 | Prism |
| 248 | pH protective coating |
| 250 | Lubricity coating or layer |
| 252 | Partially silvered mirror |
| 260 | Uncoated syringe, set 1 |
| 262 | Tie layer and SiO$_x$ coated syringe, set 2 |
| 264 | Tie layer and SiO$_x$ coated syringe, set 3 |
| 268 | Vials 1-16 (no pH protection) |
| 270 | Vials 17-32 (2.5 sec pH protection) |
| 272 | Vials 33-48 (5 sec pH protection) |

-continued

| | |
|---|---|
| 274 | Vials 49-64 (10 sec pH protection) |
| 276 | Vials 65-80 (15 sec pH protection) |
| 278 | Vials 81-96 (20 sec pH protection) |
| 280 | Uncoated syringe |
| 282 | Tie layer coated syringe |
| 284 | Bilayer (tie and barrier) coated syringe |
| 286 | Trilayer (tie, barrier, and protective) coated syringe |
| 290 | Uncoated vial |
| 292 | Tie layer coated vial |
| 294 | Bilayer (tie and barrier) coated vial |
| 296 | Trilayer (tie, barrier, and protective) coated vial |
| 300 | Tie layer coated vial (2.5 sec) |
| 302 | Tie layer coated vial (5 sec) |
| 304 | Tie layer coated vial (10 sec) |
| 306 | Tie layer coated vial (15 sec) |
| 310 | Bilayer coated vial (2.5 sec barrier) |
| 312 | Bilayer coated vial (5 sec barrier) |
| 314 | Bilayer coated vial (10 sec barrier) |
| 316 | Bilayer coated vial (15 sec barrier) |
| 700 | Syringe |
| 702 | Needle |
| 704 | Land |

DEFINITION SECTION

In the context of the present invention, the following definitions and abbreviations are used:

In the present Figures, the capped pre-assembly 12 is configured as a syringe. The capped pre-assembly 12 can optionally be completed to form a syringe by adding a plunger tip or piston 36 (two interchangeable names for the same structure) and a plunger rod 38. The internal wall 16 can define at least a portion of the barrel 14. The plunger tip or piston 36 can be a relatively sliding part of the syringe, with respect to the barrel 14. The term "syringe," however, is broadly defined to include cartridges, injection "pens," and other types of barrels or reservoirs adapted to be assembled with one or more other components to provide a functional syringe. "Syringe" is also broadly defined to include related articles such as auto-injectors, which provide a mechanism for dispensing the contents.

RF is Radio Frequency.

The term "at least" in the context of the present invention means "equal or more" than the integer following the term. The word "comprising" does not exclude other elements or steps, and the indefinite article "a" or "an" does not exclude a plurality unless indicated otherwise. Whenever a parameter range is indicated, it is intended to disclose the parameter values given as limits of the range and all values of the parameter falling within said range.

"First" and "second" or similar references to, for example, coating or layers refer to the minimum number of coating or layers that are present, but do not necessarily represent the order or total number of coating or layers. These terms do not limit the number of coating or layers or the particular processing carried out at the respective stations.

Empirical compositions represented by the formulas $SiO_x$, $SiO_xC_y$, and $SiO_xC_yH_z$ are referred to in this specification. The values of x, y, and z used throughout this specification should be understood as ratios or an empirical formula (for example for a coating or layer), rather than as a limit on the number or type of atoms in a molecule. For example, octamethylcyclotetrasiloxane, which has the molecular composition $Si_4O_4C_8H_{24}$, can be described by the following empirical formula, arrived at by dividing each of w, x, y, and z in the molecular formula by 4, the largest common factor: $SiO_1C_2H_6$. The values of x, y, and z are also not limited to integers. For example, (acyclic) octamethyltrisiloxane, molecular composition $Si_3O_2C_8H_{24}$, is reducible to $SiO_{0.67}C_{2.67}H_8$. Also, although $SiO_xC_yH_z$ is described as equivalent to $SiO_xC_y$, it is not necessary to show the presence of hydrogen in any proportion to show the presence of $SiO_xC_y$.

A "protective coating or layer" according to the present invention is a coating or layer that protects an underlying surface, coating or layer from a fluid composition contacting the coating or layer. The present pH protective coating or layers optionally can have a composition according to the empirical composition $Si_wO_xC_yH_z$, (or its equivalent $SiO_xC_y$) as defined herein. It generally has an atomic ratio $Si_wO_xC_y$ (or its equivalent $SiO_xC_y$) wherein w is 1, x is from about 0.5 to about 2.4, y is from about 0.6 to about 3.

The formula $Si_wO_xC_y$ is an expression of the atomic ratio of Si, O, and C in the "protective coating or layer." The atomic ratio can be determined by XPS (X-ray photoelectron spectroscopy). Taking into account the H atoms, which are not measured by XPS, the same coating or layer may thus in one aspect have the formula $Si_wO_xC_yH_z$ (or its equivalent $SiO_xC_y$), for example where w is 1, x is from about 0.5 to about 2.4, y is from about 0.6 to about 3, and z is from about 2 to about 9.

"Slidably" means that the plunger tip or piston, closure, or other movable part is permitted to slide in a syringe barrel, cartridge, or other vessel.

The term "response output" in the context of the present invention is any characteristic or metric that may be measured or calculated from an infrared spectrum and used to indicate the presence and/or thickness of one or more coatings or deposits. For example, the response output may comprise the maximum intensity and/or peak area of the collected infrared light at an infrared spectroscopy peak at one or more wavenumbers or ranges of wavenumbers. Other metrics that are commonly used within Fourier transform infrared spectroscopy (FTIR) may also be relied on. Examples of other metrics include analysis of peak shift changes, slope measurement, curve fitting, first derivative calculations, inflection point determinations, and rhythmic or exponential conversions. Additionally, more than one metric may be used. For example, multiple metrics across a range of wavenumbers may provide a more precise indication of the presence and/or thickness of the coating or deposit.

The term "predetermined parameter" in the context of the present invention is any benchmark or reference standard that can be used to determine whether the desired coating or deposit is present and/or present at an acceptable thickness. For example, the response output may be compared against a benchmark that is derived from a comparison with an uncoated article. For instance, the response output might be compared against an uncoated article and subjected to differential scanning in order to determine whether the portion of the response output attributable to the coating or deposit meets a certain minimum threshold. As another example, the response output may be compared against a reference standard, such as one that may denote a chosen, e.g. minimum acceptable, thickness of the coating or deposit.

DETAILED DESCRIPTION

An aspect of the invention is a method to detect and measure a vapor-deposited coating or layer such as 30 of $SiO_xC_y$ applied to at least a portion of the internal wall 16 of the barrel 14 of a capped pre-assembly 12, a syringe barrel 14, the container of a pharmaceutical package 210, a vial 212, a cartridge 214, or other container. The method is exemplified here with respect to a capped pre-assembly 12 and a vial 212, but can equally be performed on other types of containers.

Referring to FIGS. 1-10 and 14, a capped pre-assembly 12 is provided comprising a barrel 14, optionally a dispensing portion 20, and a cap 28. The capped pre-assembly 12 can be a complete article or it can be a portion of a complete article adapted to dispense fluid, such as a syringe, a cartridge, a catheter, a vial, or other article.

The barrel 14 has an internal wall 16 defining a barrel lumen 18 and a front opening 22 through the internal wall 16. Optionally in any embodiment, the barrel 14 can further include another opening 32 spaced from the dispensing portion 20 and communicating through the internal wall 16. Such an opening is conventional, for example, in a syringe or cartridge, where a typical example is the back opening 32 of a prefilled syringe barrel, through which the piston or plunger 36 is inserted after the barrel lumen 18 is filled with a suitable pharmaceutical preparation or other fluid material 40 to be dispensed.

The barrel 14 is formed, for example, by molding, although the manner of its formation is not critical and it can also be formed, for example, by machining a solid preform. Preferably, the barrel is molded by injection molding thermoplastic material, although it can also be formed by blow molding or a combined method.

As one preferred example, the barrel 14 can be formed by placing a dispensing portion 20 as described below in an injection mold and injection molding thermoplastic material about the dispensing portion, thus forming the barrel and securing the dispensing portion to the barrel. Alternatively, the dispensing portion (if present) and the barrel can be molded or otherwise formed as a single piece, or can be formed separately and joined in other ways. The barrel of any embodiment can be made of any suitable material. Several barrel materials particularly contemplated are COC (cyclic olefin copolymer), COP (cyclic olefin polymer), PET (polyethylene terephthalate), and polypropylene.

The optional dispensing portion 20 of the capped pre-assembly 12 is provided to serve as an outlet for fluid dispensed from the barrel lumen 18 of a completed article made from the capped pre-assembly 12. One example of a suitable dispensing portion illustrated in the Figures is a hypodermic needle 20.

Alternatively, in any embodiment the dispensing portion 20 can instead be a needle-free dispenser. One example of a suitable needle-free dispenser is a blunt or flexible dispensing portion intended to be received in a complementary coupling to transfer fluid material 40. Such blunt or flexible dispensing portions are well known for use in syringes, intravenous infusion systems, and other systems and equipment to dispense material while avoiding the hazard of working with a sharp needle that may accidentally stick a health professional or other person. Another example of a needle-free dispenser is a fluid jet or spray injection system that injects a free jet or spray of fluid directly through a patient's skin, without the need for an intermediate needle. Any type of dispensing portion 20, whether a hypodermic needle or any form of needle-free dispenser, is contemplated for use according to any embodiment of the present invention.

The dispensing portion 20 is secured to the barrel 14 and includes a distal opening 24 and a dispensing portion lumen 26. The front opening 22 communicates with the barrel lumen 18. The distal opening 24 is located outside the barrel 14. The dispensing portion lumen 26 communicates between the front opening 22 and the distal opening 24 of the dispensing portion 20. In the illustrated embodiment, the distal opening 24 is at the sharpened tip of a hypodermic needle 20.

The cap 28 is secured to the barrel 14 and at least substantially isolates the front opening 22 and the distal opening 24 of the dispensing portion 20 from pressure conditions outside the cap 28. Optionally in any embodiment, the cap 28 sufficiently isolates portions of the assembly 12 to provide a sufficient bio-barrier to facilitate safe use of the capped pre-assembly 12 for transdermal injections.

Figure 2:
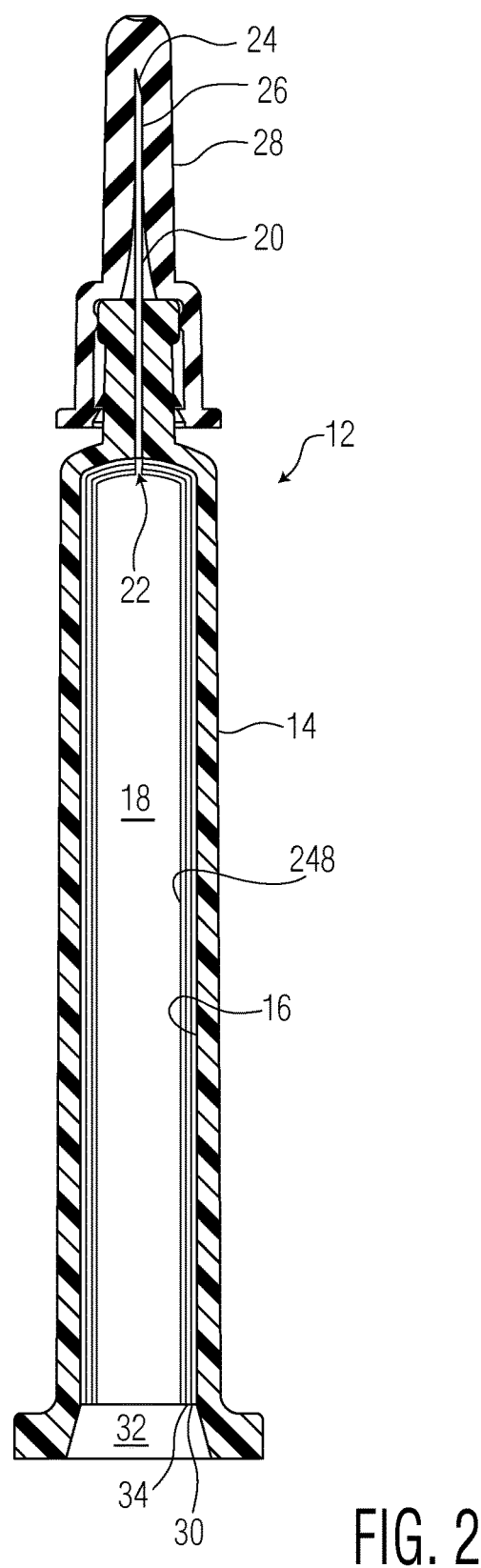
FIG. 2 is an axial section of the assembly of FIG. 1.

The cap 28 can isolate the distal opening 24 in various ways. Effective isolation can be provided at least partially due to contact between the cap 28 and the distal opening 24, as shown in present FIGS. 2 and 3. In the illustrated embodiment, the tip of the dispensing portion 20 is buried in the material of the cap 28. Alternatively in any embodiment, effective isolation can be provided at least partially due to contact between the cap 28 and the barrel 14, as also shown in present FIGS. 2 and 3. In the illustrated embodiment, the primary line of contact between the cap 28 and the barrel 14 is at a rib 42 (best seen in FIG. 3) encircling and seated against a generally cylindrical surface 44 at the nose of the barrel 14. Alternatively in any embodiment, effective isolation can be provided due to both of these types of contact as illustrated in FIGS. 2-3, or in other ways, without limitation.

Figure 3:
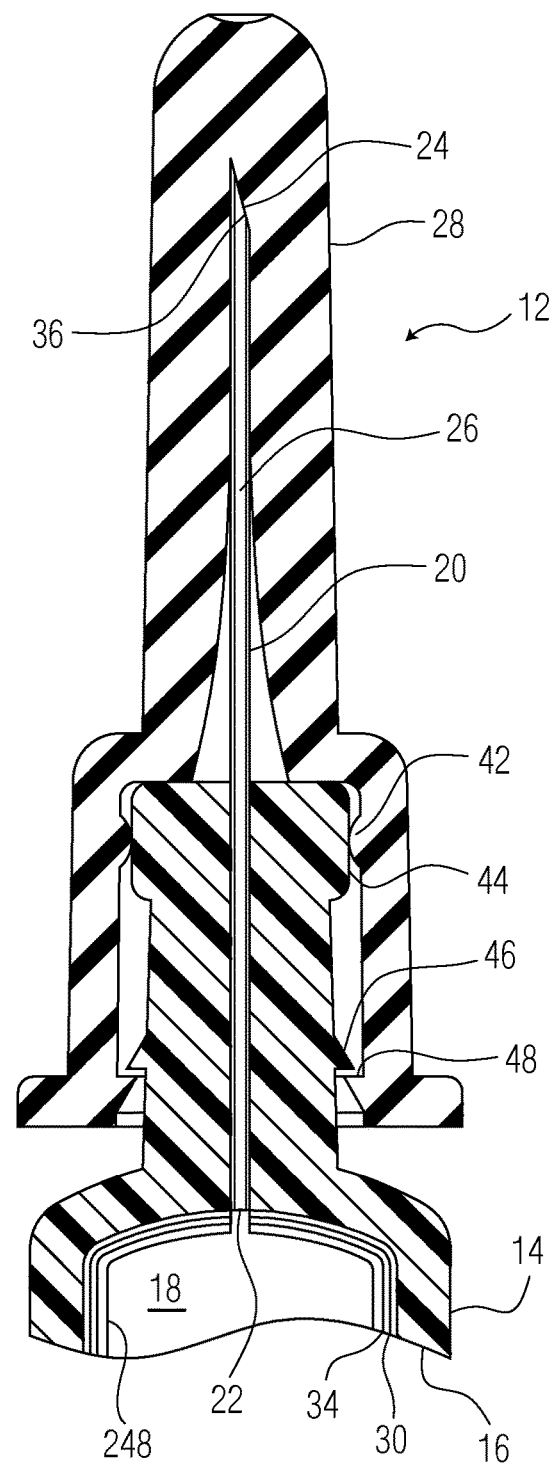
FIG. 3 is an enlarged detail view of FIG. 2.
Figure 4:
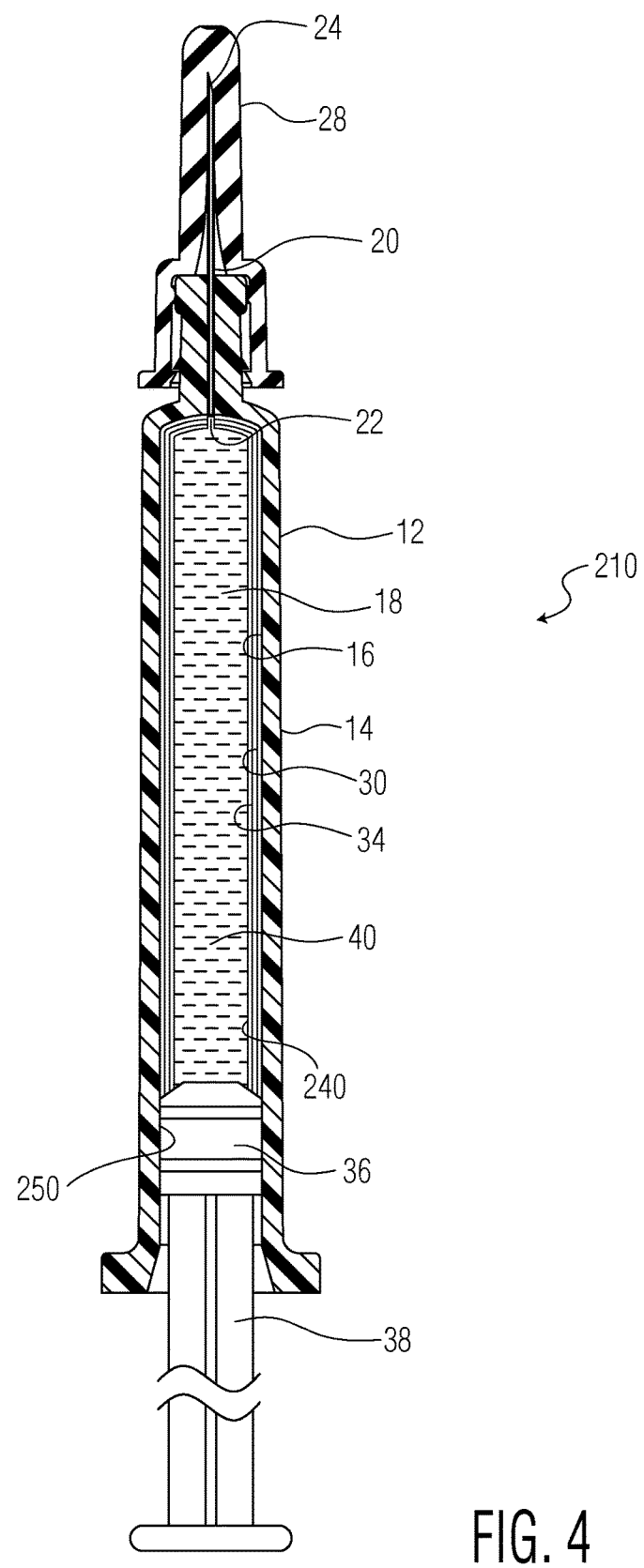
FIG. 4 is a view similar to FIG. 2 showing the assembly of FIG. 1 further assembled with fluid contents and a plunger to form a pharmaceutical package.

The cap 28 of any embodiment optionally has a latching mechanism, best shown in FIG. 3, including a barb 46 and a catch 48 which engage to hold the cap 28 in place. The catch 48 is made of sufficiently resilient material to allow the cap 28 to be removed and replaced easily.

If the dispensing portion 20 is a hypodermic needle, the cap 28 can be a specially formed needle shield. The original use of a needle shield is to cover the hypodermic needle before use, preventing accidental needle sticks and preventing contamination of the needle before it is injected in a patient or an injection port. A comparable cap preferably is used, even if the dispensing portion 20 is a needle-free dispenser, to prevent contamination of the dispenser during handling.

The cap 28 can be formed in any suitable way. For example, the cap 28 can be formed by molding thermoplastic material. Optionally in any embodiment, the thermoplastic material is elastomeric material or other material that is suitable for forming a seal. One suitable category of elastomeric materials is known generically as thermoplastic elastomer (TPE). An example of a suitable thermoplastic elastomer for making a cap 28 is Stelmi® Formulation 4800 (flexible cap formulation). Any other material having suitable characteristics can instead be used in any embodiment.

As another optional feature in any embodiment the cap 28 can be sufficiently permeable to a sterilizing gas to sterilize the portions of the assembly 12 isolated by the cap. One example of a suitable sterilizing gas is ethylene oxide. Caps 28 are available that are sufficiently permeable to the sterilizing gas that parts isolated by the cap can nonetheless be sterilized. An example of a cap formulation sufficiently permeable to accommodate ethylene oxide gas sterilization is Stelmi® Formulation 4800.

In the illustrated embodiment, the coatings such as 30, 34, and 248 are vapor-deposited coatings or layers applied directly or indirectly to at least a portion of the internal wall 16 of the barrel 14 while the pre-assembly 12 is capped. The coating or layer 30 is applied under conditions effective to maintain communication between the barrel lumen 18 and the dispensing portion lumen 26 via the front opening 22 at the end of the applying step.

The vapor deposited coating or layer for any embodiment defined in this specification (unless otherwise specified in a particular instance) optionally can be a coating or layer, optionally applied by PECVD as indicated in U.S. Pat. No. 7,985,188.

An aspect of the invention is a non-destructive method of detecting whether a coating or deposit such as 30 and/or 248 of $SiO_xC_y$ or $SiN_xC_y$, where x can be from about 0.5 to about 2.4 and y can be from about 0.6 to about 3, is present on or near a surface, for example 44 or 220, of an article, for example the capped syringe pre-assembly 12, syringe barrel 14, pharmaceutical package 210, vial 212, or cartridge 214. The method includes impinging, collecting, and measuring steps.

None of the steps recited in this specification and the accompanying claims represents a step plus function limitation.

The impinging step includes impinging infrared light 216 having a wave number in at least a portion of the range between 1230 and 1300 $cm^{-1}$, such as for example from about 1245 to about 1270 $cm^{-1}$, for example from a source 218, onto at least a first surface 44 or 220 being examined for the presence of a coating or deposit such as 30 and/or 248 of $SiO_xC_y$ or $SiN_xC_y$.

The collecting step includes collecting at least a portion 224 of the infrared light 216 impinged on the first surface 44 or 220, as with a collector 222.

The measuring step includes measuring response output, which may include for example the maximum intensity and/or peak area of the collected infrared light 224 at an infrared spectroscopy peak 234, in at least a portion of the range between 1230 and 1300 $cm^{-1}$, such as for example from about 1245 to about 1270 $cm^{-1}$. A spectroscopy peak 234 indicative of a coating or deposit such as 30 and/or 248 of $SiO_xC_y$ or $SiN_xC_y$ means that the peak 234, if found in the collected infrared light 224, indicates that a coating or deposit such as 30 and/or 248 of $SiO_xC_y$ or $SiN_xC_y$ is present on a surface 44 or 220 impinged with the infrared light 216.

The impinging step may also include impinging infrared light 216 having a wave number in at least a portion of the range between 950 and 1230 $cm^{-1}$, such as for example from about 1015 to about 1035 $cm^{-1}$, for example from a source 218, onto at least a first surface 44 or 220 being examined for the presence of a coating or deposit such as 30 and/or 248 of $SiO_xC_y$ or $SiN_xC_y$.

And the measuring step may include measuring the response output, which may include for example the maximum intensity and/or peak area of the collected infrared light 224 at an infrared spectroscopy peak 234, in at least a portion of the range between 950 and 1230 $cm^{-1}$, such as for example from about 1015 to about 1035 $cm^{-1}$. A spectroscopy peak 234 indicative of a coating or deposit such as 30 and/or 248 of $SiO_xC_y$ or $SiN_xC_y$ means that the peak 234, if found in the collected infrared light 224, indicates that a coating or deposit such as 30 and/or 248 of $SiO_xC_y$ or $SiN_xC_y$ is present on a surface 44 or 220 impinged with the infrared light 216.

Because the absorption in at least a portion of the range between 950 and 1230 $cm^{-1}$, such as from about 1015 to about 1035 $cm^{-1}$, may be of a higher intensity than the absorption in at least a portion of the range between 1230 and 1300 $cm^{-1}$, such as from about 1245 to about 1270 $cm^{-1}$, the measurement of the response output, which may include for example the maximum intensity and/or peak area of the collected infrared light 224 at an infrared spectroscopy peak, in at least a portion of the range between 950 and 1230 $cm^{-1}$, such as from about 1015 to about 1035 $cm^{-1}$, may provide a more robust measurement.

As another alternative, the impinging step may include impinging infrared light 216 having a wave number in both (a) at least a portion of a range between 950 and 1230 $cm^{-1}$, such as from about 1015 to about 1035 $cm^{-1}$, and (b) at least a portion of a range between 1230 and 1300 $cm^{-1}$, such as from about 1245 to about 1270 $cm^{-1}$, for example from a source 218, onto at least a first surface 44 or 220 being examined for the presence of a coating or deposit such as 30 and/or 248 of $SiO_xC_y$ or $SiN_xC_y$. And the measuring step may therefore include measuring the response output, which may include for example the maximum intensity and/or peak area of the collected infrared light 224 at infrared spectroscopy peaks 234, in both (a) at least a portion of a range between 950 and 1230 $cm^{-1}$, such as from about 1015 to about 1035 $cm^{-1}$ and (b) at least a portion of a range between 1230 and 1300 $cm^{-1}$, such as from about 1245 to about 1270 $cm^{-1}$.

Another aspect of the invention is a non-destructive method of detecting whether a coating or deposit such as 34 of $SiO_x$, where x is from about 1.5 to about 2.9, is present on or near a surface, for example 44 or 220, of an article, for example the capped syringe pre-assembly 12, syringe barrel 14, pharmaceutical package 210, vial 212, or cartridge 214. The method includes impinging, collecting, and measuring steps.

The impinging step includes impinging infrared light 216 having a wave number in at least a portion of the range from about 1060 to about 1080 $cm^{-1}$, for example from a source 218, onto at least a first surface 44 or 220 being examined for the presence of a coating or deposit such as 34 of $SiO_x$.

The collecting step includes collecting at least a portion 224 of the infrared light 216 impinged on the first surface 44 or 220, as with a collector 222.

The measuring step includes measuring the response output, which may include for example the maximum intensity and/or peak area of the collected infrared light 224 at an infrared spectroscopy peak 234, in at least a portion of the range from about 1060 to about 1080 $cm^{-1}$. A spectroscopy peak 234 indicative of a coating or deposit such as 34 of $SiO_x$ means that the peak 234, if found in the collected infrared light 224, indicates that a coating or deposit such as 34 of $SiO_x$ is present on a surface 44 or 220 impinged with the infrared light 216.

The present method can be used, for example, for characterization of plasma coatings on plastic molded articles utilizing a fast, non-destructive, and coating specific method. These measurement attributes permit 100 percent online inspection of coated molded plastic devices, otherwise only possible with slow, offline, destructive analytical methods.

Another aspect of the invention is an article such as 12, 14, 210, 212, or 214 which can include or be a prefilled container, such as a pharmaceutical package 210, containing a fluid composition 40. The container, for example the capped pre-assembly 12, syringe barrel 14, pharmaceutical package 210, vial 212, and/or cartridge 214, has at least a first surface 44 or 220 including at least one direct or indirect coating or deposit such as 30 and/or 248 of $SiO_xC_y$ or $SiN_xC_y$, where x can be from about 0.5 to about 2.4 and y can be from about 0.6 to about 3. The coating or deposit such as 30 and/or 248 of $SiO_xC_y$ or $SiN_xC_y$ has a response output in the wave number range between 1230 and 1300 $cm^{-1}$, such as a detectable infrared spectroscopy peak 234 in the wave number range from about 1245 to about 1270 cm$^{-1}$, indicative of a coating or deposit such as 30 and/or 248 of SiO$_x$C$_y$ or SiN$_x$C$_y$.

Similarly, another aspect of the invention is an article such as 12, 14, 210, 212, or 214 which can include or be a prefilled container, such as a pharmaceutical package 210, containing a fluid composition 40. The container, for example the capped pre-assembly 12, syringe barrel 14, pharmaceutical package 210, vial 212, and/or cartridge 214, has at least a first surface 44 or 220 including at least one direct or indirect coating or deposit such as 30 and/or 248 of SiO$_x$C$_y$ or SiN$_x$C$_y$, where x can be from about 0.5 to about 2.4 and y can be from about 0.6 to about 3. The coating or deposit such as 30 and/or 248 of SiO$_x$C$_y$ or SiN$_x$C$_y$ has a response output in the wave number range between 950 and 1230 cm$^{-1}$, such as a detectable infrared spectroscopy peak 234 in the wave number range from about 1015 to about 1035 cm$^{-1}$, indicative of a coating or deposit such as 30 and/or 248 of SiO$_x$C$_y$ or SiN$_x$C$_y$.

Another aspect of the invention is an article such as 12, 14, 210, 212, or 214 which can include or be a prefilled container, such as a pharmaceutical package 210, containing a fluid composition 40. The container, for example the capped pre-assembly 12, syringe barrel 14, pharmaceutical package 210, vial 212, and/or cartridge 214, has at least a first surface 44 or 220 including at least one direct or indirect coating or deposit such as 34 of SiO$_x$, where x is from about 1.5 to about 2.9. The coating or deposit such as 34 of SiO$_x$ has a response output, such as a detectable infrared spectroscopy peak 234, in the wave number range from about 1060 to about 1080 cm$^{-1}$, indicative of a coating or deposit such as 34 of SiO$_x$.

Still another aspect of the invention is a method of treating an article such as 12, 14, 210, 212, or 214 with coatings or deposits such as 30 and/or 248 or 232. An article such as 12, 14, 210, 212, or 214 including a first surface 44 or 220 can be provided. A coating or deposit such as 30 and/or 248 of SiO$_x$C$_y$ or SiN$_x$C$_y$, where x can be from about 0.5 to about 2.4 and y can be from about 0.6 to about 3, can be applied on the first surface 44 or 220. A coating 34 of SiO$_x$, in which x can be from about 1.5 to about 2.9, can be applied over the coating or deposit such as 30 of SiO$_x$C$_y$ or SiN$_x$C$_y$. The coating or deposit such as 30 and/or 248 of SiO$_x$C$_y$ or SiN$_x$C$_y$, measured in the presence of the first surface 44 or 220 and in the presence of the coating or deposit such as 34 of SiO$_x$, can be distinguished by the response output in the wave number range between 1230 and 1300 cm$^{-1}$, such as for example a detectable infrared spectroscopy peak 234 in the wave number range from about 1245 to about 1270 cm$^{-1}$, indicative of a coating or deposit such as 30 and/or 248 of SiO$_x$C$_y$ or SiN$_x$C$_y$.

Similarly, another aspect of the invention is a method of treating an article such as 12, 14, 210, 212, or 214 with coatings or deposits such as 30 and/or 248 or 232. An article such as 12, 14, 210, 212, or 214 including a first surface 44 or 220 can be provided. A coating or deposit such as 30 and/or 248 of SiO$_x$C$_y$ or SiN$_x$C$_y$, where x can be from about 0.5 to about 2.4 and y can be from about 0.6 to about 3, can be applied on the first surface 44 or 220. A coating 34 of SiO$_x$, in which x can be from about 1.5 to about 2.9, can be applied over the coating or deposit such as 30 of SiO$_x$C$_y$ or SiN$_x$C$_y$. The coating or deposit such as 30 and/or 248 of SiO$_x$C$_y$ or SiN$_x$C$_y$, measured in the presence of the first surface 44 or 220 and in the presence of the coating or deposit such as 34 of SiO$_x$, can be distinguished by the response output in the wave number range between 950 and 1230 cm$^{-1}$, such as for example a detectable infrared spectroscopy peak 234 in the wave number range from about 1015 to about 1035 cm$^{-1}$, indicative of a coating or deposit such as 30 and/or 248 of SiO$_x$C$_y$ or SiN$_x$C$_y$.

As an alternative, another aspect of the invention is a method of treating an article such as 12, 14, 210, 212, or 214 with coatings or deposits such as 30 and/or 248 or 232. An article such as 12, 14, 210, 212, or 214 including a first surface 44 or 220 can be provided. A coating or deposit such as 30 and/or 248 of SiO$_x$C$_y$ or SiN$_x$C$_y$, where x can be from about 0.5 to about 2.4 and y can be from about 0.6 to about 3, can be applied on the first surface 44 or 220. A coating 34 of SiO$_x$, in which x can be from about 1.5 to about 2.9, can be applied over the coating or deposit such as 30 of SiO$_x$C$_y$ or SiN$_x$C$_y$. The coating or deposit such as 30 and/or 248 of SiO$_x$C$_y$ or SiN$_x$C$_y$, measured in the presence of the first surface 44 or 220 and in the presence of the coating or deposit such as 34 of SiO$_x$, can be distinguished by the response output, which may include for example a detectable infrared spectroscopy peak 234 in the wave number range of one or more of (a) at least a portion of a range between 950 and 1230 cm$^{-1}$, such as from about 1015 to about 1035 cm$^{-1}$, and (b) at least a portion of a range between 1230 and 1300, such as from about 1245 to about 1270 cm$^{-1}$, indicative of a coating or deposit such as 30 and/or 248 of SiO$_x$C$_y$ or SiN$_x$C$_y$.

Another aspect of the invention is a method of treating an article such as 12, 14, 210, 212, or 214 with coatings or deposits such as 30 and/or 248 or 232. An article such as 12, 14, 210, 212, or 214 including a first surface 44 or 220 can be provided. A coating or deposit such as 30 and/or 248 of SiO$_x$C$_y$ or SiN$_x$C$_y$, where x can be from about 0.5 to about 2.4 and y can be from about 0.6 to about 3, can be applied on the first surface 44 or 220. A coating 34 of SiO$_x$, in which x can be from about 1.5 to about 2.9, can be applied over the coating or deposit such as 30 of SiO$_x$C$_y$ or SiN$_x$C$_y$. The coating 34 of SiO$_x$, measured in the presence of the first surface 44 or 220 and in the presence of the coating or deposit such as 30 and/or 248 of SiO$_x$C$_y$ or SiN$_x$C$_y$, can be distinguished by a response output, which may include for example a detectable infrared spectroscopy peak 234, in the wave number range from about 1060 to about 1080 cm$^{-1}$, indicative of a coating 34 of SiO$_x$.

Another aspect of the invention is a method of treating an article such as 12, 14, 210, 212, or 214 with coatings or deposits such as 30, 34, and/or 248 or 232. An article such as 12, 14, 210, 212, or 214 including a first surface 44 or 220 can be provided. A coating or deposit such as 30 and/or 248 of SiO$_x$C$_y$ or SiN$_x$C$_y$, where x can be from about 0.5 to about 2.4 and y can be from about 0.6 to about 3, can be applied on the first surface 44 or 220. A coating 34 of SiO$_x$, in which x can be from about 1.5 to about 2.9, can be applied over the coating or deposit such as 30 of SiO$_x$C$_y$ or SiN$_x$C$_y$. The coating or deposit such as 30 and/or 248 of SiO$_x$C$_y$ or SiN$_x$C$_y$, measured in the presence of the first surface 44 or 220 and in the presence of the coating or deposit such as 34 of SiO$_x$, can be distinguished by a response output, which may include for example a detectable infrared spectroscopy peak 234 in the wave number range of one or more of (a) at least a portion of a range between 950 and 1230 cm$^{-1}$, such as from about 1015 to about 1035 cm$^{-1}$, and (b) at least a portion of a range between 1230 and 1300 cm$^{-1}$, such as from about 1245 to about 1270 cm$^{-1}$, indicative of a coating or deposit such as 30 and/or 248 of SiO$_x$C$_y$ or SiN$_x$C$_y$. At the same time, the coating 34 of SiO$_x$, measured in the presence of the first surface 44 or 220 and in the presence of the coating or deposit such as 30 and/or 248 of SiO$_x$C$_y$ or SiN$_x$C$_y$, can be distinguished by a response output, which may include for example a detectable infrared spectroscopy peak 234, in the wave number range from about 1060 to about 1080 cm$^{-1}$, indicative of a coating 34 of SiO$_x$.

Another aspect of the invention is a method of treating an article such as 12, 14, 210, 212, or 214 with coatings or deposits such as 30, 34, 248, or 232. An article such as 12, 14, 210, 212, or 214 including a first surface 44 or 220 can be provided. A coating 34 of SiO$_x$, in which x can be from about 1.5 to about 2.9, can be applied directly or indirectly on the first surface 44 or 220. A coating or deposit such as 248 of SiO$_x$C$_y$ or SiN$_x$C$_y$, where x can be from about 0.5 to about 2.4 and y can be from about 0.6 to about 3, can be applied over the coating 34. The coating or deposit such as 30 and/or 248 of SiO$_x$C$_y$ or SiN$_x$C$_y$, measured in the presence of the first surface 44 or 220 and in the presence of the coating or deposit such as 34 of SiO$_x$, can be distinguished by a response output, which may include for example a detectable infrared spectroscopy peak 234, in the wave number range of one or more of (a) at least a portion of a range between 950 and 1230 cm$^{-1}$, such as from about 1015 to about 1035 cm$^{-1}$, and (b) at least a portion of a range between 1230 and 1300 cm$^{-1}$, such as from about 1245 to about 1270 cm$^{-1}$, indicative of a coating or deposit such as 30 and/or 248 of SiO$_x$C$_y$ or SiN$_x$C$_y$. At the same time, the coating 34 of SiO$_x$, measured in the presence of the first surface 44 or 220 and in the presence of the coating or deposit such as 30 and/or 248 of SiO$_x$C$_y$ or SiN$_x$C$_y$, can be distinguished by a response output, which may include for example a detectable infrared spectroscopy peak 234, in the wave number range from about 1060 to about 1080 cm$^{-1}$, indicative of a coating 34 of SiO$_x$.

Another aspect of the invention is a method of treating an article such as 12, 14, 210, 212, or 214 with coatings or deposits such as 30, 34, and/or 248. An article such as 12, 14, 210, 212, or 214 including a first surface 44 or 220 can be provided. A coating or deposit such as 30 of SiO$_x$C$_y$ or SiN$_x$C$_y$, where x can be from about 0.5 to about 2.4 and y can be from about 0.6 to about 3, can be applied on the first surface 44 or 220. The presence of the first coating 30 can then be detected by impinging infrared light having a wave number in one or more of (a) at least a portion of a range between 950 and 1230 cm$^{-1}$, such as from about 1015 to about 1035 cm$^{-1}$, and (b) at least a portion of a range between 1230 and 1300 cm$^{-1}$, such as from about 1245 to about 1270 cm$^{-1}$, onto at least a first surface being examined for the presence of a coating or deposit of SiO$_x$C$_y$ or SiN$_x$C$_y$; collecting at least a portion of the infrared light impinged on the first surface; and measuring the response output, which may include for example the maximum intensity and/or peak area of the collected infrared light at an infrared spectroscopy peak, in one or more of (a) at least a portion of a range between 950 and 1230 cm$^{-1}$, such as from about 1015 to about 1035 cm$^{-1}$ and (b) at least a portion of a range between 1230 and 1300, such as from about 1245 to about 1270 cm$^{-1}$, indicative of a coating or deposit of SiO$_x$C$_y$ or SiN$_x$C$_y$, such as coating 30.

A second coating, such as coating 34, of SiO$_x$, where x is from about 1.5 to about 2.9, may be applied over the first coating 30. Next, a third coating, such as coating 248, of SiO$_x$C$_y$ or SiN$_x$C$_y$, where x is from about 0.5 to about 2.4 and y is from about 0.6 to about 3, may be applied over the coating 34 of SiO$_x$.

The presence of the second coating 34 and the third coating 248 may then be detected by impinging infrared light having a wave number in at least a portion of a range from about 1060 to about 1080 cm$^{-1}$, and (b) one or more of (i) at least a portion of a range between 950 and 1230 cm$^{-1}$, such as from about 1015 to about 1035 cm$^{-1}$, and (ii) at least a portion of a range between 1230 and 1300 cm$^{-1}$, such as from about 1245 to about 1270 cm$^{-1}$, onto at least a first surface being examined for the presence of the second and the third coatings; collecting at least a portion of the infrared light impinged on the first surface; measuring the response output, which may include for example the maximum intensity and/or peak area of the collected infrared light at an infrared spectroscopy peak, in at least a portion of the range from about 1060 to about 1080 cm$^{-1}$, indicative of a coating or deposit of SiO$_x$; and measuring the response output, which may include for example the maximum intensity and/or peak area of the collected infrared light at an infrared spectroscopy peak, in one or more of (a) at least a portion of a range between 950 and 1230 cm$^{-1}$, such as from about 1015 to about 1035 cm$^{-1}$, and (b) at least a portion of a range between 1230 and 1300 cm$^{-1}$, such as from about 1245 to about 1270 cm$^{-1}$, indicative of a coating or deposit of SiO$_x$C$_y$ or SiN$_x$C$_y$, and optionally adjusting the measurement in order to account for the portion of the response output attributable to the first coating.

Another aspect of the invention is a method of treating an article such as 12, 14, 210, 212, or 214 with coatings or deposits such as 30, 34, and/or 248. An article such as 12, 14, 210, 212, or 214 including a first surface 44 or 220 can be provided. A coating or deposit such as 30 of SiO$_x$C$_y$ or SiN$_x$C$_y$, where x can be from about 0.5 to about 2.4 and y can be from about 0.6 to about 3, can be applied on the first surface 44 or 220. A second coating, such as coating 34, of SiO$_x$, where x is from about 1.5 to about 2.9, may be applied over the first coating 30.

The presence of the first coating 30 and the second coating 34 may then be detected by impinging infrared light having a wave number in (a) at least a portion of a range from about 1060 to about 1080 cm$^{-1}$, and (b) one or more of (i) at least a portion of a range between 950 and 1230 cm$^{-1}$, such as from about 1015 to about 1035 cm$^{-1}$, and (ii) at least a portion of a range between 1230 and 1300 cm$^{-1}$, such as from about 1245 to about 1270 cm$^{-1}$, onto at least a first surface being examined for the presence of the second and the third coatings; collecting at least a portion of the infrared light impinged on the first surface; measuring the response output, which may include for example the maximum intensity and/or peak area of the collected infrared light at an infrared spectroscopy peak, in one or more of (a) at least a portion of a range between 950 and 1230 cm$^{-1}$, such as from about 1015 to about 1035 cm$^{-1}$, and (b) at least a portion of a range between 1230 and 1300, such as from about 1245 to about 1270 cm$^{-1}$, indicative of a coating or deposit of SiO$_x$C$_y$ or SiN$_x$C$_y$; and measuring the response output, which may include for example the maximum intensity and/or peak area of the collected infrared light at an infrared spectroscopy peak, in at least a portion of the range from about 1060 to about 1080 cm$^{-1}$, indicative of a coating or deposit of SiO$_x$.

Next, a third coating, such as coating 248, of SiO$_x$C$_y$ or SiN$_x$C$_y$, where x is from about 0.5 to about 2.4 and y is from about 0.6 to about 3, may be applied over the coating 34 of SiO$_x$. The presence of the third coating 248 may then be detected by impinging infrared light having a wave number in one or more of (a) at least a portion of a range between 950 and 1230 cm$^{-1}$, such as from about 1015 to about 1035 cm$^{-1}$, and (b) at least a portion of a range between 1230 and 1300 cm$^{-1}$, such as from about 1245 to about 1270 cm$^{-1}$, onto at least a first surface being examined for the presence of a coating or deposit of SiO$_x$C$_y$ or SiN$_x$C$_y$; collecting at least a portion of the infrared light impinged on the first surface; and measuring the response output, which may include for example the maximum intensity and/or peak area of the collected infrared light at an infrared spectroscopy peak, in one or more of (a) at least a portion of a range between 950 and 1230 cm$^{-1}$, such as from about 1015 to about 1035 cm$^{-1}$, and (b) at least a portion of a range between 1230 and 1300 cm$^{-1}$, such as from about 1245 to about 1270 cm$^{-1}$, indicative of a coating or deposit of SiO$_x$C$_y$ or SiN$_x$C$_y$, and optionally adjusting the measurement in order to account for a portion of the response output attributable to the first coating.

Another aspect of the invention is a method of treating an article such as 12, 14, 210, 212, or 214 with coatings or deposits such as 30, 34, and/or 248. An article such as 12, 14, 210, 212, or 214 including a first surface 44 or 220 can be provided. A coating or deposit such as 30 of SiO$_x$C$_y$ or SiN$_x$C$_y$, where x can be from about 0.5 to about 2.4 and y can be from about 0.6 to about 3, can be applied on the first surface 44 or 220.

A second coating, such as coating 34, of SiO$_x$, where x is from about 1.5 to about 2.9, may be applied over the first coating 30. Next, a third coating, such as coating 248, of SiO$_x$C$_y$ or SiN$_x$C$_y$, where x is from about 0.5 to about 2.4 and y is from about 0.6 to about 3, may be applied over the coating 34 of SiO$_x$.

The presence of the first coating 30, the second coating 34, and the third coating 248 may then be detected by impinging infrared light having a wave number in at least a portion of a range from about 1060 to about 1080 cm$^{-1}$, and (b) one or more of (i) at least a portion of a range between 950 and 1230 cm$^{-1}$, such as from about 1015 to about 1035 cm$^{-1}$, and (ii) at least a portion of a range between 1230 and 1300 cm$^{-1}$, such as from about 1245 to about 1270 cm$^{-1}$, onto at least a first surface being examined for the presence of the first, second, and third coatings; collecting at least a portion of the infrared light impinged on the first surface; measuring the response output, which may include for example the maximum intensity and/or peak area of the collected infrared light at an infrared spectroscopy peak, in at least a portion of the range from about 1060 to about 1080 cm$^{-1}$, indicative of a coating or deposit of SiO$_x$; and measuring the response output, which may include for example the maximum intensity and/or peak area of the collected infrared light at an infrared spectroscopy peak, in one or more of (a) at least a portion of a range between 950 and 1230 cm$^{-1}$, such as from about 1015 to about 1035 cm$^{-1}$ and (b) at least a portion of a range between 1230 and 1300 cm$^{-1}$, such as from about 1245 to about 1270 cm$^{-1}$, indicative of a coating or deposit of SiO$_x$C$_y$ or SiN$_x$C$_y$.

Another aspect of the invention is a method of treating an article such as 12, 14, 210, 212, or 214 with coatings or deposits such as 30, 34, and/or 248. An article such as 12, 14, 210, 212, or 214 including a first surface 44 or 220 can be provided. A coating or deposit such as 30 of SiO$_x$C$_y$ or SiN$_x$C$_y$, where x can be from about 0.5 to about 2.4 and y can be from about 0.6 to about 3, can be applied on the first surface 44 or 220. A second coating, such as coating 34, from 5 to 1000 nm thick of SiO$_x$, where x is from about 1.5 to about 2.9, may be applied over the first coating 30.

The presence of the first coating 30 and the second coating 34 may then be detected by impinging infrared light having a wave number in (a) at least a portion of a range from about 1060 to about 1080 cm$^{-1}$, and (b) one or more of (i) at least a portion of a range between 950 and 1230 cm$^{-1}$, such as from about 1015 to about 1035 cm$^{-1}$, and (ii) at least a portion of a range between 1230 and 1300 cm$^{-1}$, such as from about 1245 to about 1270 cm$^{-1}$, onto at least a first surface being examined for the presence of the second and the third coatings; collecting at least a portion of the infrared light impinged on the first surface; measuring the response output, such as may include for example the maximum intensity and/or peak area of the collected infrared light at an infrared spectroscopy peak, in one or more of (a) at least a portion of a range between 950 and 1230 cm$^{-1}$, such as from about 1015 to about 1035 cm$^{-1}$, and (b) at least a portion of a range between 1230 and 1300 cm$^{-1}$, such as from about 1245 to about 1270 cm$^{-1}$, indicative of a coating or deposit of SiO$_x$C$_y$ or SiN$_x$C$_y$; and measuring the output response, such as may include for example the maximum intensity and/or peak area of the collected infrared light at an infrared spectroscopy peak, in at least a portion of the range from about 1060 to about 1080 cm$^{-1}$, indicative of a coating or deposit of SiO$_x$.

Even another aspect of the invention is a non-destructive method of detecting whether a coating or deposit such as 232 of a mold lubricant 232 is present on a surface 44 or 220 or 226 of an article such as 12, 14, 210, 212, or 214. To carry out this method, an infrared spectroscopy peak 234 produced by the mold lubricant 232 is selected. The selected peak 234 has a wave number indicative of a coating or deposit such as 232 of the mold lubricant 232. Infrared light 216 having a wave number of the mold lubricant peak 234 is impinged onto at least a first surface 226 being examined for the presence of a mold lubricant 232. At least a portion 224 of the infrared light 216 impinged on the first surface is collected. The maximum intensity and/or peak area of the collected infrared light 224 is measured at the wave number indicative of a coating or deposit such as 232 of the mold lubricant.

Optionally in any embodiment, the article such as 12, 14, 210, 212, or 214 can include a lumen 18.

Optionally in any embodiment, the first surface 44 or 220 can include or be an interior surface defining at least a portion of the lumen 18.

Optionally in any embodiment, the first surface can include or be an exterior surface 226 of the article such as 12, 14, 210, 212, or 214.

Optionally in any embodiment, the article such as 12, 14, 210, 212, or 214 has an opening 32.

Optionally in any embodiment, impinging the infrared light 216 can be carried out by passing the light 216 through the opening 32 to an interior surface which can be the first surface 44 or 220.

Optionally in any embodiment, collecting the infrared light 224 can be carried out by passing the light 224 from the first surface 44 or 220 through the opening 32 to a collector 222 positioned outside the lumen 18.

Optionally in any embodiment, at least one passing step can be carried out by projecting unconstrained impinged, collected, or reflected infrared light 216, 224, and/or 228 through the opening 32.

Optionally in any embodiment, each passing step can be carried out by projecting unconstrained impinged, collected, or reflected infrared light 216, 224, and/or 228 through the opening 32.

Optionally in any embodiment, at least one passing step can be carried out by providing a light guide 236 passing through the opening 32 and conveying the impinged, collected, or reflected infrared light 216, 224, and/or 228 in the light guide 236.

Optionally in any embodiment, each passing step can be carried out by providing a light guide 236 passing through the opening 32 and conveying the impinged, collected, or reflected infrared light 216, 224, and/or 228 in the light guide 236 through the opening 32.

Optionally in any embodiment, the impinging step can be carried out by generating the infrared light 216 within the lumen 18 and projecting the light 216 and/or conveying the light 216 through a light guide 236 to the first surface 44 or 220.

Optionally in any embodiment, the collecting step can be carried out by a collector 222 positioned within the lumen 18.

Optionally in any embodiment, the impinged, collected, or reflected infrared light 216, 224, and/or 228 follow different paths at least in part.

Optionally in any embodiment, the impinged, collected, or reflected infrared light 216, 224, and/or 228 follow a common path at least in part.

Optionally in any embodiment, the infrared light 216 can be provided by a frequency tunable laser as the source 218, for example a quantum cascade laser.

Optionally in any embodiment, the infrared light 216 can be provided by a source 218 that impinges light across a spot on the first surface 44 or 220 such that the spot has a diameter of at least 1 mm, alternatively at least 2 mm. Where the spot is not circular, e.g. where the spot is more of an oval, the diameter, as that term is used herein, should be measured across the narrowest region of the spot. A larger spot diameter is beneficial in that it provides that the analysis may be performed over a larger surface area, and thereby account for coating variations.

Optionally in any embodiment, the infrared light 216 can be provided by a source 218 that is located at least 1 inch from the first surface 44 or 220, alternatively at least 1.5 inches from the first surface, alternatively at least 2 inches from the first surface, alternatively at least 3 inches from the first surface, and alternatively at least 4 inches from the first surface. For example, the infrared light 216 can be provided by a source 218 that is located about 6 inches from the first surface 44 or 220. Put another way, the infrared light travels at least about 1 inch before it impinges onto the first surface, alternatively at least 1.5 inches, alternatively at least 2 inches, alternatively at least 3 inches, and alternatively at least 4 inches.

Optionally in any embodiment, at least the combination of the impinging and collecting steps may be performed in a total of four seconds or less, alternatively three seconds or less, alternatively two seconds or less, alternatively one second or less, or alternatively one-half of a second or less.

Optionally in any embodiment, the infrared light 216 can be provided substantially vertically, such as travelling upward from the source 218 to the first surface 44 or 220 or travelling downward from the source to the first surface. Alternatively, the infrared light 216 can be provided in other configurations, such as substantially horizontally.

Optionally in any embodiment, the container can be a capped pre-assembly 12, syringe barrel 14, pharmaceutical package 210, vial 212, and/or cartridge 214.

Optionally in any embodiment, the container has a wall such as the first surface 220 generally opposite the opening 32.

Optionally in any embodiment, the container, for example the capped pre-assembly 12, syringe barrel 14, pharmaceutical package 210, vial 212, and/or cartridge 214, can include or be a generally cylindrical surface 44 such as the inner wall 16 between the opening 32 and the wall generally opposite the opening 32.

Optionally in any embodiment, impinging can be carried out at least in part by projecting a beam of the infrared light 216 axially through the opening 32 to the wall 220 generally opposite the opening 32.

Optionally in any embodiment, the impinged, collected, or reflected infrared light 216, 224, and/or 228 can be projected parallel to the axis 230 of the generally cylindrical surface 44, non-parallel to but intersecting the axis 230, or skewed (non-parallel and non-intersecting) with respect to the axis 230.

Optionally in any embodiment, the impinged, collected, or reflected infrared light 216, 224, and/or 228 can be offset radially from the axis 230 of the generally cylindrical surface 44.

Optionally in any embodiment, plural measurements are taken by impinging the infrared light 216 at more than one position such as 238, 240, and/or 242 on the article such as 12, 14, 210, 212, or 214.

Optionally in any embodiment, the first surface can be the generally cylindrical surface 44 instead of the end surface 220.

Optionally in any embodiment, at least a portion of the impinged infrared light 216 can be reflected from the first surface 44 or 220 of the article such as 12, 14, 210, 212, or 214 being examined before collecting at least a portion of the infrared light 224.

Optionally in any embodiment, at least a portion of the reflected infrared light 228 can be impinged on at least a second surface before collecting at least a portion of the infrared light as 224.

Optionally in any embodiment, the second surface such as 44 of the article such as 12, 14, 210, 212, or 214 is also being examined for a coating or layer 30 and/or 248 of $SiO_xC_y$, or $SiN_xC_y$.

Optionally in any embodiment, the second surface such as 44 of the article such as 12, 14, 210, 212, or 214 is also being examined for a coating or layer 34 of $SiO_x$.

Optionally in any embodiment, an optical element such as 244 or 246 can be inserted in the lumen 18 for bending the path of the infrared light 216 and/or 224 during at least one of the impinging and collecting steps. Examples of suitable optical elements in any embodiment, usable alone or together, include a mirror 244 or a prism 246.

Optionally in any embodiment, at least a portion of the article such as 12, 14, 210, 212, or 214 defining the first surface 44 or 220 can be made of transparent material. Some examples of suitable transparent material include a polycarbonate, an olefin polymer (for example polypropylene (PP) or polyethylene (PE)), a cyclic olefin copolymer (COC), a cyclic olefin polymer or cyclic olefin copolymer (COP), polymethylpentene, a polyester (for example polyethylene terephthalate, polyethylene naphthalate, or polybutylene terephthalate (PBT)), PVdC (polyvinylidene chloride), polyvinyl chloride (PVC), polycarbonate, polylactic acid, polystyrene, hydrogenated polystyrene, poly(cyclohexylethylene) (PCHE), epoxy resin, nylon, polyurethane polyacrylonitrile (PAN), polyacrylonitrile (PAN), an ionomeric resin (for example Surlyn®), or glass (for example borosilicate glass), or a combination of any two or more of these. Optionally in any embodiment, the transparent material can include or be a cyclic olefin polymer or cyclic olefin copolymer, a polyethylene terephthalate or a polypropylene; and more preferably can include or be a cyclic olefin polymer or cyclic olefin copolymer. "Transparent" for the present specification means an article or portion of an article such as 12, 14, 210, 212, or 214 through which an image can be seen. A transparent material can be colored or colorless, providing it meets this test for transparency.

Optionally in any embodiment, the presence or absence of the $SiO_xC_y$ or $SiN_xC_y$ coating or deposit such as 30 and/or 248 can be determined in the presence of the material defining the first surface 44 or 220.

Optionally in any embodiment, a second coating 248 of $SiO_xC_y$ or $SiN_xC_y$, for example a pH protective coating 248, can be applied over the coating or layer 34 of $SiO_x$.

Optionally in any embodiment, the coatings or deposits such as 30 and/or 248 of $SiO_xC_y$ or $SiN_xC_y$ are measured in the presence of the first surface 44 or 220 and in the presence of the coating or deposit such as 34 of $SiO_x$.

Optionally in any embodiment, the coatings or deposits such as 30 and/or 248 of $SiO_xC_y$ or $SiN_xC_y$ are distinguished from the first surface 44 or 220, any coating or deposit such as 34 of $SiO_x$, or both by a detectable infrared spectroscopy peak 234 in the wave number range from about 1245 to about 1270 $cm^{-1}$, indicative of a coating or deposit such as 30 and/or 248 of $SiO_xC_y$ or $SiN_xC_y$.

Optionally in any embodiment, the thickness of the coating or deposit such as 30 and/or 248 of $SiO_xC_y$ or $SiN_xC_y$ can be determined from the intensity of the collected infrared light 224 in the wave number range between 1230 and 1300 $cm^{-1}$, for example from about 1245 to about 1270 $cm^{-1}$.

Optionally in any embodiment, the coatings or deposits such as 30 and/or 248 of $SiO_xC_y$ or $SiN_xC_y$ are distinguished from the first surface 44 or 220, any coating or deposit such as 34 of $SiO_x$, or both by a detectable infrared spectroscopy peak 234 in the wave number range from about 1015 to about 1035 $cm^{-1}$, indicative of a coating or deposit such as 30 and/or 248 of $SiO_xC_y$ or $SiN_xC_y$.

Optionally in any embodiment, the thickness of the coating or deposit such as 30 and/or 248 of $SiO_xC_y$ or $SiN_xC_y$ can be determined from the intensity of the collected infrared light 224 in the wave number range between 950 and 1230 $cm^{-1}$, for example from about 1015 to about 1035 $cm^{-1}$.

Optionally in any embodiment, the coatings or deposits such as 30 and/or 248 of $SiO_xC_y$ or $SiN_xC_y$ are distinguished from the first surface 44 or 220, any coating or deposit such as 34 of $SiO_x$, or both by detectable infrared spectroscopy peaks 234 in the wave number ranges from about 1015 to about 1035 $cm^{-1}$ and from about 1245 to about 1270 $cm^{-1}$, indicative of a coating or deposit such as 30 and/or 248 of $SiO_xC_y$ or $SiN_xC_y$.

Optionally in any embodiment, the thickness of the coating or deposit such as 30 and/or 248 of $SiO_xC_y$ or $SiN_xC_y$ can be determined from the intensity of the collected infrared light 224 in the wave number ranges between 950 and 1230 $cm^{-1}$, for example from about 1015 to about 1035 $cm^{-1}$, and between 1230 and 1300 $cm^{-1}$, for example from about 1245 to about 1270 $cm^{-1}$.

Optionally in any embodiment, the presence or absence of the $SiO_x$ coating or deposit such as 34 can be determined in the presence of the material defining the first surface 44 or 220.

Optionally in any embodiment, the coating or deposit such as 34 of $SiO_x$ is measured in the presence of the first surface 44 or 220 and in the presence of the coatings or deposits such as 30 and/or 248 of $SiO_xC_y$ or $SiN_xC_y$.

Optionally in any embodiment, the coating or deposit such as 34 of $SiO_x$ is distinguished from the first surface 44 or 220, any coating or deposit such as 30 and/or 248 of $SiO_xC_y$ or $SiN_xC_y$, or both by a detectable infrared spectroscopy peak 234 in the wave number range from about 1060 to about 1080 $cm^{-1}$, indicative of a coating or deposit such as 34 of $SiO_x$.

Optionally in any embodiment, the thickness of the coating or deposit such as 34 of $SiO_x$ can be determined from the intensity of the collected infrared light 224 in the wave number range from about 1060 to about 1080 $cm^{-1}$.

Optionally in any embodiment, the impinging of infrared light onto at least a first surface 44 or 220 is performed on a production line for the article.

Optionally in any embodiment, the detecting of coating 30 is performed on a production line for the article.

Optionally in any embodiment, the detecting of coating 34 is performed on a production line for the article.

Optionally in any embodiment, the detecting of coating 248 is performed on a production line for the article.

Optionally in any embodiment, the maximum intensity and/or peak area of the collected infrared light at an infrared spectroscopy peak 234 indicative of a coating or deposit of $SiO_xC_y$ or $SiN_xC_y$ is compared against a predetermined parameter.

Optionally in any embodiment, the article is assigned a status of either passing or failing based on the comparison between the maximum intensity and/or peak area of the collected infrared light at an infrared spectroscopy peak 234 indicative of a coating or deposit of $SiO_xC_y$ or $SiN_xC_y$, and the predetermined parameter.

Optionally in any embodiment, the maximum intensity and/or peak area of the collected infrared light at an infrared spectroscopy peak 234 indicative of a coating or deposit of $SiO_x$ is compared against a predetermined parameter.

Optionally in any embodiment, the article is assigned a status of either passing or failing based on the comparison between the maximum intensity and/or peak area of the collected infrared light at an infrared spectroscopy peak 234 indicative of a coating or deposit of $SiO_x$ and the predetermined parameter.

Optionally in any embodiment, a first coating or deposit such as 30 of $SiO_xC_y$ or $SiN_xC_y$, where x can be from about 0.5 to about 2.4 and y can be from about 0.6 to about 3, can be present over the first surface 44 or 220.

Optionally in any embodiment, a coating or layer 34 of $SiO_x$, in which x can be from about 1.5 to about 2.9, can be present over the first coating or deposit such as 30 and/or 248 of $SiO_xC_y$ or $SiN_xC_y$.

Optionally in any embodiment, a second coating or deposit such as 248 of $SiO_xC_y$ or $SiN_xC_y$, where x can be from about 0.5 to about 2.4 and y can be from about 0.6 to about 3, can be present over the coating or layer 34 of $SiO_x$.

Optionally in any embodiment, the collected infrared light 224 can be measured to determine the cumulative thickness of the first coating or deposit such as 30 of $SiO_xC_y$ or $SiN_xC_y$ and the second coating or deposit such as 248 of $SiO_xC_y$ or $SiN_xC_y$, with the coating or layer 34 of $SiO_x$ in place between them.

Optionally in any embodiment, a mold lubricant 232 to be detected, if present, can include or be polytetrafluoroethylene.

Optionally in any embodiment, the mold lubricant 232 produces an infrared spectroscopy peak at about 1100 to 1110 $cm^{-1}$.

Optionally in any embodiment, the coating or deposit such as 232 of the mold lubricant 232 produces no interfering infrared spectroscopy peak in the wave number range indicative of the material defining the first surface 44 or 220 of the article such as 12, 14, 210, 212, or 214.

Optionally in any embodiment, the mold lubricant 232 produces no interfering infrared spectroscopy peak in the wave number range indicative of a coating or deposit such as 30 and/or 248 of $SiO_xC_y$ or $SiN_xC_y$.

Optionally in any embodiment, the infrared spectroscopy peak 234 indicative of a coating or deposit such as 232 of the mold lubricant can be outside the range from about 1245 to about 1270 cm$^{-1}$. Optionally in any embodiment, the infrared spectroscopy peak 234 indicative of a coating or deposit such as 232 of the mold lubricant can be outside the range from about 1015 to about 1035 cm$^{-1}$. Optionally in any embodiment, the infrared spectroscopy peak 234 indicative of a coating or deposit such as 232 of the mold lubricant can be outside the range from about 1060 to about 1080 cm$^{-1}$ Optionally in any embodiment, the mold lubricant 232 can include or be polydimethylsiloxane.

Optionally in any embodiment, the mold lubricant 232 can include or be $SiO_xC_y$ or $SiN_xC_y$.

Optionally in any embodiment, the material defining the first surface 44 or 220 of the article such as 12, 14, 210, 212, or 214 can include or be a cyclic olefin polymer or cyclic olefin copolymer.

Optionally in any embodiment, the material defining the first surface 44 or 220 of the article such as 12, 14, 210, 212, or 214 produces no interfering infrared spectroscopy peak in the wave number range indicative of the mold lubricant 232.

Optionally in any embodiment, the material defining the first surface 44 or 220 of the article such as 12, 14, 210, 212, or 214 produces no interfering infrared spectroscopy peak in the wave number range indicative of a coating or deposit such as 30 and/or 248 of $SiO_xC_y$ or $SiN_xC_y$.

Optionally in any embodiment, the infrared spectroscopy peak indicative of the material defining the first surface 44 or 220 of the article such as 12, 14, 210, 212, or 214 can be outside the range from about 1245 to about 1270 cm$^{-1}$.

Optionally in any embodiment, the infrared spectroscopy peak indicative of the material defining the first surface 44 or 220 of the article such as 12, 14, 210, 212, or 214 can be outside the range from about 1015 to about 1035 cm$^{-1}$.

Optionally in any embodiment, the infrared spectroscopy peak indicative of the material defining the first surface 44 or 220 of the article such as 12, 14, 210, 212, or 214 can be outside the range from about 1060 to about 1080 cm$^{-1}$.

Optionally in any embodiment, at least a portion of the first surface 44 or 220 can be curved during impinging.

Optionally in any embodiment, the impinging and collecting can be carried out using a remote infrared spectrometer having a light source 218 and a collector 222.

Optionally in any embodiment, at least one coating or layer of $SiO_xC_y$ or $SiN_xC_y$ can include or be a pH protective coating or layer 248 having the property of reducing the dissolution of silicon from the first surface 44 or 220 by an aqueous fluid having a pH of at least 5.

Optionally in any embodiment, at least one coating or layer of $SiO_xC_y$ or $SiN_xC_y$ can include or be a lubricity coating or layer 250 having the property of reducing the $F_i$ or $F_m$ value of the first surface 44.

Optionally in any embodiment, at least one coating or layer 30 of $SiO_xC_y$ or $SiN_xC_y$ can be a tie coating or layer 30 for increasing adhesion between the first surface 44 or 220 and a subsequent coating or layer, such as the $SiO_x$ coating or layer 34.

Optionally in any embodiment, at least one coating or layer 248 of $SiO_xC_y$ or $SiN_xC_y$ has a surface energy suited for preventing interaction with a material stored in contact with the first surface 44 or 220.

Optionally in any embodiment, at least one coating or layer of $SiO_xC_y$ or $SiN_xC_y$ 248 can include or be a scratch resistant coating or layer.

Optionally in any embodiment, at least one coating or layer 30 and/or 248 of $SiO_xC_y$ or $SiN_xC_y$ can include or be a plasma enhanced chemical vapor deposition (PECVD) coating.

Optionally in any embodiment, a coating or layer 34 of $SiO_x$ can include or be a gas barrier coating.

Optionally in any embodiment, the coating or layer 34 of $SiO_x$ can include or be a plasma enhanced chemical vapor deposition (PECVD) coating.

Optionally in any embodiment, at least one coating or layer 30 and/or 248 of $SiO_xC_y$ or $SiN_xC_y$ is present on the first surface 44 or 220 before impinging.

Optionally in any embodiment, after applying at least one coating or layer 30 and/or 248 of $SiO_xC_y$ or $SiN_xC_y$ to the first surface 44 or 220 and before impinging, at least one coating or layer 34 of $SiO_x$ can be applied to the first surface 44 or 220.

Optionally in any embodiment, after applying at least one coating or layer 30 of $SiO_xC_y$ or $SiN_xC_y$ and at least one coating or layer 34 of $SiO_x$ to the first surface 44 or 220 and before impinging, at least a second coating or layer 248 of $SiO_xC_y$ or $SiN_xC_y$ can be applied to the first surface 44 or 220.

Optionally in any embodiment, at least one coating or layer 30 and/or 248 of $SiO_xC_y$ or $SiN_xC_y$ can include or be $SiO_xC_y$. Optionally in any embodiment, each coating or layer 30 and/or 248 of $SiO_xC_y$ or $SiN_xC_y$ can include or be $SiO_xC_y$. Optionally in any embodiment, each coating or layer 30 and/or 248 of $SiO_xC_y$ or $SiN_xC_y$ consists essentially of $SiO_xC_y$.

Optionally in any embodiment, the at least one coating or layer 248 of $SiO_xC_y$ or $SiN_xC_y$ as applied can be between 10 and 1000 nm thick, alternatively between 50 and 800 nm thick, alternatively between 100 and 700 nm thick, alternatively between 300 and 600 nm thick.

Optionally in any embodiment, the pH protective coating or layer 248 contacting the fluid composition 40 can be between 10 and 1000 nm thick, alternatively between 20 and 700 nm thick, alternatively between 50 and 500 nm thick, alternatively between 100 and 400 nm thick, alternatively between 150 and 300 nm thick, two years after the article is assembled.

Optionally in any embodiment, the rate of erosion of the pH protective coating or layer 248, if directly contacted by a fluid composition 40 having a pH of 8, can be less than 20%, alternatively less than 15%, alternatively less than 10%, alternatively less than 7%, alternatively from 5% to 20%, alternatively from 5% to 15%, alternatively 5% to 10%, alternatively from 5% to 7% of the rate of erosion of the barrier coating or layer 34, if directly contacted by the same fluid composition 40 under the same conditions.

Optionally in any embodiment, the pH protective coating or layer 248 can be at least coextensive with the barrier coating or layer 34.

Optionally in any embodiment, an FTIR absorbance spectrum of the pH protective coating or layer 248 has a ratio greater than 0.75 between:
  the maximum amplitude of the Si—O—Si symmetrical stretch peak between about 1000 and 1040 cm$^{-1}$, and
  the maximum amplitude of the Si—O—Si asymmetric stretch peak between about 1060 and about 1100 cm$^{-1}$.

Alternatively, the ratio can be at least 0.8, alternatively at least 0.9, alternatively at least 1, alternatively at least 1.1, alternatively at least 1.2. Optionally in any embodiment, the ratio can be at most 1.7, alternatively at most 1.6, alternatively at most 1.5, alternatively at most 1.4, alternatively at most 1.3.

Optionally in any embodiment, a lubricity coating or layer 250 can be provided between the lumen 18 and the pH protective coating or layer 248, or more specifically between the plunger tip or piston 36 and the internal wall 16. The lubricity coating or layer 250 can include or be $SiO_xC_y$ or $SiN_xC_y$ wherein x can be from about 0.5 to about 2.4 and y can be from about 0.6 to about 3. Optionally, the lubricity coating or layer 250 can be effective to increase the lubricity of the coating set above that of a coating set having a pH protective coating as the layer confronting the lumen 18.

Optionally in any embodiment, a syringe barrel 14 can be coated on its internal wall 16 with a pH protective coating or layer 248, a plunger 36 can be positioned for sliding in the barrel 14, and a lubricity coating or layer 250 can be provided on at least a portion of the plunger 36. Optionally in any embodiment, the lubricity coating or layer 250 can be configured to provide a lower piston sliding force or breakout force than the uncoated substrate.

Optionally in any embodiment, the lubricity coating or layer 250 has one of the following atomic ratios, measured by X-ray photoelectron spectroscopy (XPS), $Si_wO_xC_y$ (or its equivalent $SiO_xC_y$) or $Si_wN_xC_y$ (or its equivalent SiNxCy) where w can be 1, x in this formula can be from about 0.5 to 2.4, and y can be from about 0.6 to about 3.

Optionally in any embodiment, the lubricity coating or layer 250 has a thickness by transmission electron microscopy (TEM) between 10 and 1000 nm.

Optionally in any embodiment, the pH protective coating or layer 248 has an O-Parameter value (ratio of infrared absorption) of less than 0.4, measured by remote infrared spectroscopy as:

$$O\text{-Parameter} = \frac{\text{Intensity at wave number 1253 cm}^{-1}}{\text{Maximum intensity in the wave number range 1000 to 1100 cm}^{-1}}.$$

Alternatively, the O-parameter has a value of from 0.1 to 0.39, alternatively from 0.15 to 0.37, alternatively from 0.17 to 0.35.

Optionally in any embodiment, the pH protective coating or layer 248 has an N-Parameter value (ratio of infrared absorption) of less than 0.7, measured by remote infrared spectroscopy as:

$$N\text{-Parameter} = \frac{\text{Intensity at wave number 840 cm}^{-1}}{\text{Intensity at wave number 799 cm}^{-1}}.$$

Alternatively, the N-parameter has a value of at least 0.3, alternatively from 0.4 to 0.6.

Optionally in any embodiment, the tie coating or layer 30 comprises $SiO_xC_y$, alternatively consists essentially of $SiO_xC_y$, alternatively comprises $SiN_xC_y$, alternatively consists essentially of $SiN_xC_y$.

Optionally in any embodiment, the tie coating or layer 30 can be on average between 5 and 200 nm thick, alternatively between 5 and 100 nm thick, alternatively between 10 and 100 nm thick, alternatively between 10 and 50 nm thick, alternatively between 5 and 20 nm thick. Optionally in any embodiment, the tie coating or layer 30 can be at least coextensive with the barrier coating or layer 34.

Optionally in any embodiment, the range of thickness of the barrier coating or layer 34 can be between 2 and 1000 nm thick, alternatively between 10 and 200 nm thick, alternatively between 10 and 100 nm thick, alternatively between 20 and 200 nm thick, and alternatively between 20 and 30 nm thick.

Optionally in any embodiment, the range of thickness of the pH protective coating or layer 248 can be between 10 and 1000 nm thick, alternatively between 50 and 500 nm thick, alternatively between 50 and 400 nm thick, alternatively between 50 and 250 nm thick, and alternatively between 100 and 200 nm thick.

Basic Protocols for Forming and Coating Syringe Barrels

The pharmaceutical packages or other vessels tested in the subsequent working examples were formed and coated according to the following exemplary protocols, except as otherwise indicated in individual examples. Particular parameter values given in the following basic protocols, for example the electric power and gaseous reactant or process gas flow, are typical values. When parameter values were changed in comparison to these typical values, this will be indicated in the subsequent working examples. The same applies to the type and composition of the gaseous reactant or process gas.

Protocol for Coating Syringe Barrel Interior with $SiO_x$

The apparatus and protocol generally as found in U.S. Pat. No. 7,985,188 were used for coating syringe barrel interiors with an $SiO_x$ barrier coating or layer or layer, in some cases with minor variations. A similar apparatus and protocol were used for coating vials with an $SiO_x$ barrier coating or layer or layer, in some cases with minor variations.

Protocol for Coating Syringe Barrel Interior with OMCTS Passivation Layer or Protective Coating Syringe barrels already interior coated with a barrier coating or layer or layer of $SiO_x$, as previously identified, are further interior coated with a passivation layer or protective coating as previously identified, generally following the protocols of U.S. Pat. No. 7,985,188 for applying the lubricity coating or layer, except with modified conditions in certain instances as noted in the working examples. The conditions given here are for a COC syringe barrel, and can be modified as appropriate for syringe barrels made of other materials. The apparatus is used to hold a syringe barrel with butt sealing at the base of the syringe barrel. Additionally a cap is provided that seals the end of the syringe barrel.

The syringe barrel is carefully moved into the sealing position over the extended probe or counter electrode and pushed against a plasma screen. The plasma screen is fit snugly around the probe or counter electrode insuring good electrical contact. The probe or counter electrode is grounded to the casing of the RF matching network.

The gas delivery port is connected to a manual ball valve or similar apparatus for venting, a thermocouple pressure gauge and a bypass valve connected to the vacuum pumping line. In addition, the gas system is connected to the gas delivery port allowing the gaseous reactant or process gas, octamethylcyclotetrasiloxane (OMCTS) (or the specific gaseous reactant or process gas reported for a particular example) to be flowed through the gas delivery port (under process pressures) into the interior of the syringe barrel.

The gas system is comprised of a commercially available heated mass flow vaporization system that heats the OMCTS to about 100° C. The heated mass flow vaporization system is connected to liquid octamethylcyclotetrasiloxane (Alfa Aesar® Part Number A12540, 98%). The OMCTS flow rate is set to the specific organosilicon precursor flow reported for a particular example. To ensure no condensation of the vaporized OMCTS flow past this point, the gas stream is diverted to the pumping line when it is not flowing into the interior of the COC syringe barrel for processing.

Once the syringe barrel is installed, the vacuum pump valve is opened to the vessel holder and the interior of the COC syringe barrel. A vacuum pump and blower comprise the vacuum pump system. The pumping system allows the interior of the COC syringe barrel to be reduced to pressure (s) of less than 100 mTorr while the gaseous reactant or process gases is flowing at the indicated rates.

Once the base vacuum level is achieved, the vessel holder 50 assembly is moved into the electrode assembly. The gas stream (OMCTS vapor) is flowed into the gas delivery port (by adjusting the 3-way valve from the pumping line to the gas delivery port. Pressure inside the COC syringe barrel is approximately 140 mTorr as measured by a capacitance manometer (MKS) installed on the pumping line near the valve that controls the vacuum. In addition to the COC syringe barrel pressure, the pressure inside the gas delivery port and gas system is also measured with the thermocouple vacuum gauge that is connected to the gas system. This pressure is typically less than 6 Torr.

Once the gas is flowing to the interior of the COC syringe barrel, the RF power supply is turned on to its fixed power level. A 600 Watt RF power supply is used (at 13.56 MHz) at a fixed power level indicated in a specific example. The RF power supply is connected to an auto match which matches the complex impedance of the plasma (to be created in the vessel) to the output impedance of the RF power supply. The forward power is as stated and the reflected power is 0 Watts so that the stated power is delivered to the interior of the vessel. The RF power supply is controlled by a laboratory timer and the power on time set to 10 seconds (or a different time stated in a given example).

Upon initiation of the RF power, a uniform plasma is established inside the interior of the vessel. The plasma is maintained for the entire passivation layer or protective coating time, until the RF power is terminated by the timer. The plasma produces a passivation layer or protective coating on the interior of the vessel.

After passivation layer or protective coating, the gas flow is diverted back to the vacuum line and the vacuum valve is closed. The vent valve is then opened, returning the interior of the COC syringe barrel to atmospheric pressure (approximately 760 Torr). The treated vessel is then carefully removed from the vessel holder assembly (after moving the vessel holder assembly out of the electrode assembly).

A similar protocol is used for applying a passivation layer or protective coating to vials.

Example 1—Syringe Study

A Block Engineering LaserScan 610 quantum cascade laser (QCL) operating nominally from 1621-995 cm$^{-1}$ at a spectral resolution of 4 cm$^{-1}$ was utilized. All spectra represent a single scan (co-add=1). Spectral Intensity at 1263 cm$^{-1}$ was determined by the peak height method.

9 syringes PECVD coated as described in Table 1 were tested. Vial set 1 received no coating Vial set 2 received a bilayer coating (tie coating or layer plus SiO$_x$ barrier coating or layer), and vial set 3 received a trilayer coating (tie coating or layer plus SiO$_x$ barrier coating or layer, plus pH protective coating or layer). The barrel of each syringe was 54.5 mm long and had a minimum inner diameter of 6.35 mm. The front wall of each syringe was essentially solid except for the aperture for the needle opening.

Figure 5:
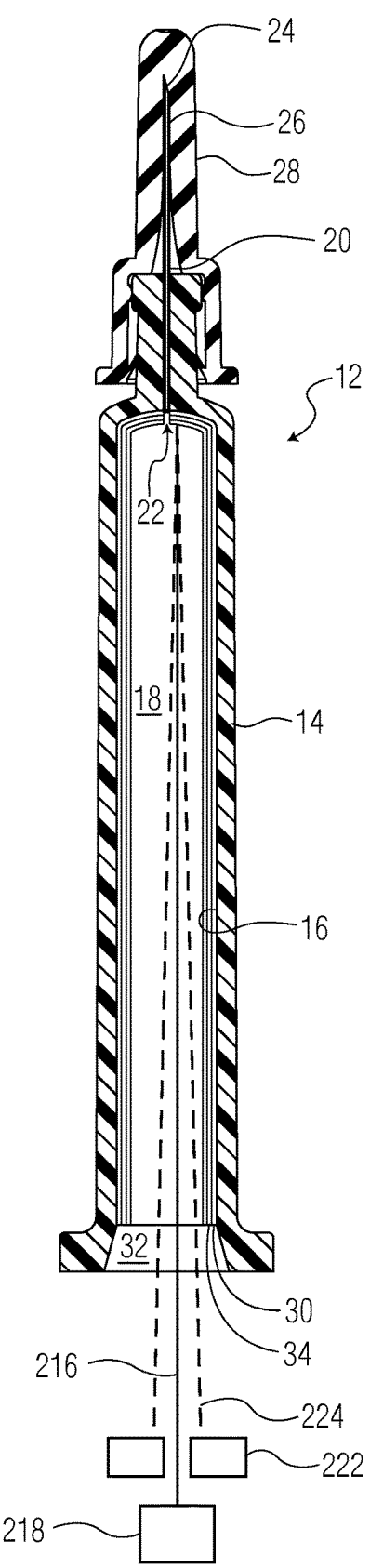
FIG. 5 is a schematic view similar to FIG. 2 showing an arrangement for measuring spectroscopy data of a syringe barrel in a syringe barrel and cap assembly.
Figure 6:
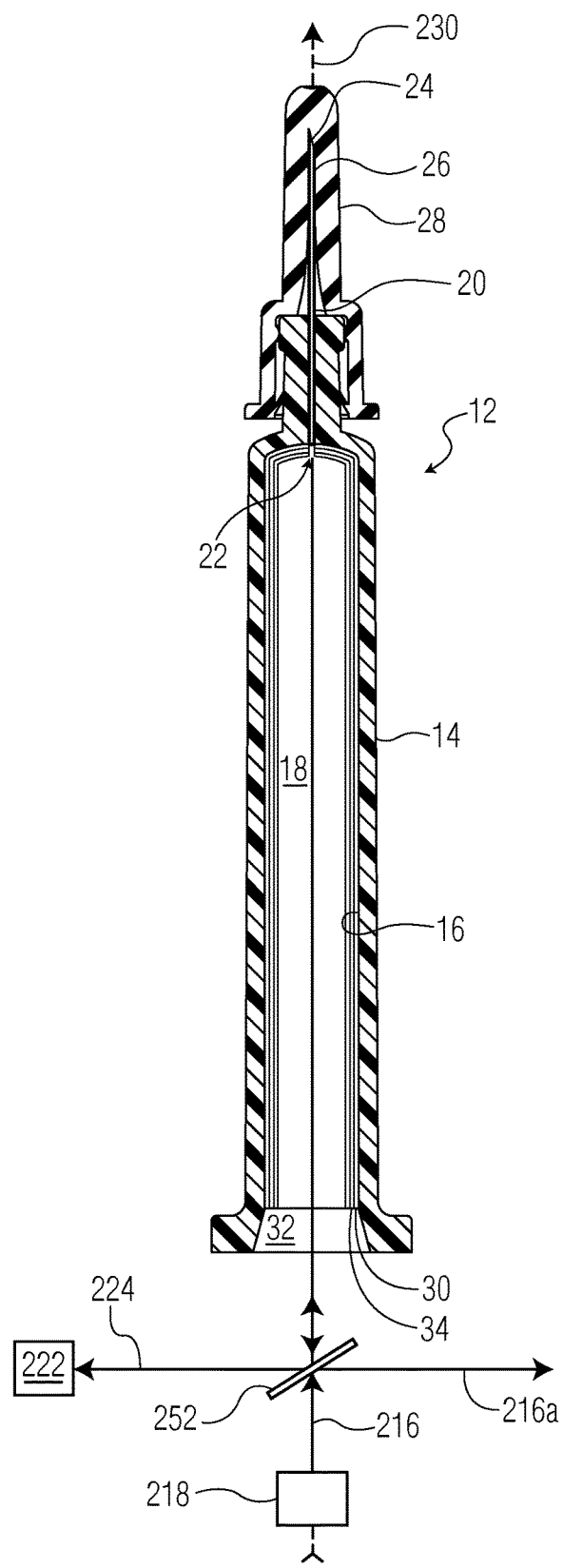
FIG. 6 is a schematic view similar to FIG. 2 showing another arrangement for measuring spectroscopy data of a syringe barrel.
Figure 7:
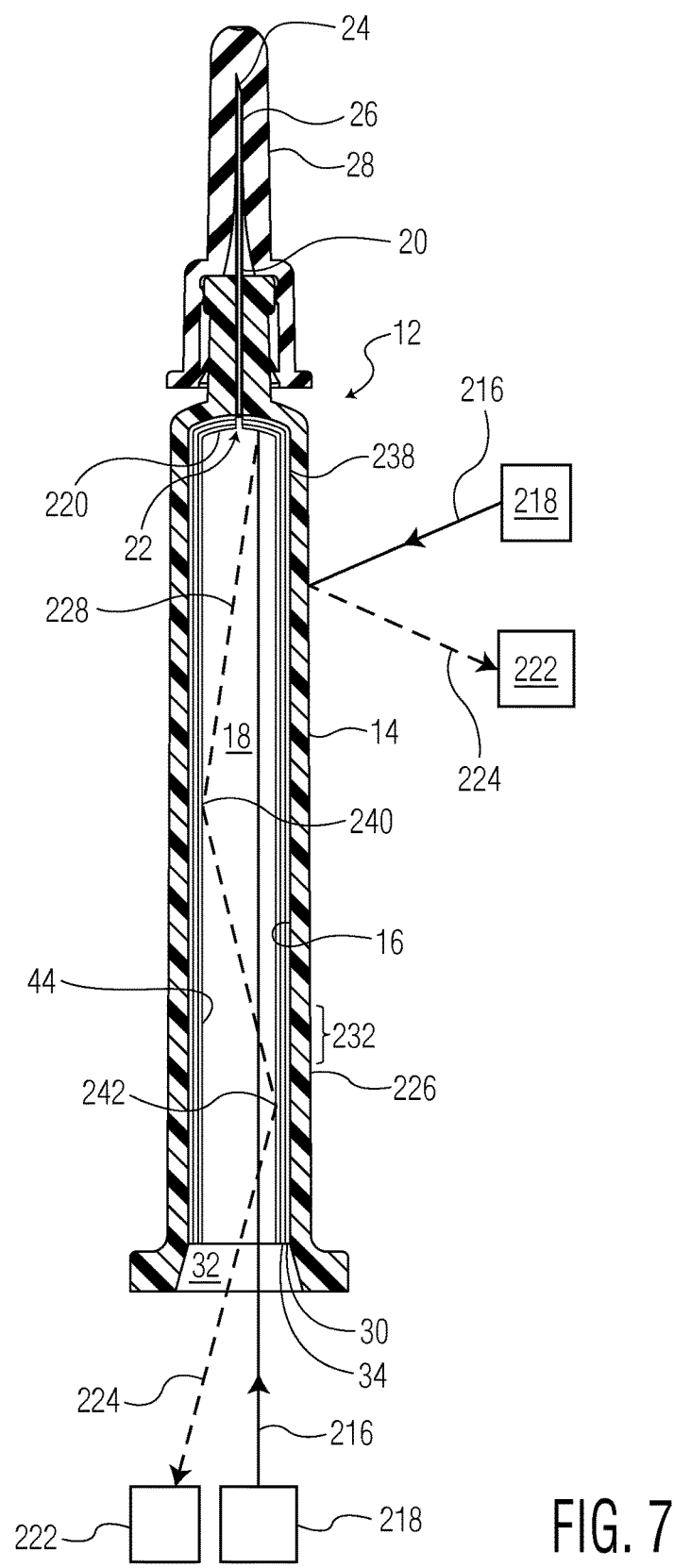
FIG. 7 is a schematic view similar to FIG. 2 showing another arrangement for measuring spectroscopy data of a syringe barrel.
Figure 8:
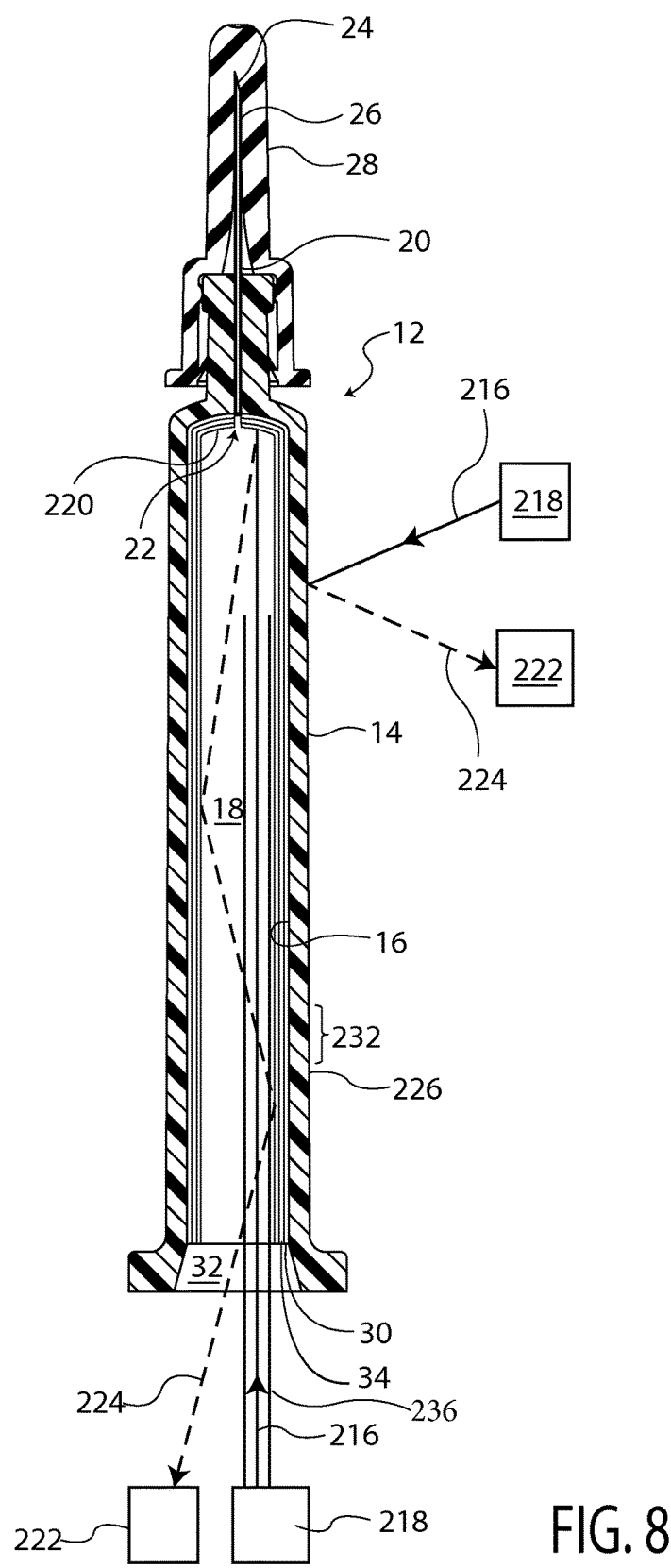
FIG. 8 is a schematic view similar to FIG. 2 showing another arrangement for measuring spectroscopy data of a syringe barrel.
Figure 9:
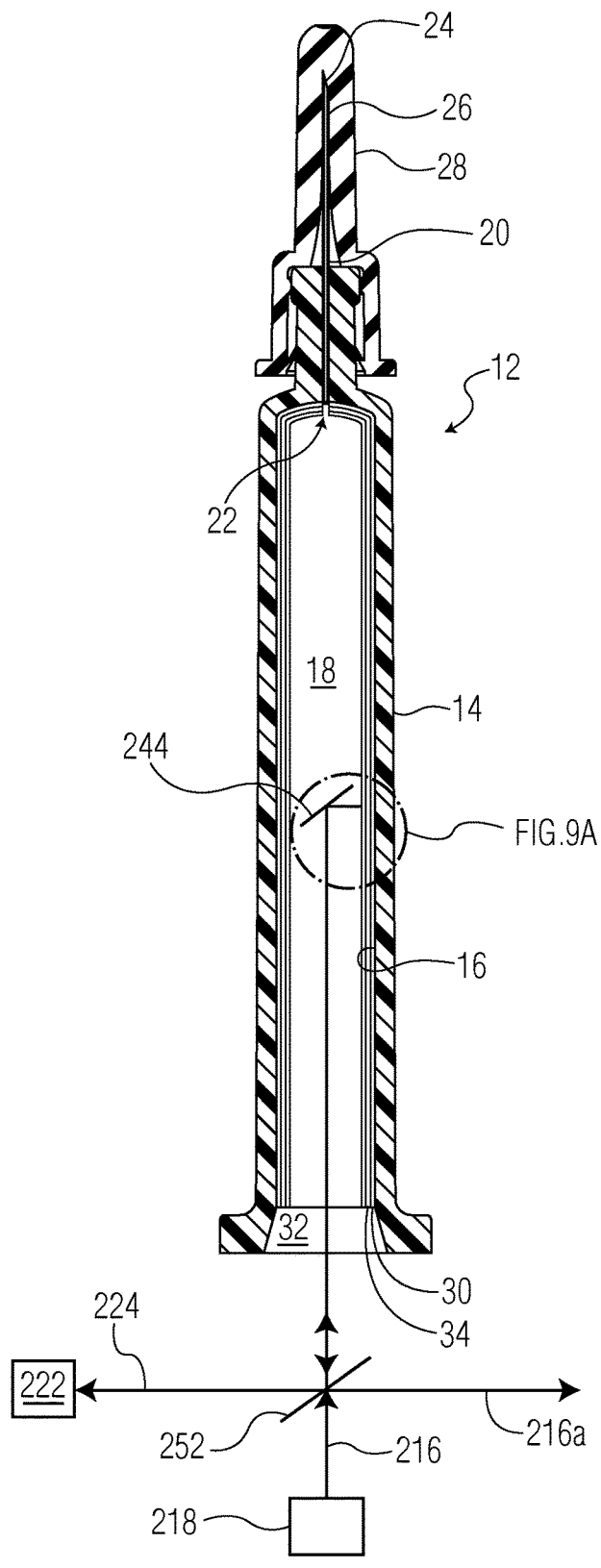
FIG. 9 is a schematic view similar to FIG. 2 showing another arrangement for measuring spectroscopy data of a syringe barrel.
Figure 9A:
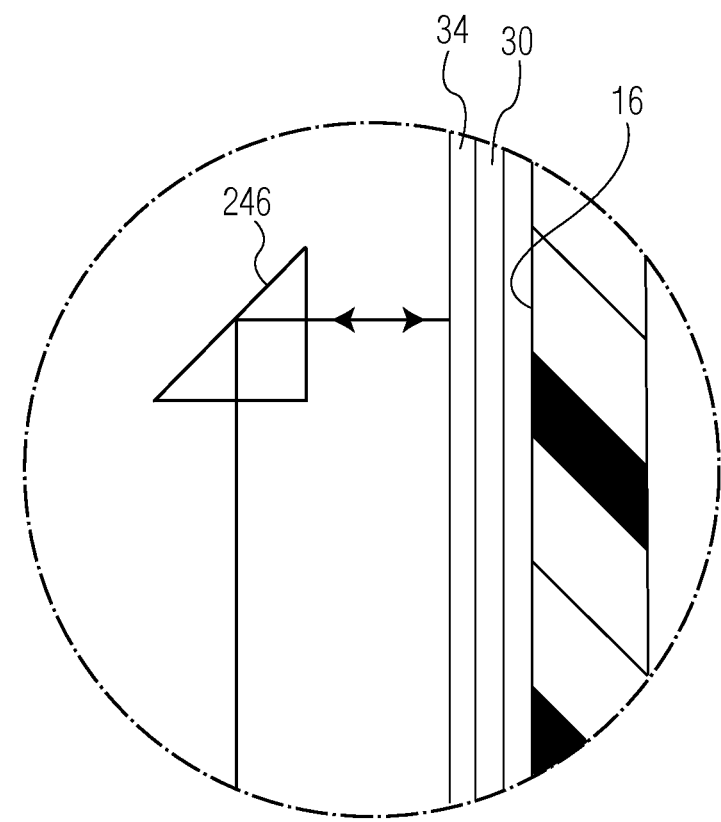
FIG. 9a is a fragmentary detail view similar to FIG. 9 showing another arrangement for measuring spectroscopy data of a syringe barrel.
Figure 10:
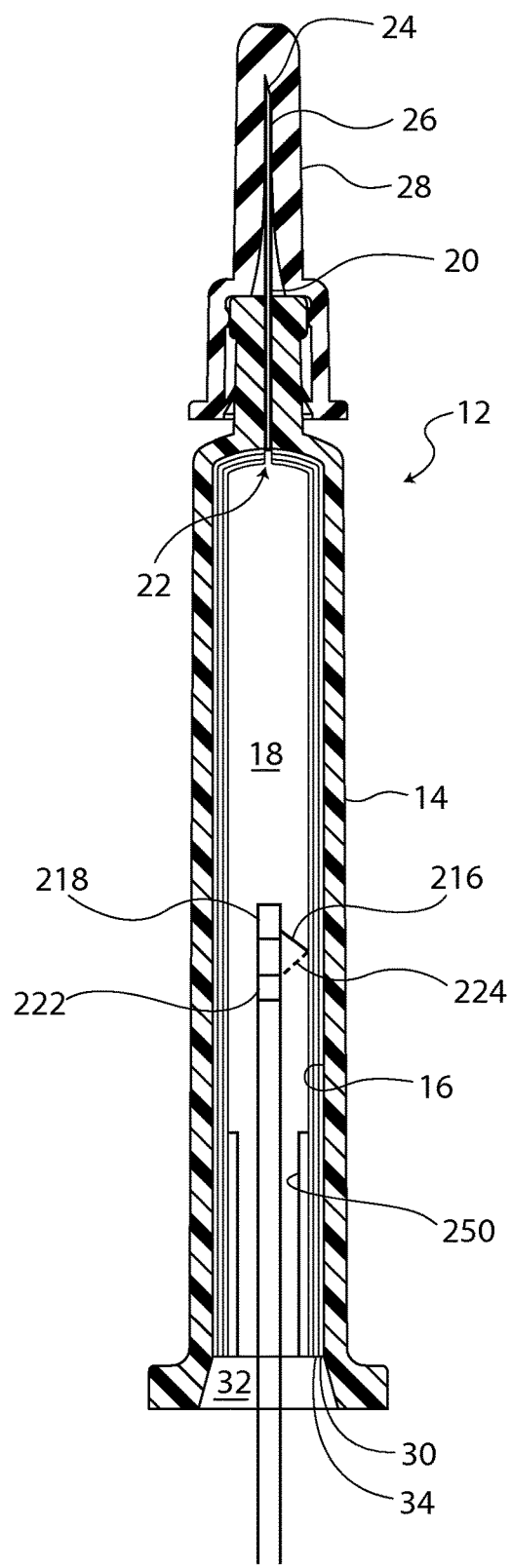
FIG. 10 is a schematic view similar to FIG. 2 showing another arrangement for measuring spectroscopy data of a syringe barrel.

A vertical configuration schematically illustrated in FIG. 5 was used for syringe barrel inspections, utilizing a three-axis mounting stage for syringe barrel placement relative to the laser source, impinging on the conical section 220 of the syringe barrel (the transition area between the cylindrical surface 44 and the plastic-needle or dispensing portion 20 interface. While the z axis distance was not critical, the x- and y-axis alignment as well as the degree of tilt was important to signal intensity. Under alignment conditions, the 2×4 mm laser source beam was fully inscribed inside the 6.25 mm ID shaft and did not reflect off the barrel flange. It was determined that the maximum reflection signal was obtained when the syringe bottoms were approximately 5.5 in. (14 cm) from the spectrometer collection lens. Because the syringes were narrow and relatively long, a secondary positioning adjustment was used to alter the tilt of each part to maximize the detected reflection signal. During the course of the preliminary measurements, it was also confirmed that the QCL beam entered the syringe barrels parallel to and offset radially from the axis and was not reflected off of the barrel flanges.

Four spectra at 0, 90, 180, and 270 degrees rotating the syringe on the z-axis 230 were taken for each syringe and averaged.

Syringe barrel samples (Table 1) were prepared. The approximate thicknesses of the SiO$_x$ and pH Protective coatings, by TEM (transmission electron microscopy) at four different locations in the syringe barrel are shown in Table 2 and FIG. 14.

TABLE 1

Tested Syringe Barrels

| Vial Set | Adhesion Coating Time (sec) | SiO$_x$ Coating TIme (sec) | pH Protective Coating Time (sec) | Number of Syringe Barrels |
|---|---|---|---|---|
| 1 | 0 | 0 | 0 | 3 |
| 2 | 2.5 | 15 | 0 | 3 |
| 3 | 2.5 | 15 | 10 | 3 |

TABLE 2

Syringe Coating Thicknesses (nm)

Figure 16:
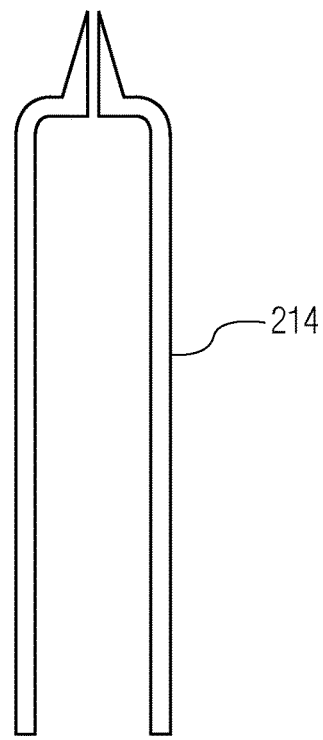
FIG. 16 is a view similar to FIG. 2 showing an auto-injector cartridge.
Figure 17:
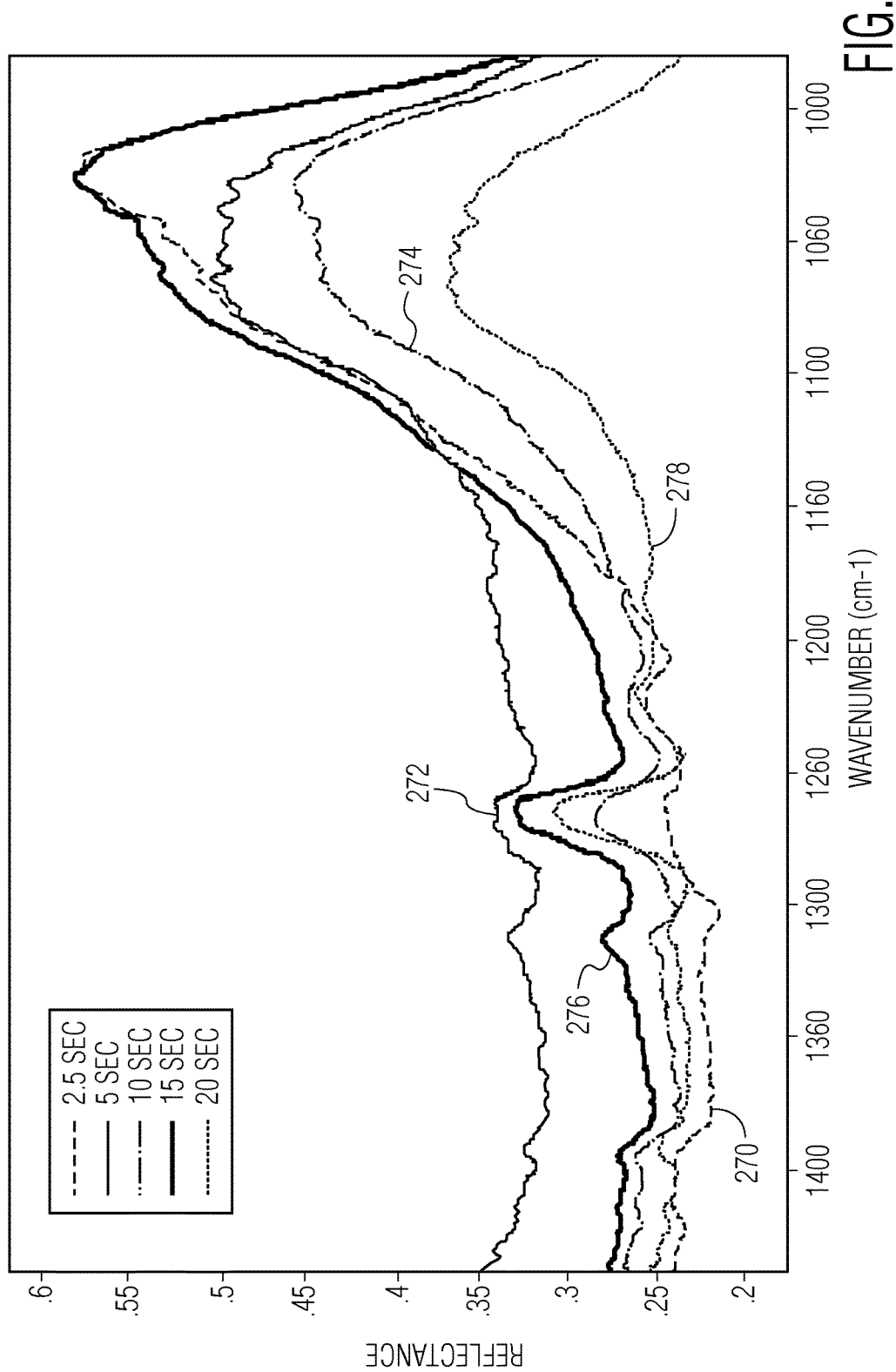
FIG. 17 is an infrared spectrophotometry spectrum plot of the vial data of Example 2.

| Syringe Location (FIG. 16) | Barrier Coating or Layer (nm) | pH Protective Coating or Layer (nm) |
|---|---|---|
| 1 | 75 | 343 |
| 2 | 55 | 273 |
| 3 | 47 | 493 |
| 4 | 25 | 287 |

A roughened gold target was used as reference. The spectral scan time (1600-1000 cm$^{-1}$) was about 14 seconds.

Figure 11:
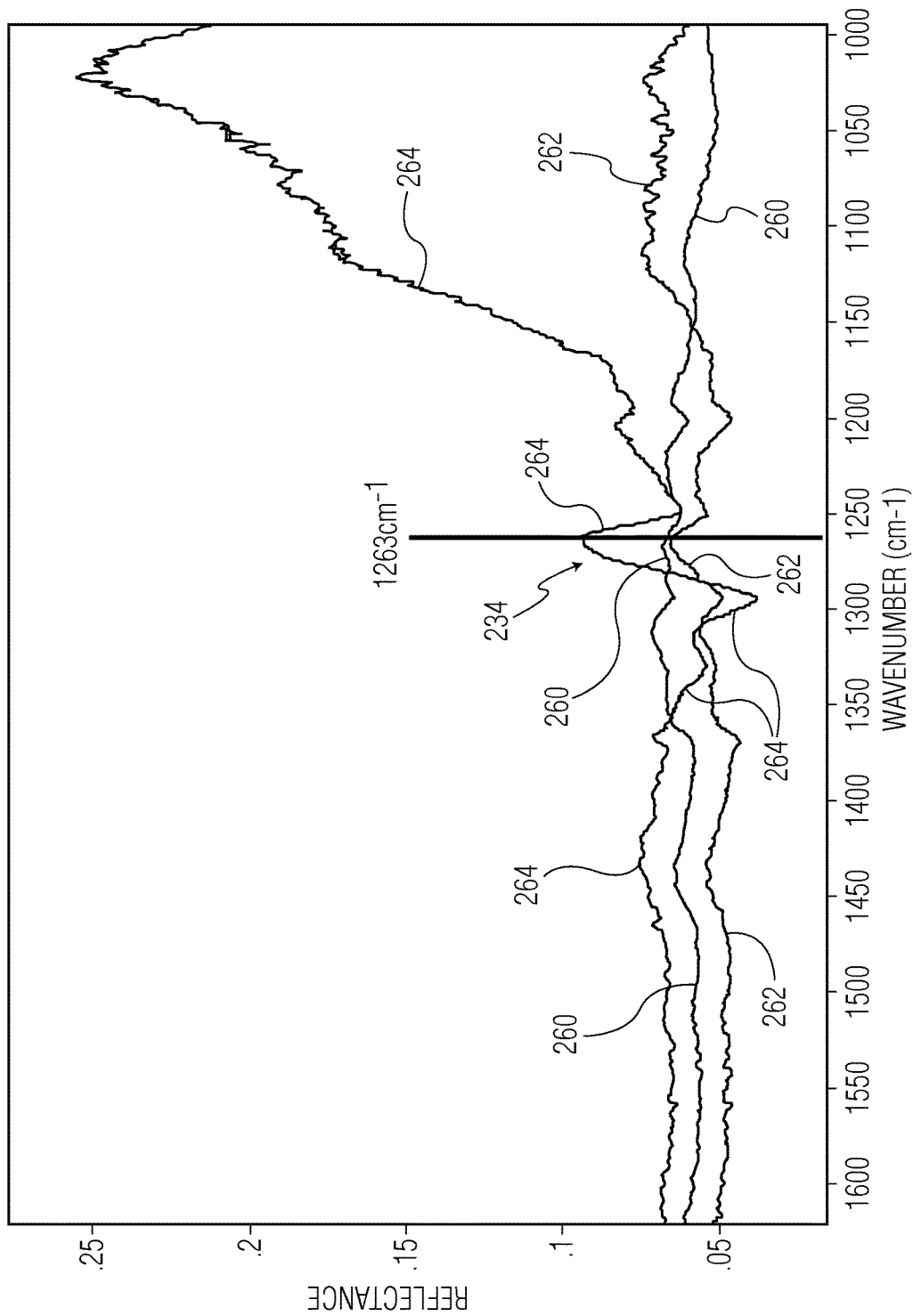
FIG. 11 is an infrared spectrophotometry spectrum plot of the syringe data of Example 1.

The spectra obtained, plotted on FIG. 11, clearly indicated no absorption at a peak 234 located at about 1263 cm$^{-1}$ for the uncoated barrels of set 1 (plot 260), a very weak absorption for the barrels of set 2 coated with a 2.5 second SiO$_x$C$_y$ tie coating or layer followed by a 15-second SiO$_x$ barrier layer (plot 262), and a significant absorption for the barrels of set 3 further coated with a 10 second SiO$_x$C$_y$ pH protective coating, thus in total a trilayer coating (plot 264).

Figure 12:
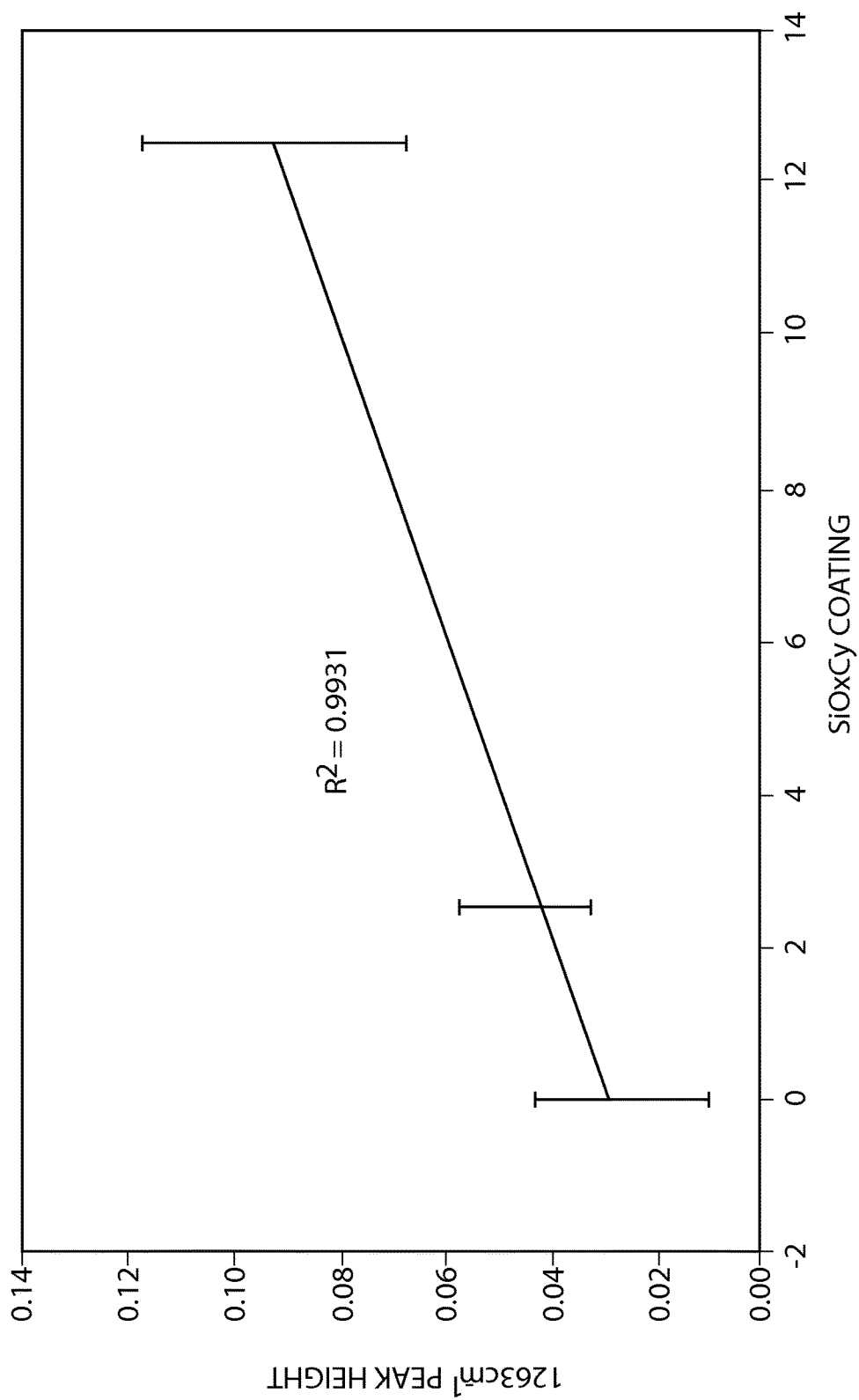
FIG. 12 is a linearized plot of peak height vs. coating time derived from the data shown in FIG. 13.
Figure 13:
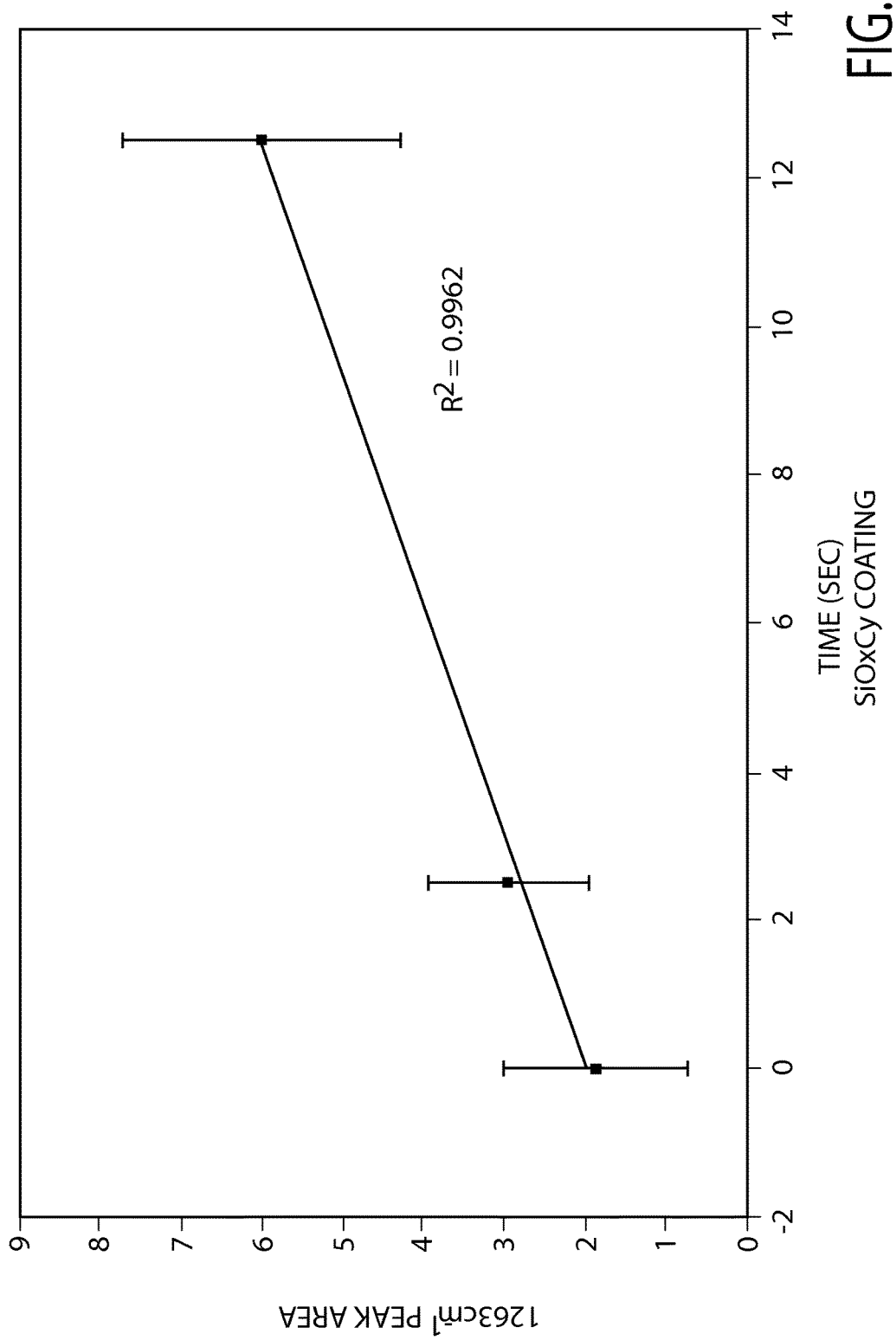
FIG. 13 is a linearized plot of peak area vs. coating time derived from the data shown in FIG. 13.

Plotting the absorbance of the syringe barrels both by the peak height and peak area method, shown in FIGS. 12-13, after converting the reflectance data (R) to log(1/R) units (L) at each wavenumber point to linearize the ordinate axis, provided a linear regression (R2) of 0.993 and 0.996, respectively, which is good for the small data set. Given the small data set the deviation in measurement was large.

Figure 14:
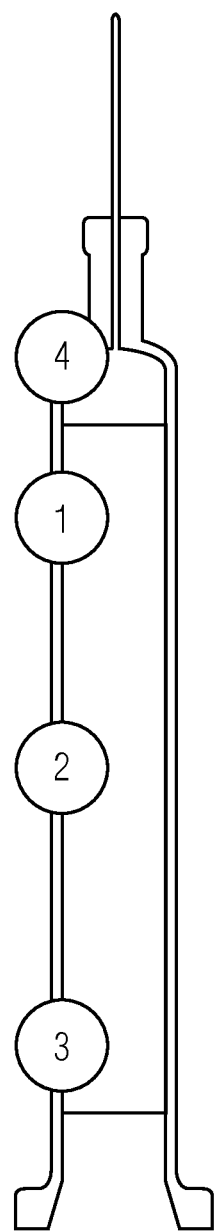
FIG. 14 is a schematic map of coating thickness versus location for a typical syringe coated as described in the working examples.

This study demonstrated that the $SiO_xC_y$ layer can be detected at the inside bottom of the test syringes in a non-destructive, non-contact fashion using a QCL spectrometer and an external gold film reference. The measured signals were generally proportional to the coating thicknesses. While this interrogation of the syringe cone did not represent a comprehensive assessment of the total syringe barrel surface, it does represent results at a syringe location (4) of interest, in that Transmission Electron Microscopy thickness determinations indicated the front wall region typically has the thinnest coating over the syringe (FIG. 14, Table 2).

Example 2—Vial Study

A second test was carried out under similar conditions to the first test, using vials 1-96 coated with trilayer coatings varied by pH protective coating or layer coating time as described in Table 3. Vials 97-112 were uncoated.

TABLE 3

Vial Coating Conditions

| Vial Number | Tie Coating (sec) | $SiO_x$ Coating g (sec) | pH Protective Coating (sec) |
|---|---|---|---|
| 1-16 | 2.5 | 10 | 0 |
| 17-32 | 2.5 | 10 | 2.5 |
| 33-48 | 2.5 | 10 | 5 |
| 49-64 | 2.5 | 10 | 10 |
| 65-80 | 2.5 | 10 | 15 |
| 81-96 | 2.5 | 10 | 20 |
| 97-112 | 0 | 0 | 0 |

Example 3—Syringe Study

A Block Engineering LaserScan 610 quantum cascade laser (QCL) operating nominally from 1440-978 $cm^{-1}$ at a spectral resolution of 4 $cm^{-1}$ was utilized. All spectra represent a single scan (co-add=1). Spectral Intensity at 1025 $cm^{-1}$ and 1070 $cm^{-1}$ was determined by the peak height method.

A number of 1 mL syringes were tested. Syringe set 1 received no coating, syringe set 2 received a tie coating, syringe set number 3 received a bilayer coating (tie coating or layer plus $SiO_x$ barrier coating or layer), and syringe set 4 received a trilayer coating (tie coating or layer plus $SiO_x$ barrier coating or layer, plus pH protective coating or layer). The front wall of each syringe was essentially solid except for the aperture for the needle opening.

A vertical configuration schematically illustrated in FIG. 5 was used for syringe barrel inspections, utilizing a three-axis mounting stage for syringe barrel placement relative to the laser source, impinging on the conical section 220 of the syringe barrel (the transition area between the cylindrical surface 44 and the plastic-needle or dispensing portion 20 interface. While the z axis distance was not critical, the x- and y-axis alignment as well as the degree of tilt was important to signal intensity. Under alignment conditions, the 2×4 mm laser source beam was fully inscribed inside the 6.25 mm ID shaft and did not reflect off the barrel flange. It was determined that the maximum reflection signal was obtained when the syringe bottoms were approximately 5.5 in. (14 cm) from the spectrometer collection lens. Because the syringes were narrow and relatively long, a secondary positioning adjustment was used to alter the tilt of each part to maximize the detected reflection signal. During the course of the preliminary measurements, it was also confirmed that the QCL beam entered the syringe barrels parallel to and offset radially from the axis and was not reflected off of the barrel flanges.

Four spectra at 0, 90, 180, and 270 degrees rotating the syringe on the z-axis 230 were taken for each syringe and averaged.

A roughened gold target was used as reference. The spectral scan time was about 14 seconds.

Figure 18:
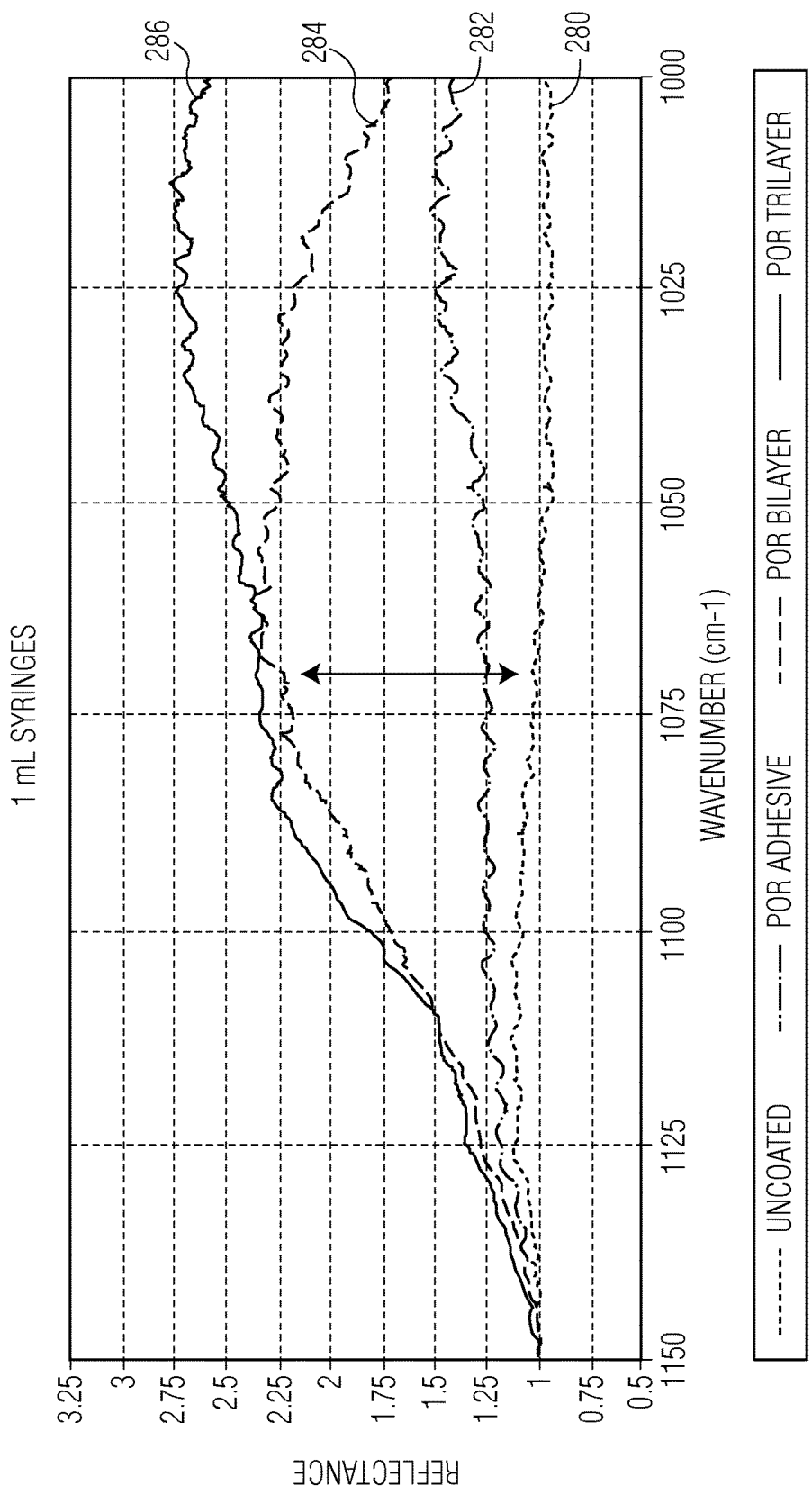
FIG. 18 is an infrared spectrophotometry spectrum plot of the syringe data of Example 3.

The spectra obtained, plotted on FIG. 18, clearly indicated no absorption at a peak 234 located at about 1025 $cm^{-1}$ for the uncoated barrels of set 1 (plot 280), a measurable absorption for the barrels of set 2 coated with a $SiO_xC_y$ tie coating or layer (plot 282), and a significant absorption for the barrels of set 4 having a trilayer coating consisting of a tie coating or layer plus an $SiO_x$ barrier coating or layer and further coated with a second $SiO_xC_y$ pH protective coating (plot 286).

The spectra obtained, plotted on FIG. 18, clearly indicated no absorption at a peak 234 located at about 1070 $cm^{-1}$ for the uncoated barrels of set 1 (plot 280), a weak absorption for the barrels of set 2, coated with a $SiO_xC_y$ tie coating or layer (plot 282) and a significant absorption for the barrels of set 3, coated with a $SiO_xC_y$ tie coating or layer plus an $SiO_x$ barrier coating or layer (plot 284). The spectra for the barrels of set 4, having a trilayer coating consisting of a tie coating or layer plus an $SiO_x$ barrier coating or layer and further coated with a second $SiO_xC_y$ pH protective coating (plot 286) indicated an absorption at a peak 234 located at about 1070 $cm^{-1}$ that was very similar to the peak for the barrels of set 3.

This study demonstrated that the $SiO_xC_y$ layer can be detected at the inside bottom of the test syringes in a non-destructive, non-contact fashion using a QCL spectrometer and an external gold film reference. This study also demonstrated that the $SiO_x$ layer can be detected at the inside bottom of the test syringes in a non-destructive, non-contact fashion using a QCL spectrometer and an external gold film reference.

While this interrogation of the syringe cone did not represent a comprehensive assessment of the total syringe barrel surface, it does represent results at a syringe location (4) of interest, in that Transmission Electron Microscopy thickness determinations indicated the front wall region typically has the thinnest coating over the syringe (FIG. 14).

Notably, each of the sets of syringes produced a spectrum having a unique shape, which can be described as a reflection fingerprint. Optionally, this fingerprint can be used for establishing Pass/Fail criteria for an inspected article.

Example 4—Vial Study

A second test was carried out under similar conditions to the test of Example 3, but using 5 mL vials in place of the 1 mL syringe barrels.

Figure 15:
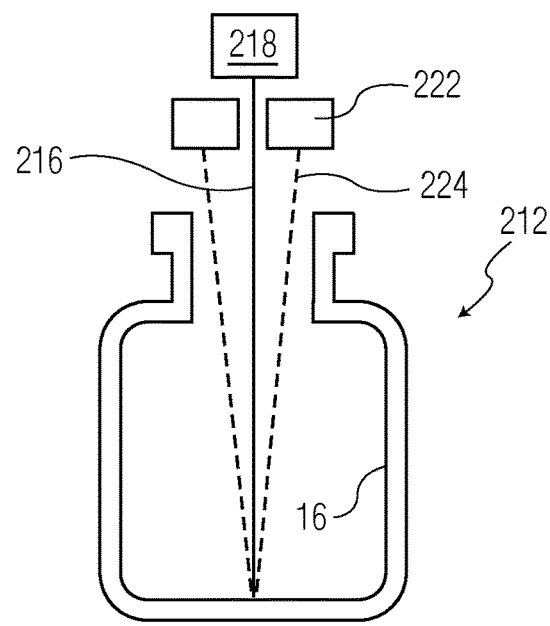
FIG. 15 is a view similar to FIG. 5 showing an arrangement for measuring spectroscopy data of a vial as employed in Example 2.

Each vial was measured with a beam path generally as shown in FIG. 15. Four measurements were taken in each vial by rotating it 90 degrees about its cylindrical axis between measurements; the four measurements for each vial and the measurements for all vials of each type were averaged.

Figure 19:
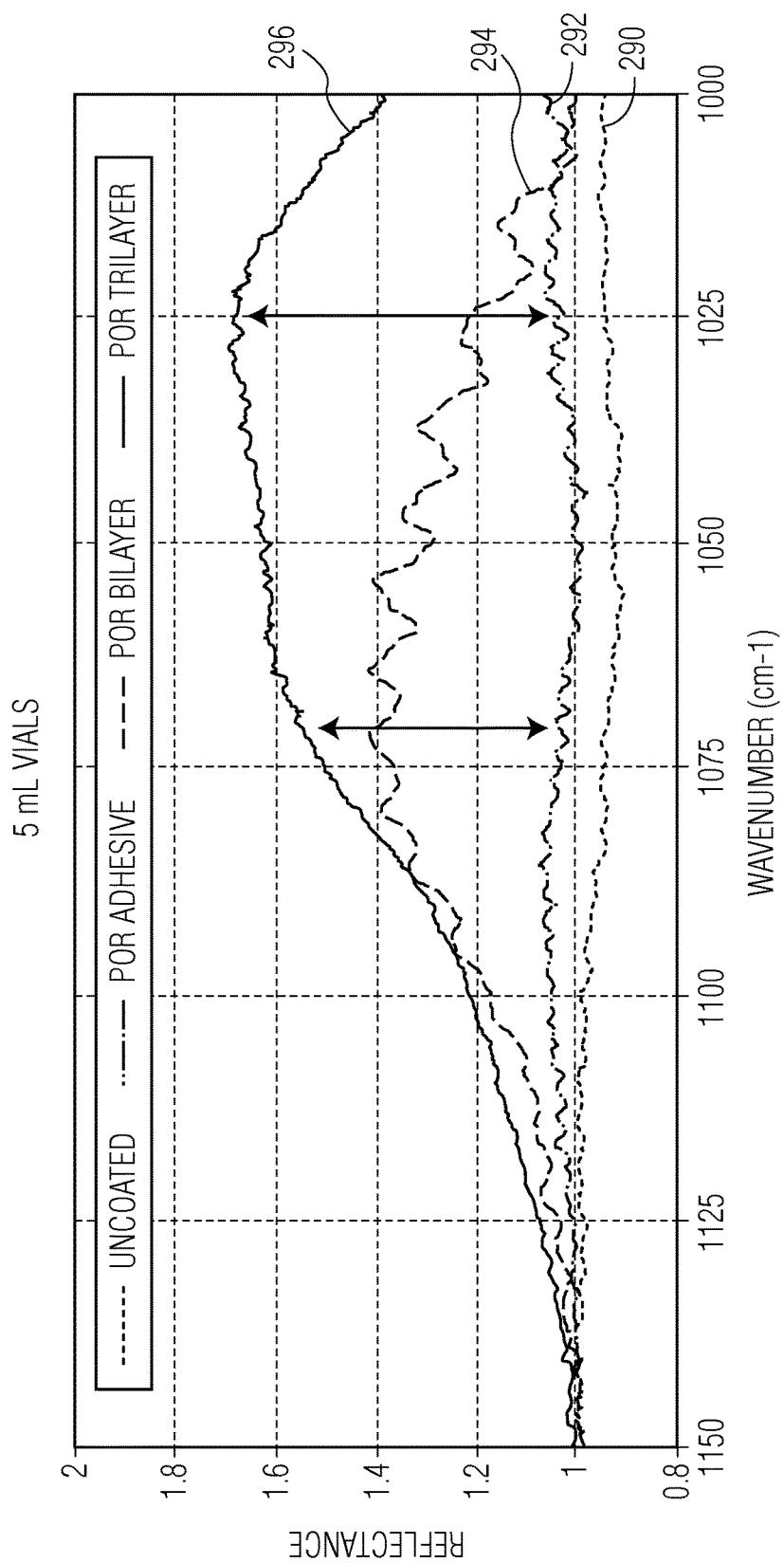
FIG. 19 is an infrared spectrophotometry spectrum plot of the vial data of Example 4.

The result is the plot shown in FIG. 19. The spectra obtained, clearly indicated no absorption at a peak 234 located at about 1025 $cm^{-1}$ for the uncoated vials of set 1 (plot 290), a measurable absorption for the vials of set 2 coated with a $SiO_xC_y$ tie coating or layer (plot 292), and a significant absorption for the vials of set 4 having a trilayer coating consisting of a tie coating or layer plus an $SiO_x$ barrier coating or layer and further coated with a second $SiO_xC_y$ pH protective coating (plot 296).

The spectra obtained, plotted on FIG. 19, also clearly indicated no absorption at a peak 234 located at about 1070 cm$^{-1}$ for the uncoated vials of set 1 (plot 290), a weak absorption for the vials of set 2, coated with a $SiO_xC_y$ tie coating or layer (plot 292) and a significant absorption for the vials of set 3, coated with a $SiO_xC_y$ tie coating or layer plus an $SiO_x$ barrier coating or layer (plot 294). The spectra for the vials of set 4, having a trilayer coating consisting of a tie coating or layer plus an $SiO_x$ barrier coating or layer and further coated with a second $SiO_xC_y$ pH protective coating (plot 296) indicated an absorption at a peak 234 located at about 1070 cm$^{-1}$ that was similar to the peak for the barrels of set 3.

The vials produced reflectance spectra with a characteristic peak at 1025 cm$^{-1}$ associated with the Si—CH$_3$ stretch of the $SiO_xC_y$ pH protective layer, and to a much lesser extent the much thinner $SiO_xC_y$ tie layer. The vials containing an $SiO_x$ barrier coating or layer also produced reflectance spectra with a characteristic peak at 1070 cm$^{-1}$.

This study demonstrated that the $SiO_xC_y$ layer and the $SiO_x$ layer can each be detected at the inside bottom of the vials in a non-destructive, non-contact fashion using a QCL spectrometer and an external gold film reference.

Notably, each of the sets of vials produced a spectrum having a unique shape, which can be described as a reflection fingerprint. Optionally, this fingerprint can be used for establishing Pass/Fail criteria for an inspected article.

Example 5—Vial Study with Various $SiO_xC_y$ Coating Times

Another test was carried out under similar conditions to the test of Example 4, but using 5 mL vials coated with an $SiO_xC_y$ tie layer, in which the coating of each vial with an $SiO_xC_y$ tie layer was performed for a different period of time, leading to an array of vials each having a tie layer of a different thickness. Vials were coated for a period of 1 second, 1.5 seconds, 2 seconds, 2.5 seconds (plot 300), 5 seconds (plot 302), 10 seconds (plot 304), and 15 seconds (plot 306).

Figure 20:
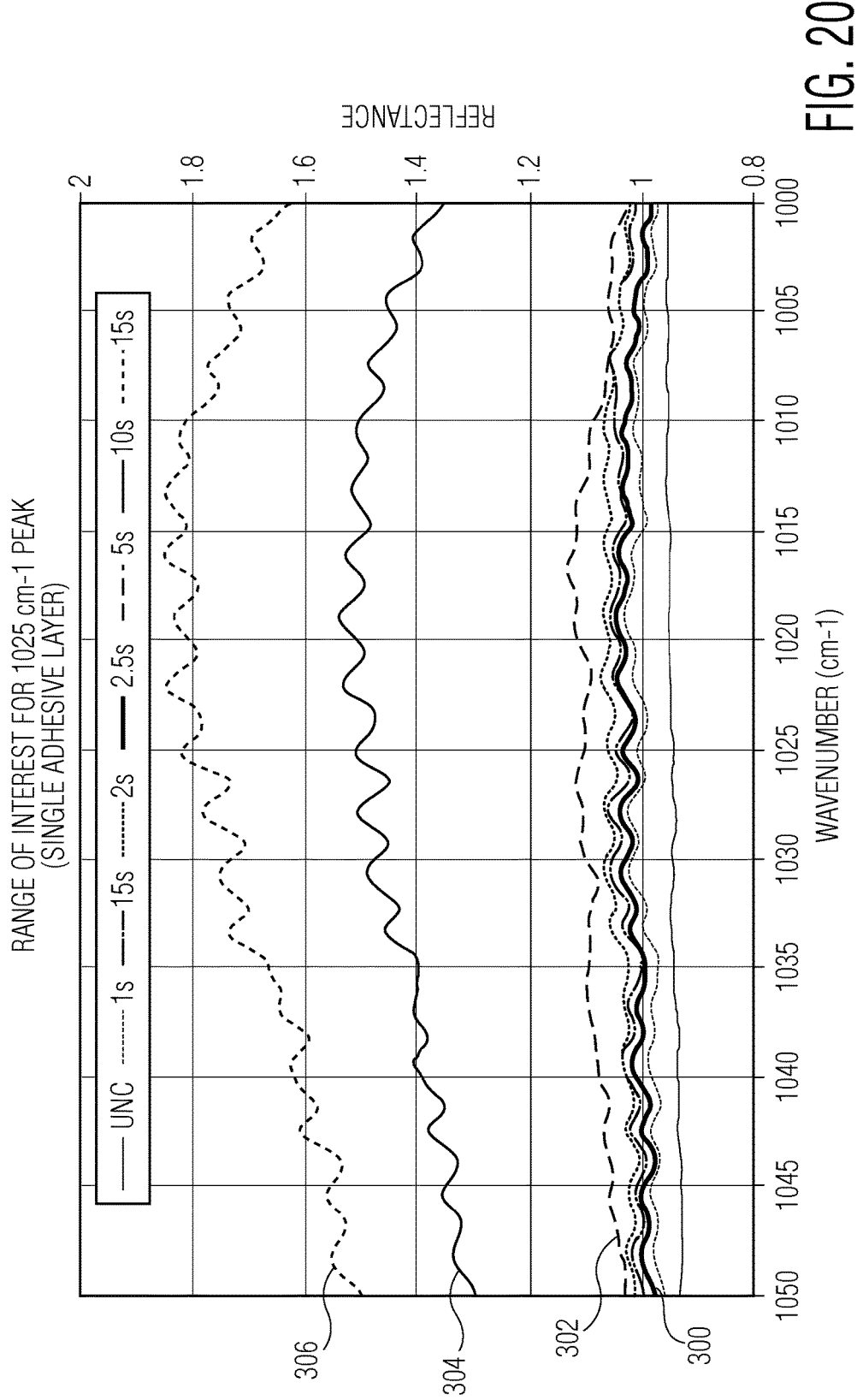
FIG. 20 is an infrared spectrophotometry spectrum plot of the vial data of Example 5.

The result is the plot shown in FIG. 20. Notably, the overall shape, or fingerprint, of each spectrum remains substantially the same as the coating time is increased. The overall intensity of the spectrum, however, increases in proportion with the increasing coating time.

Figure 21:
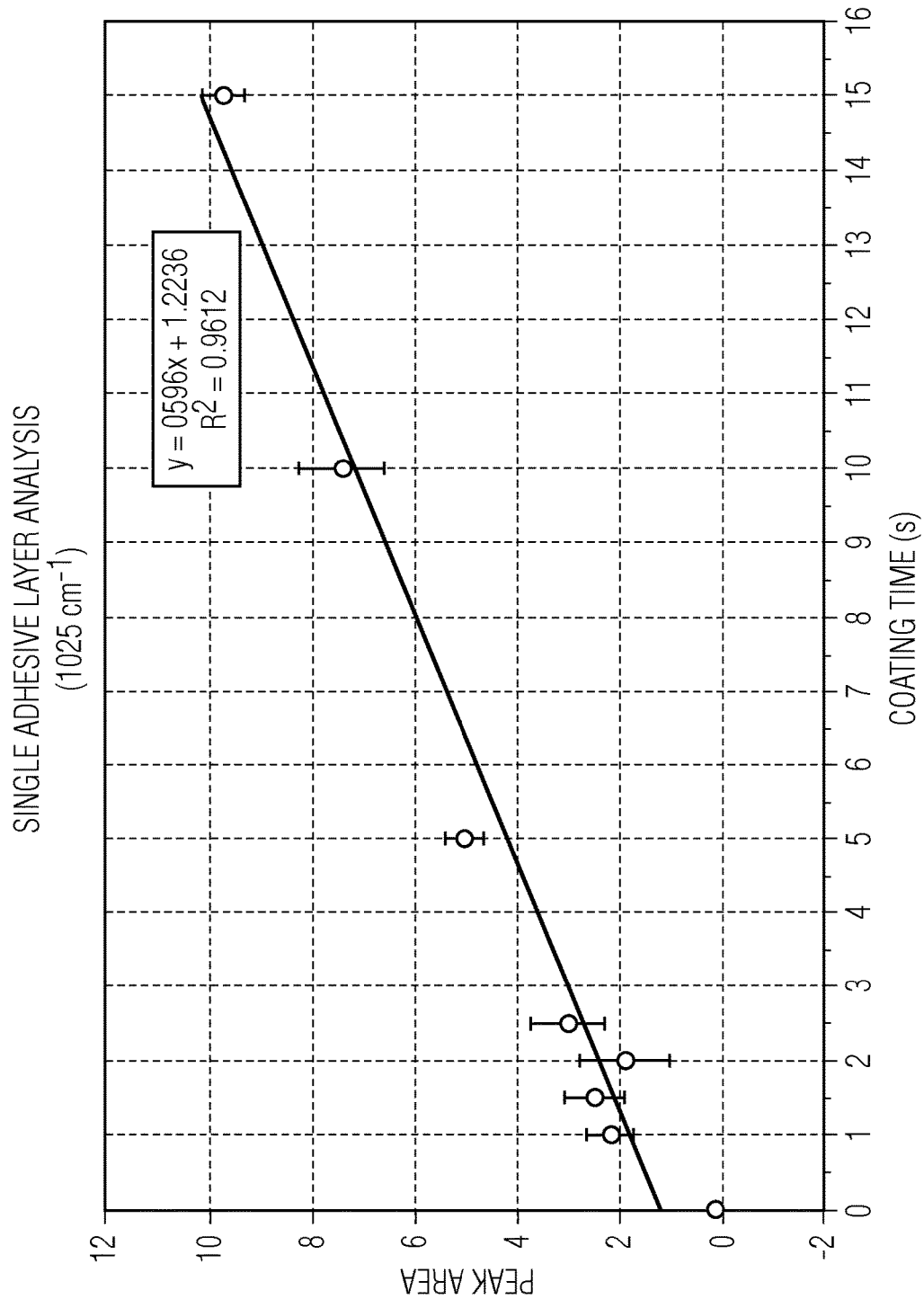
FIG. 21 is a linearized plot of peak area vs. coating time derived from the data shown in FIG. 22.

Plotting the absorbance of the vials at 1025 cm$^{-1}$ by the peak area method, shown in FIG. 21, after converting the reflectance data (R) to log(1/R) units (L) at each wavenumber point to linearize the ordinate axis, provided a linear regression (R2) of 0.9612, which is good for the small data set. Although the standard deviation appears greater than that shown in FIG. 13, the deviation is largely thought to result from the thinness of the tie layer compared to the bilayer or trilayer, such that the signal-to-noise ratio is decreased. Accordingly, below a coating time of 2.5 seconds, the ability to discern the tie layer using this method may be diminished. At coating times of 2.5 seconds or higher, however, the tie layer can be detected with confidence using the 1025 cm$^{-1}$ peak.

This study demonstrated that the $SiO_xC_y$ layer can be detected at the inside bottom of the test vials in a non-destructive, non-contact fashion using a QCL spectrometer and an external gold film reference and that the measured signals were generally proportional to the coating thicknesses.

Example 6—Vial Study with Various $SiO_x$ Coating Times

Another test was carried out under similar conditions to the test of Example 4, but using 5 mL vials coated with an $SiO_xC_y$ tie layer for a period of time of 2.5 seconds, followed by the coating of each vial with an $SiO_x$ barrier layer. The coating of the $SiO_x$ barrier layer was performed for a different period of time, leading to an array of vials each having a barrier layer of a different thickness. Vials were coated for a period of 2.5 seconds (plot 310), 5 seconds (plot 312), 10 seconds (plot 314), and 15 seconds (plot 316).

Figure 22:
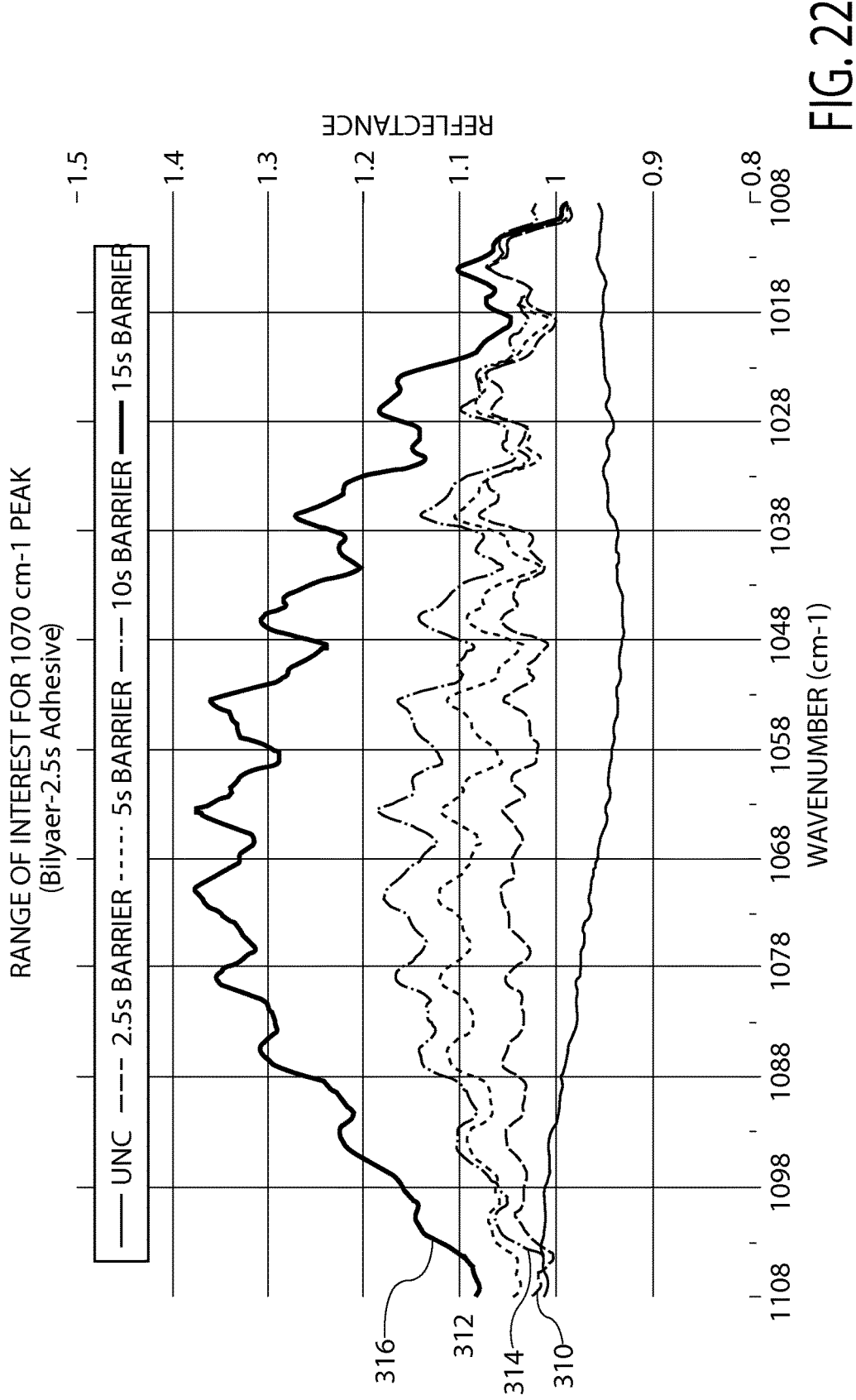
FIG. 22 is an infrared spectrophotometry spectrum plot of the vial data of Example 6.

The result is the plot shown in FIG. 22. Notably, the overall shape, or fingerprint, of each spectrum remains substantially the same as the coating time is increased. The overall intensity of the spectrum, however, increases in proportion with the increasing coating time.

Figure 23:
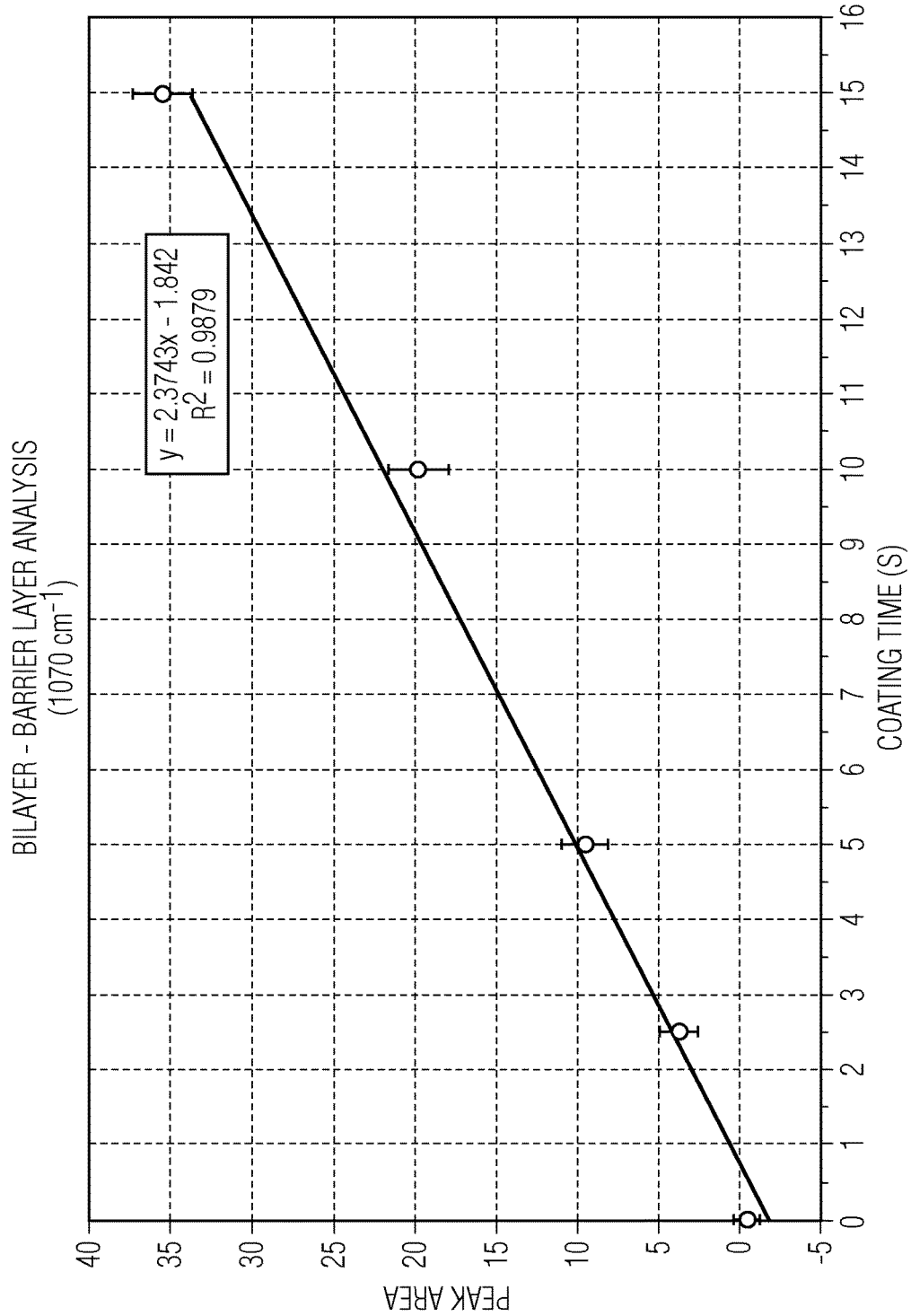
FIG. 23 is a linearized plot of peak area vs. coating time derived from the data shown in FIG. 24.

Plotting the absorbance of the vials at 1070 cm$^{-1}$ by the peak area method, shown in FIG. 23, after converting the reflectance data (R) to log(1/R) units (L) at each wavenumber point to linearize the ordinate axis, provided a linear regression (R2) of 0.9879, which is good for the small data set. Accordingly, the barrier layer can be detected with confidence using the 1070 cm$^{-1}$ peak.

This study demonstrated that the $SiO_x$ layer can be detected at the inside bottom of the test vials in a non-destructive, non-contact fashion using a QCL spectrometer and an external gold film reference and that the measured signals were generally proportional to the coating thicknesses.

Example 7—Simultaneous Detection of Barrier and Protective Layer

Due to the large intensity of the 1070 cm$^{-1}$ peak relating to the $SiO_x$ barrier layer (see FIGS. 18 and 19), it was decided to investigate whether the presence of the $SiO_x$ barrier coating or layer could be detected simultaneously with a $SiO_xC_y$ pH protective coating or layer.

Another test was therefore carried out under similar conditions to the test of Example 4, but using two sets of 5 mL vials. Each set of vials was coated with a trilayer coating consisting of (1) an $SiO_xC_y$ tie coating or layer, (2) an $SiO_x$ barrier coating or layer, and (3) an $SiO_xC_y$ protective coating or layer.

The first set of vials was produced using different coating times when preparing the barrier layer. Vials were coated with an $SiO_x$ barrier layer for a period of 2.5 seconds, 5 seconds, 10 seconds, and 15 seconds. For each of the vials within this set, the coating times for the tie layer and the protective layer were held constant—the tie layer being coated for 2.5 seconds and the protective layer being coated for 10 seconds.

Figure 24:
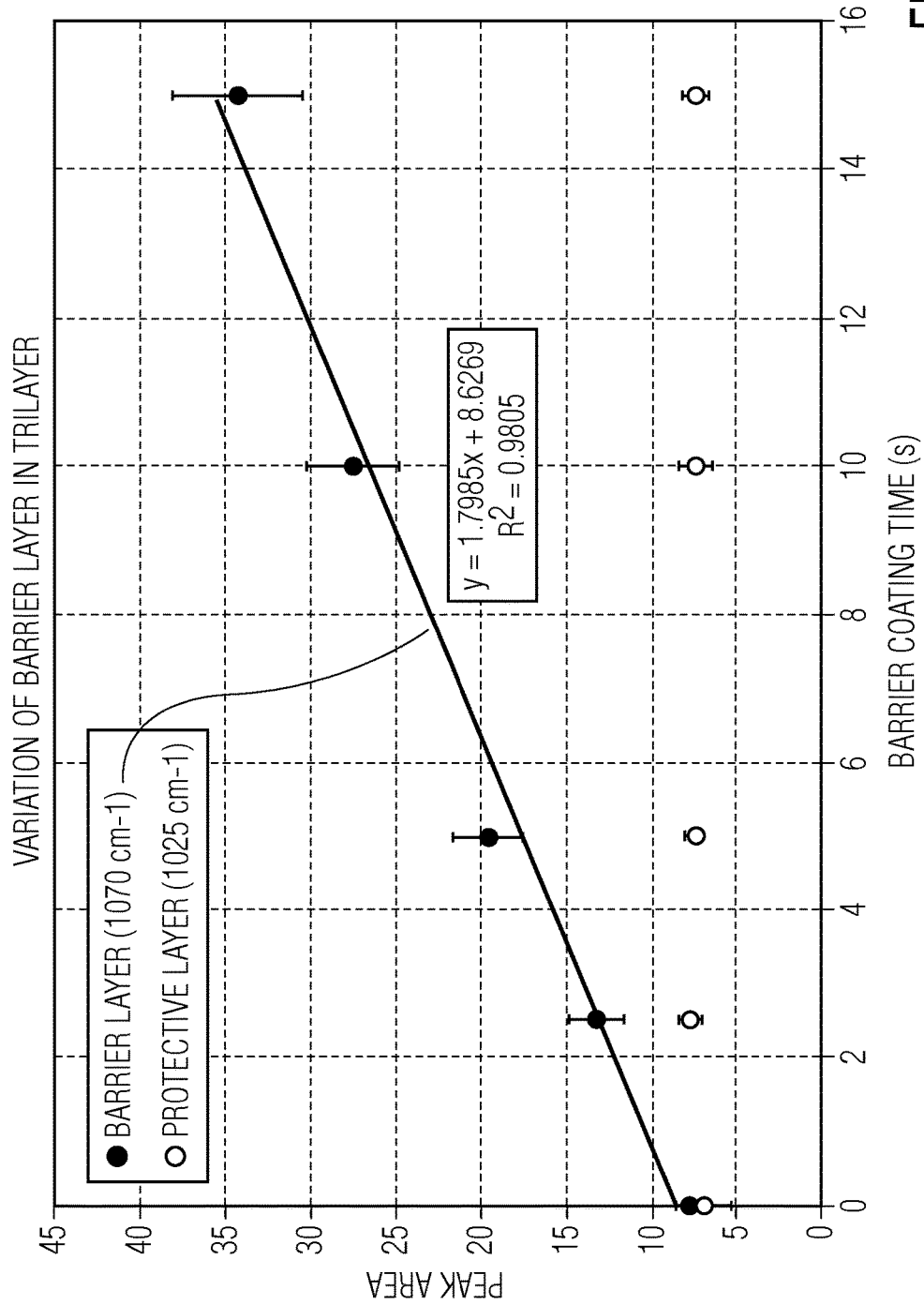
FIG. 24 is a linearized plot of peak area vs. coating time of the first set of vial data of Example 7.

The absorbance of the first set of vials at both 1025 cm$^{-1}$ and 1070 cm$^{-1}$ was plotted by the peak area method, shown in FIG. 24. After converting the reflectance data (R) to log(1/R) units (L) at each wavenumber point to linearize the ordinate axis, the plot at 1070 cm$^{-1}$ provided a linear regression (R2) of 0.9805, which is good for the small data set. Accordingly, the barrier layer can be independently detected with confidence using the 1070 cm$^{-1}$ peak in the presence of the protective layer.

Moreover, the peak area at 1025 cm$^{-1}$ was substantially unchanged by the increased barrier layer coatings. Accordingly, the presence of the barrier layer does not give rise to a peak at 1025 cm$^{-1}$, confirming that the presence of the barrier layer does not interfere with detection of the SiO$_x$C$_y$ protective layer using the peak at 1025 cm$^{-1}$.

The second set of vials was produced using different coating times when preparing the protective layer. Vials were coated with an SiO$_x$C$_y$ protective layer for a period of 2.5 seconds, 5 seconds, 10 seconds, and 15 seconds. For each of the vials within this set, the coating times for the tie layer and the barrier layer were held constant—the tie layer being coated for 2.5 seconds and the barrier layer being coated for 15 seconds.

Figure 25:
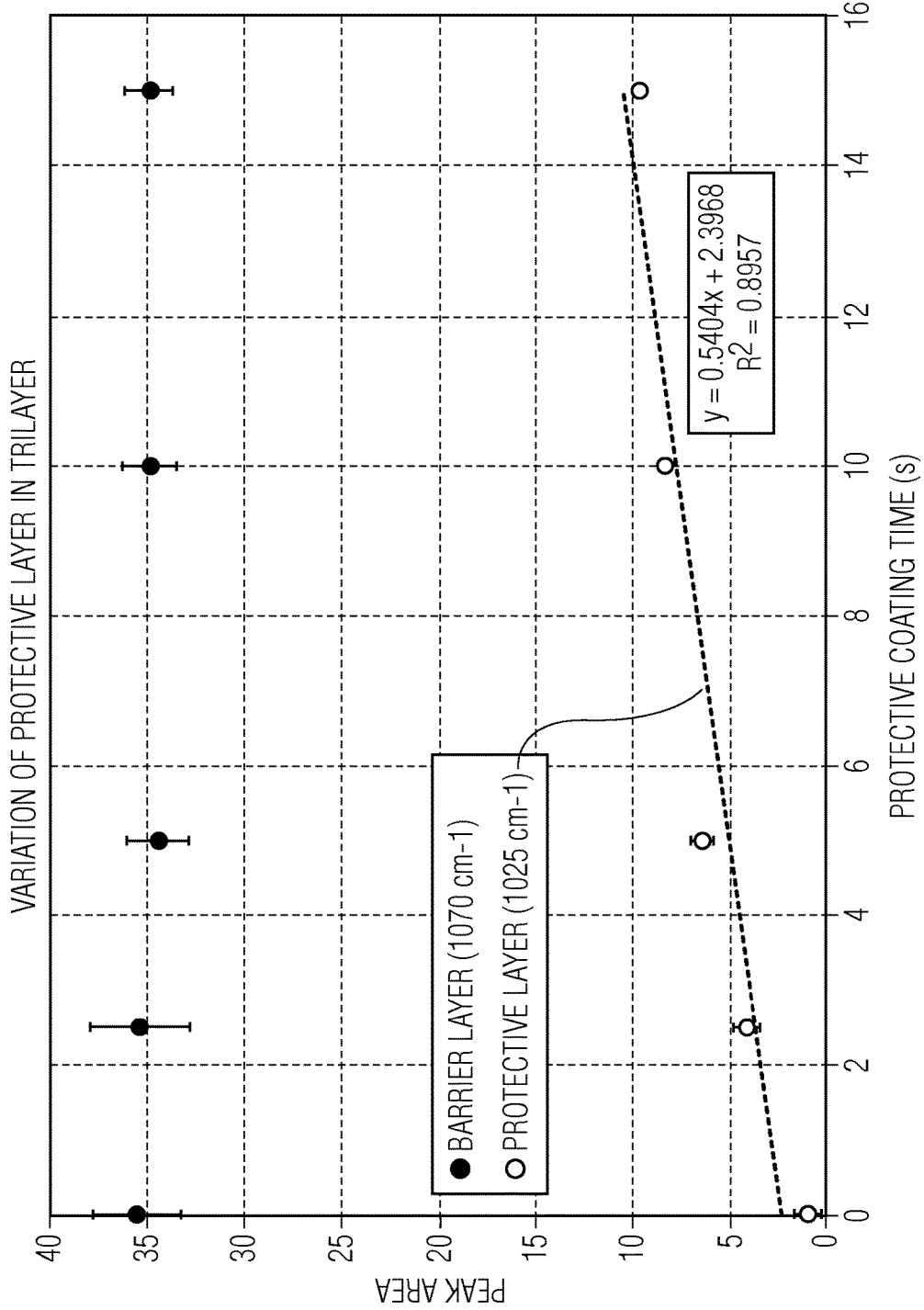
FIG. 25 is a linearized plot of peak area vs. coating time of the second set of vial data of Example 7.

The absorbance of the second set of vials at both 1025 cm$^{-1}$ and 1070 cm$^{-1}$ was plotted by the peak area method, shown in FIG. 25. After converting the reflectance data (R) to log(1/R) units (L) at each wavenumber point to linearize the ordinate axis, the plot at 1025 cm$^{-1}$ provided a linear regression (R2) of 0.8957, which is good for the small data set. Accordingly, the protective layer can be independently detected with confidence using the 1025 cm$^{-1}$ peak in the presence of the barrier layer.

Moreover, the peak area at 1070 cm$^{-1}$ was substantially unchanged by the increased protective layer coatings. Accordingly, the presence of the protective layer does not give rise to a peak at 1070 cm$^{-1}$, confirming that the presence of the protective layer does not interfere with detection of the SiO$_x$ barrier layer using the peak at 1070 cm$^{-1}$.

This study demonstrated that a SiO$_x$C$_y$ layer and a SiO$_x$ layer can simultaneously be detected at the inside bottom of the test vials in a non-destructive, non-contact fashion using a QCL spectrometer and an external gold film reference and that the measured signals were each independently generally proportional to the coating thickness of the individual layer with which the signal was associated.

During the inspection of a number of syringes using the Block Engineering LaserScan 610 quantum cascade laser (QCL) described above, it was found that response output was occasionally skewed and, in some cases, may have indicated false positives, i.e. appeared to indicate the presence of coatings on uncoated articles. It was determined that the metallic needle was causing the output response to have artificial spikes, likely due to the reflective nature of the metal.

The inaccuracies that may be caused by the metal needle during the inspection of syringes using embodiments of the present invention may, however, be prevented. For example, the source of infrared light 218 may be modified so that the light does not impinge on and interact with the needle. For instance, when a laser is used as the source of infrared light 218, the optical path of the laser beam may be selectively masked in order to prevent the light from impinging on and interacting with the needle.

Alternatively, the syringes 700 may be modified to minimize or eliminate the contribution of the needle 702 to the light that is collected, and thus minimize or eliminate the artificial peaks in the output response that may be caused by the interaction of the light with the needle. This can be achieved, for example, by modifying the syringe 700 so as to increase the diameter of the flat surface 704, sometimes referred to as the "land," that surrounds the needle 702. This flat surface 704 is important because it provides for the specular reflection that results in collection of the impinged light, as opposed to curved surfaces that may scatter the light in directions away from the detection lens.

Figure 27:
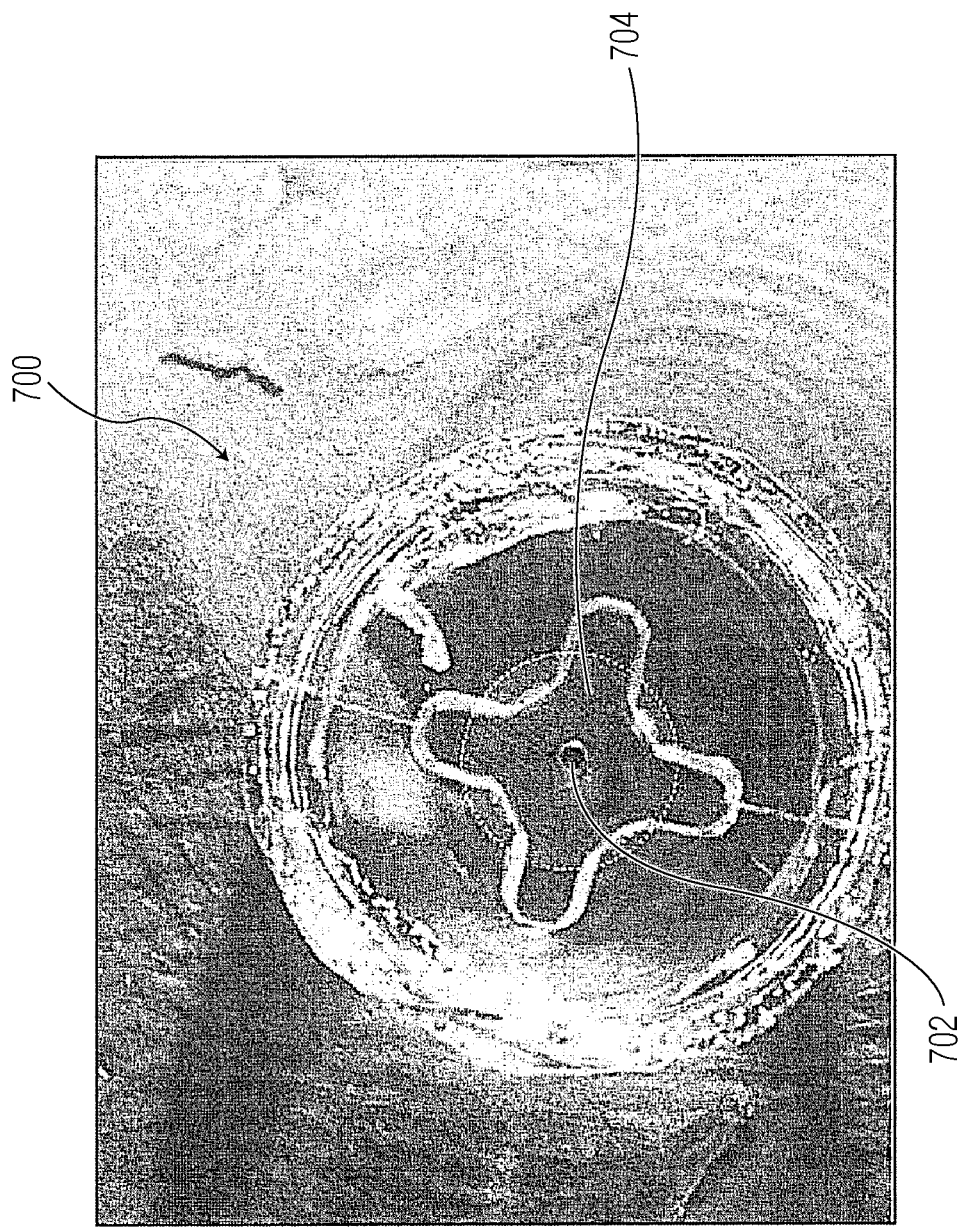
FIG. 27 is an optical microscope photograph of a syringe comprising an enhanced "land" surface having a diameter of 2.67 mm.

Accordingly, in some embodiments, a syringe 700 comprising a land surface 704 that has a diameter of greater than 1 mm, alternatively greater than 1.5 mm, alternatively greater than 2 mm, and alternatively greater than 2.5 mm may be provided. For example, a syringe 700 comprising a land 704 that has a diameter of about 3 mm may be provided. An embodiment of a syringe 700 comprising an enhanced land surface 704 is shown in FIG. 27. Inspection of a syringe 700 having an enhanced land surface 704 may be performed without any significant contribution from the needle 702 in the collected light signal.

Figure 26:
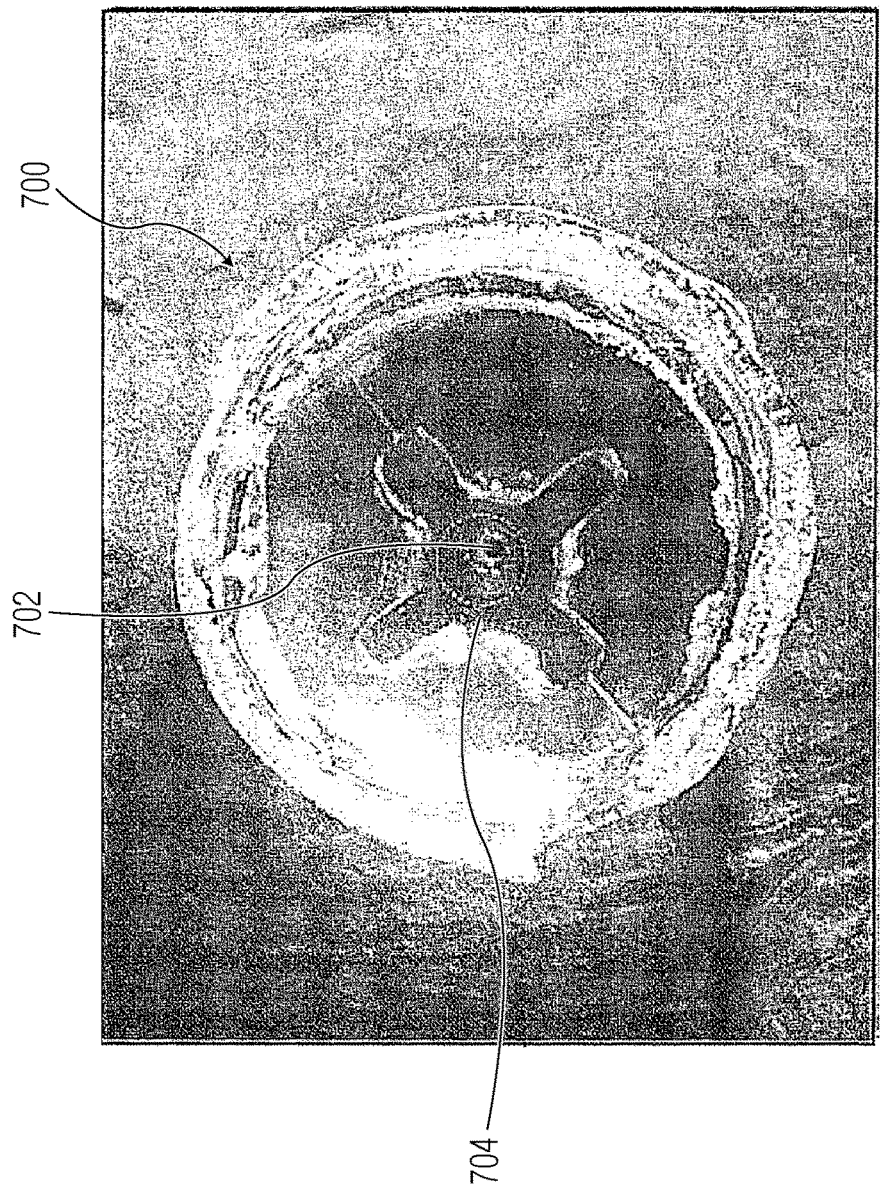
FIG. 26 is an optical microscope photograph of a syringe comprising a conventional "land" surface having a diameter of about 1 mm.

The minimization of the contribution of the needle 702 is demonstrated by the following example. In a conventional syringe 700, such as is shown in FIG. 26, the needle 702 has an outer diameter of about 0.4 mm and the land 704 has a diameter of about 1 mm. Taking into account the area on which the sample laser impinges, the contribution of the needle 702 to the total land area is about 16%. However, by increasing the diameter of the land 704 to about 2.67 mm, while maintaining the same needle diameter, the contribution of the needle 702 to the total land area may be decreased to about 2%. It was determined that inspection of syringes 700 having the enhanced land surface 704 yielded no false positives. It has therefore been found that a small increase in the diameter of the land 704 may minimize or even effectively eliminate the contribution of the needle 702 to the collected light signal. Testing also suggests that the enhanced land area does not have any appreciable impact on the performance of the syringe.

TABLE 4

| Sample Effect of Enhanced Land Area | | |
| --- | --- | --- |
| Land Diameter (mm) | 1 | 2.67 |
| Needle/Hole OD (mm) | 0.4 | |
| COP Area to Inspect (mm^2) | 0.66 | 5.46 |
| Contribution of Needle to Total Land Area | 16% | 2% |

An increase in the flat portion of the inspection surface of an article may be used to enhance the collected signal for the inspection of other articles as well. For example, blood tubes having an increased flat portion could be provided in order to provide for improved inspection by the methods described herein. The increased flat surface may be provided by control over the molding of the article or by other processes. For instance, stretch blow molding may be used to provide a vial having a flatter inspection surface that produces a stronger signal using the inspection methods described herein.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art and practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

What is claimed:

1. A non-destructive method of detecting whether a coating or deposit of SiO$_x$C$_y$ or SiN$_x$C$_y$, where x is from about 0.5 to about 2.4 and y is from about 0.6 to about 3, is present on or near an interior distal end surface of an article, the method comprising:
- providing as the article a generally cylindrical vessel comprising a distal end, a proximal end, a lumen, an interior distal end surface defining at least a portion of the lumen, and a back opening at the proximal end of the generally cylindrical vessel,
- impinging infrared light having a wave number in one or more of (a) at least a portion of a range between 950 and 1230 $cm^{-1}$ and (b) at least a portion of a range between 1230 and 1300 $cm^{-1}$ from apparatus spaced from the interior distal end surface, onto the interior distal end surface, to examine the interior distal end surface for the presence of a coating or deposit of $SiO_xC_y$ or $SiN_xC_y$,
- reflecting the impinged infrared light from the interior distal end surface through the back opening of the generally cylindrical vessel;
- collecting at least a portion of the infrared light reflected through the back opening of the generally cylindrical vessel; and
- detecting whether the coating or deposit of $SiO_xC_y$ or $SiN_xC_y$ is present by measuring the response output of the collected infrared light in one or more of (a) at least a portion of a range between 950 and 1230 $cm^{-1}$ and (b) at least a portion of a range between 1230 and 1300 $cm^{-1}$.

2. The method of claim 1, in which the coating or deposit of $SiO_xC_y$ or $SiN_xC_y$ is a tie coating or layer for increasing adhesion between the interior distal end surface and a subsequent coating or layer.

3. The method of claim 1, in which the coating or deposit of $SiO_xC_y$ or $SiN_xC_y$ is a pH protective coating or layer having the property of reducing the dissolution of silicon from the interior distal end surface by an aqueous fluid having a pH of at least 5.

4. The method of claim 1, in which a coating or deposit of $SiO_x$, where x is from about 1.5 to about 2.9, is also present on the interior distal end surface of the article.

5. The method of claim 1, in which the interior distal end surface of the article comprises a first coating or deposit of $SiO_xC_y$ or $SiN_xC_y$, where x is from about 0.5 to about 2.4 and y is from about 0.6 to about 3, and a second coating or deposit of $SiO_xC_y$ or $SiN_xC_y$, where x is from about 0.5 to about 2.4 and y is from about 0.6 to about 3, and wherein detecting the presence of at least one of the first coating or deposit and the second coating or deposit comprises measuring the response output of the collected infrared light at an infrared spectroscopy peak in one or more of (a) at least a portion of a range between 950 and 1230 $cm^{-1}$ and (b) at least a portion of a range between 1230 and 1300 $cm^{-1}$, the measured response output being indicative of at least one of the first coating or deposit of $SiO_xC_y$ or $SiN_xC_y$ and the second coating or deposit of $SiO_xC_y$ or $SiN_xC_y$.

6. The method of claim 1, in which the impinging of infrared light onto at least a first surface and the collecting at least a portion of the infrared light impinged on the first surface are performed on a production line for the article.

7. The method of claim 1, in which the measured response output comprises the maximum intensity at an infrared spectroscopy peak, a peak area of the collected infrared light at an infrared spectroscopy peak, or both.

8. The method of claim 7, in which the article is assigned a status of either passing or failing based on the comparison between the maximum intensity and/or peak area of the collected infrared light and a predetermined parameter.

9. The method of claim 1, in which collecting the infrared light is carried out by passing the light from the first surface through the opening to a collector positioned entirely outside the lumen.

10. The method of claim 1, in which the interior distal end surface is located generally opposite the back opening.

11. The invention of claim 1, in which the infrared light is provided by a frequency tunable laser.

12. The invention of claim 1, in which the infrared light travels at least about one inch before it impinges onto the first surface.

13. The invention of claim 1, in which a coating or deposit of mold lubricant is present, directly or indirectly, on a surface of the article.

14. The method of claim 1, in which the article comprises a syringe barrel.

15. The method of claim 14, in which the syringe barrel comprises a needle and the interior distal end surface comprises a land surface surrounding the needle, the land surface comprising a diameter from greater than 1.5 mm to about 3 mm.

16. The method of claim 1, in which the article comprises a vial.

17. The method of claim 1, in which the combination of the impinging and collecting steps is performed in four seconds or less, optionally three seconds or less, optionally two seconds or less, optionally one second or less, optionally one-half of a second or less.

18. A non-destructive method of detecting whether a coating or deposit of $SiO_x$, where x is from about 1.5 to about 2.9, is present on or near an interior distal end surface of an article, the method comprising:
- providing as the article a generally cylindrical vessel comprising a distal end, a proximal end, a lumen, an interior distal end surface defining at least a portion of the lumen, and a back opening at the proximal end of the generally cylindrical vessel,
- impinging infrared light having a wave number in at least a portion of a range from about 1060 to about 1080 $cm^{-1}$ from apparatus spaced from the interior distal end surface, through the back opening of the generally cylindrical vessel, onto the interior distal end surface to examine the interior distal end surface for the presence of a coating or deposit of $SiO_x$, reflecting the impinged infrared light from the interior distal end surface through the back opening of the generally cylindrical vessel,
- collecting at least a portion of the infrared light reflected through the back opening of the generally cylindrical vessel; and
- measuring the response output of the collected infrared light in at least a portion of the range from about 1060 to about 1080 $cm^{-1}$, the measured response output being indicative of a coating or deposit of $SiO_x$.

19. The method of claim 18, in which the coating or deposit of $SiO_x$ is a gas barrier coating or layer.

20. The method of claim 18, in which a coating or deposit of $SiO_xC_y$ or $SiN_xC_y$, where x is from about 0.5 to about 2.4 and y is from about 0.6 to about 3, is also present on or near a surface of an article.

21. A non-destructive method of detecting whether (a) a coating or deposit of $SiO_xC_y$ or $SiN_xC_y$, where x is from about 0.5 to about 2.4 and y is from about 0.6 to about 3 and (b) a coating or deposit of $SiO_x$, where x is from about 1.5 to about 2.9, are present on or near an interior distal end surface of an article, the method comprising:

providing as the article a generally cylindrical vessel comprising a distal end, a proximal end, a lumen, an interior distal end surface defining at least a portion of the lumen, and a back opening at the proximal end of the generally cylindrical vessel, impinging infrared light from apparatus spaced from the interior distal end surface, onto the interior distal end surface to examine the interior distal end surface for the presence of the coatings or deposits;

reflecting the impinged infrared light from the interior distal end surface through the back opening of the generally cylindrical vessel, collecting at least a portion of the infrared light reflected through the back opening of the generally cylindrical vessel;

detecting whether the coating or deposit of $SiO_xC_y$ or $SiN_xC_y$ is present by measuring the response output of the collected infrared light in one or more of (a) at least a portion of a range between 950 and 1230 $cm^{-1}$ and (b) at least a portion of a range between 1230 and 1300 $cm^{-1}$; and detecting whether the coating or deposit of $SiO_x$ is present by measuring the response output of the collected infrared light in at least a portion of the range from about 1060 to about 1080 $cm^{-1}$.

22. The method of claim 21, in which the presence or absence of the coating or deposit of $SiO_xC_y$ or $SiN_xC_y$ is detected in the presence or absence of the coating or deposit of $SiO_x$.

23. The method of claim 21, in which the presence or absence of the coating or deposit of $SiO_x$ is detected in the presence or absence of the coating or deposit of $SiO_xC_y$ or $SiN_xC_y$.

24. A non-destructive method of detecting whether at least three coatings, comprising (a) a first coating or deposit of $SiO_xC_y$ or $SiN_xC_y$, where x is from about 0.5 to about 2.4 and y is from about 0.6 to about 3, (b) a coating or deposit of $SiO_x$, where x is from about 1.5 to about 2.9, and (c) a second coating or deposit of $SiO_xC_y$ or $SiN_xC_y$, where x is from about 0.5 to about 2.4 and y is from about 0.6 to about 3, are present on or near a surface of an article, the method comprising:

providing an article with the first coating or deposit of $SiO_xC_y$ or $SiN_xC_y$, and without the second coating or deposit of $SiO_xC_y$ or $SiN_xC_y$;

in a first analysis:

impinging infrared light onto at least a first surface being examined for the presence of the coatings or deposits;

collecting at least a portion of the infrared light impinged on the first surface;

measuring the response output maximum intensity and/or peak area of the collected infrared light at an infrared spectroscopy peak, in one or more of (a) at least a portion of a range between 950 and 1230 $cm^{-1}$ and (b) at least a portion of a range between 1230 and 1300 $cm^{-1}$ to indicate a coating or deposit of $SiO_xC_y$ or $SiN_xC_y$;

applying the second coating or deposit of $SiO_xC_y$ or $SiN_xC_y$ to the article;

in a second analysis:

impinging infrared light onto at least a first surface being examined for the presence of the coatings or deposits;

collecting at least a portion of the infrared light impinged on the first surface;

measuring the response output maximum intensity and/or peak area of the collected infrared light at an infrared spectroscopy peak, in one or more of (a) at least a portion of a range between 950 and 1230 $cm^{-1}$ and (b) at least a portion of a range between 1230 and 1300 $cm^{-1}$ to indicate a coating or deposit of $SiO_xC_y$ or $SiN_xC_y$; and determining whether the response output maximum intensity and/or peak area of the collected infrared light indicative of the presence of a coating or deposit of $SiO_xC_y$ or $SiN_xC_y$ is greater in the second analysis than in the first analysis, indicating the presence of both the first and second coating or deposit of $SiO_xC_y$ or $SiN_xC_y$.

25. The method of claim 24, in which the article with the first coating or deposit of $SiO_xC_y$ or $SiN_xC_y$, and without the second coating or deposit of $SiO_xC_y$ or $SiN_xC_y$, further comprises the coating or deposit of $SiO_x$.

26. The method of claim 24, in which the coating or deposit of $SiO_x$ is applied after the first coating or deposit of $SiO_xC_y$ or $SiN_xC_y$ is applied, and before the second coating or deposit of $SiO_xC_y$ or $SiN_xC_y$ is applied.

27. The method of claim 22, in which the coating or deposit of $SiO_x$ is applied before the first analysis.

28. The method of claim 22, in which the coating or deposit of $SiO_x$ is applied after the first analysis and before the second analysis.

* * * * *